United States Patent
Pearson et al.

(10) Patent No.: US 7,344,533 B2
(45) Date of Patent: Mar. 18, 2008

(54) IMPEDANCE CONTROLLED TISSUE ABLATION APPARATUS AND METHOD

(75) Inventors: Robert M. Pearson, San Jose, CA (US); Steven A. Daniel, Fremont, CA (US); Daniel J. Balbierz, Redwood City, CA (US); Theodore C. Johnson, Ann Arbor, MI (US); Zia Yassinzadeh, San Jose, CA (US)

(73) Assignee: Angiodynamics, Inc., Queensbury, NY (US)

( * ) Notice: Subject to any disclaimer, the term of this patent is extended or adjusted under 35 U.S.C. 154(b) by 0 days.

(21) Appl. No.: 10/260,187

(22) Filed: Sep. 28, 2002

(65) Prior Publication Data

US 2003/0130711 A1    Jul. 10, 2003

Related U.S. Application Data

(60) Provisional application No. 60/326,043, filed on Sep. 28, 2001.

(51) Int. Cl.
*A61B 18/18* (2006.01)

(52) U.S. Cl. .................. 606/41; 607/105; 607/102; 606/42

(58) Field of Classification Search .............. 606/41, 606/42, 45–50, 21, 22; 607/100–105
See application file for complete search history.

(56) References Cited

U.S. PATENT DOCUMENTS

| | | | |
|---|---|---|---|
| 5,254,117 A * | 10/1993 | Rigby et al. ................ 606/46 |
| 5,281,218 A | 1/1994 | Imran | |
| 5,334,193 A | 8/1994 | Nardella | |
| 5,336,222 A | 8/1994 | Durgin, Jr. et al. | |
| 5,370,675 A | 12/1994 | Edwards et al. | |
| 5,403,311 A | 4/1995 | Abele et al. | |
| 5,431,649 A | 7/1995 | Mulier et al. | |
| 5,437,662 A * | 8/1995 | Nardella ................... 606/40 |
| 5,454,807 A | 10/1995 | Lennox et al. | |
| 5,536,267 A | 7/1996 | Edwards et al. | |
| 5,556,377 A | 9/1996 | Rosen et al. | |
| 5,599,345 A | 2/1997 | Edwards et al. | |
| 5,609,151 A | 3/1997 | Mulier et al. | |
| 5,620,481 A | 4/1997 | Desai et al. | |
| 5,725,524 A | 3/1998 | Mulier et al. | |

(Continued)

FOREIGN PATENT DOCUMENTS

DE       2124 684       11/1972

(Continued)

*Primary Examiner*—Michael Peffley
(74) *Attorney, Agent, or Firm*—Perkins Coie LLP

(57) ABSTRACT

A method and apparatus for carrying our thermal ablation of target tissue is disclosed. The apparatus includes an RF ablation device having a multi-electrode electrode assembly designed to be deployed in target tissue, defining a selected-volume tissue region to be ablated, and having infusion channels for infusing a liquid into the target tissue during the ablation process. A control unit in the apparatus is operably connected to an RF energy source, for controlling the RF power level supplied to the electrodes, and to an infusion device, for controlling the rate of infusion of a liquid through the device into the tissue. During both electrode deployment and tissue ablation, impedance and or temperature measurements made within the tissue are used to control the RF source and infusion device, for optimizing the time and extent of tissue ablation.

22 Claims, 31 Drawing Sheets

U.S. PATENT DOCUMENTS

| | | | |
|---|---|---|---|
| 5,776,176 A * | 7/1998 | Rudie | 607/101 |
| 5,800,482 A | 9/1998 | Pomeranz et al. | |
| 5,807,395 A | 9/1998 | Mulier et al. | |
| 5,817,092 A | 10/1998 | Behl | |
| 5,827,276 A | 10/1998 | Leveen et al. | |
| 5,855,576 A | 1/1999 | Leveen et al. | |
| 5,868,740 A | 2/1999 | Leveen et al. | |
| 5,876,398 A | 3/1999 | Mulier et al. | |
| 5,891,095 A | 4/1999 | Eggers et al. | |
| 5,897,553 A | 4/1999 | Mulier et al. | |
| 5,902,328 A | 5/1999 | LaFontaine et al. | |
| 5,906,613 A | 5/1999 | Mulier et al. | |
| 6,016,809 A | 1/2000 | Mulier et al. | |
| 6,024,739 A | 2/2000 | Ponzi et al. | |
| 6,030,379 A | 2/2000 | Panescu et al. | |
| 6,032,077 A | 2/2000 | Pomeranz | |
| 6,056,747 A | 5/2000 | Saadat et al. | |
| 6,059,780 A * | 5/2000 | Gough et al. | 606/42 |
| 6,063,081 A | 5/2000 | Mulier et al. | |
| 6,086,585 A | 7/2000 | Hovda et al. | |
| 6,090,105 A | 7/2000 | Zepeda et al. | |
| 7,160,296 B2 * | 1/2007 | Pearson et al. | 606/42 |

FOREIGN PATENT DOCUMENTS

| | | |
|---|---|---|
| WO | WO 00/09208 | 2/2000 |
| WO | WO 00/09209 | 2/2000 |
| WO | WO 00/13603 | 3/2000 |

* cited by examiner

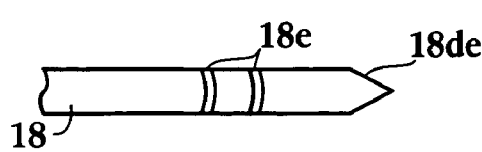
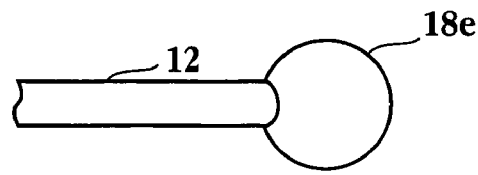
Fig. 15A        Fig. 15B
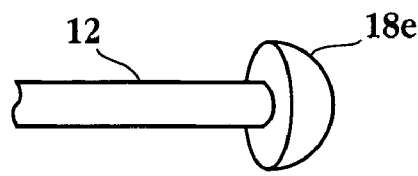
Fig. 15C        Fig. 15D
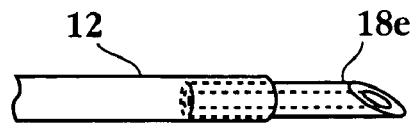
Fig. 15E        Fig. 15F
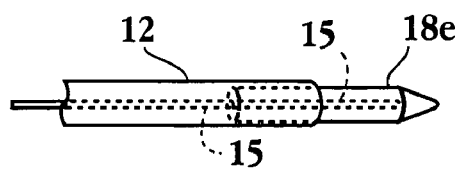
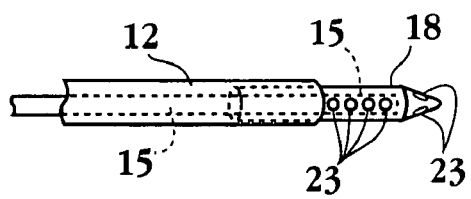
Fig. 15G        Fig. 15H

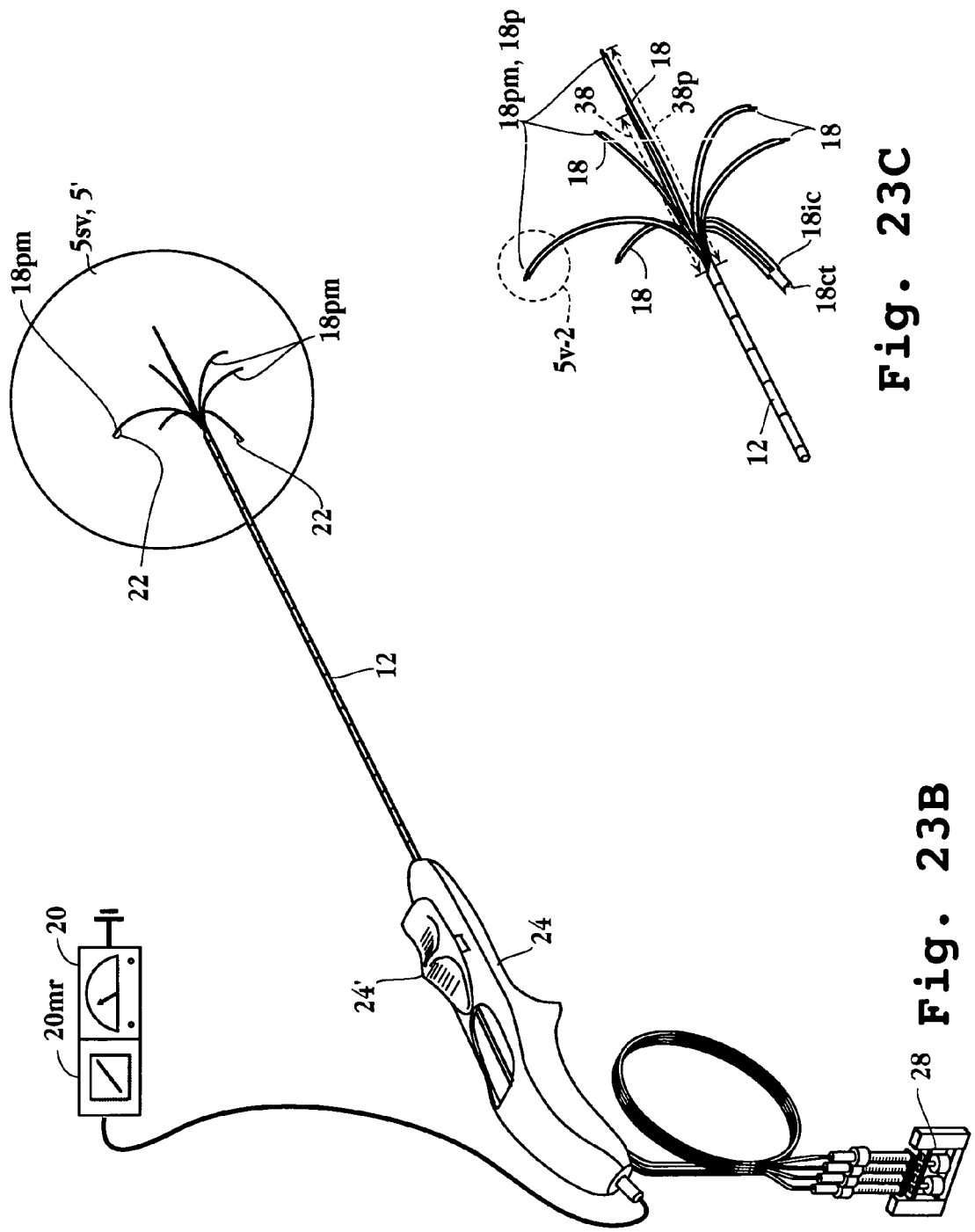

IMPEDANCE CONTROLLED TISSUE ABLATION APPARATUS AND METHOD

This application claims the benefit of U.S. Provisional Application No. 60/326,043 filed Sep. 28, 2001, which is incorporated herewith by reference in its entirety.

FIELD OF THE INVENTION

This invention relates generally to a method for treating tissue using minimally invasive methods. More particularly, the invention relates to an apparatus and method for ablatively treating tumorous and diseased tissue. Still more particularly, the invention relates to an apparatus and method for ablatively treating tumorous tissue using impedance values to control and optimize the delivery of electromagnetic ablative energy to a target tissue site.

BACKGROUND OF THE INVENTION

Various ablative therapies such as radio-frequency, microwave and laser ablation can be used to treat benign and cancerous tumors. In theory, such methods are intended to produce physiological and structural changes to cause cell necrosis or destruction of the selected target tissue. However in practice, there are numerous difficulties in the use of ablative procedures to treat cancerous tissue, these include (i) locating the target tissue, (ii) identifying or biopsying the disease state of the tumorous tissue (iii) distinguishing between diseased tissue versus healthy tissue, (iii) placing and maintaining the position of the ablation apparatus within the target tissue site, (iv) monitoring the progress of ablation including the developing ablation volume, (v) minimizing injury to adjacent critical structures (vi) assuring complete ablation of the tumor mass including assurance of a sufficient healthy tissue margin and (vii) assessing degree of the completed ablation. Current ablative therapies have not considered nor provided solutions to these problems. Thus, there is a need for an apparatus and method to address these difficulties and other unmet needs in performing ablative therapies for the treatment of cancer, tumors and other diseases.

SUMMARY OF THE INVENTION

An embodiment of the invention provides an impedance controlled tissue ablation apparatus and method that utilizes impedance determinations, such as localized tissue impedance to optimize the delivery of radio-frequency or other electromagnetic energy to a target tissue site and create larger ablation volumes using lower power levels and faster ablation times than currently possible with conventional RF tissue ablative technology. By lowering power levels required to produce an ablation volume the apparatus also provides the benefit of significantly reduced the risk of pad burns and other electroshock hazards associated with conventional RF ablation therapies. A related embodiment of the invention uses controlled infusion of electrolytic fluid at the tissue site to control and maintain tissue impedance at an optimal level for delivery of ablative energy.

Another embodiment of the invention provides an apparatus for detecting and treating tumors using localized impedance determination. The apparatus comprises an elongated delivery device that includes a lumen and is maneuverable in tissue. An impedance sensor array is deployable from the elongated delivery device and configured to be coupled to at least one of an electromagnetic energy source or a switching device. The impedance array includes a plurality of resilient members, at least one of the plurality being positionable in the elongated delivery device in a compacted state and deployable with curvature into tissue from the elongated delivery device in a deployed state. In the deployed state, the plurality of resilient members defines a sample volume. At least one of the plurality of resilient members includes a sensor and at least a portion of the impedance array is configured to sample tissue impedance through a plurality of conductive pathways. An energy delivery device is coupled to one of the sensor array, the resilient member or the elongated delivery device.

An embodiment of the invention provides a method for detecting and treating a tumor using tissue localized volumetric impedance determination. The method includes providing an impedance determination apparatus having a plurality of resilient members deployable with curvature and configured to sample tissue impedance through a plurality of conductive pathways. The apparatus is configured to be coupled to at least one of an energy delivery device, a power supply, a switching device or logic resources. The apparatus is then positioned at a selected tissue site and the impedance array deployed to define a sample volume. The impedance array is then utilized to make impedance determinations through a plurality of conductive pathways. Information from the impedance determinations is then utilized to determine a tissue condition of the sample volume. Energy is then delivered from the energy delivery device to ablate or necrose at least a portion of the tumor.

The apparatus can be configured to detect, locate and identify tumorous tissue at a selected tissue site using impedance determinations such as multi-pathway determined impedance, complex impedance and impedance vector determinations. For complex impedance embodiments, real and imaginary components of the impedance signal can be used to determine more refined bioelectric parameters such as interstitial and intracellular impedance and cell membrane capacitance that provide greater sensitivity and predictive power of cell necrosis or malignancy. Also, the apparatus can also be configured to utilize one or more impedance determinations to monitor a target tissue site and control the course of ablative therapy before during or after the delivery of ablative energy or other treatment to the tissue site. Accordingly, the apparatus can be configured to be used independently or in conjunction with another ablative apparatus such as an RF, microwave laser or other optical ablation apparatus. Further, the apparatus can be configured to utilize multi-path impedance determination to monitor two or more tissue volumes including a tumor volume, a developing ablation volume and an adjacent anatomical structure. Additional embodiments of the apparatus can also be configured to utilize impedance determinations such as complex, vector or locus impedance determinations to generate an image of a target tissue site and display the image to facilitate the location and monitoring of a tumor and/or ablation volume.

In the use, the apparatus would be positioned at selected tissue site previously imaged and found to contain a tumor or other tissue mass. The apparatus would be introduced and positioned at the tissue site using the elongated delivery device or an introducing device known in the art such as a trocar or endoscopic device. The impedance array would then be deployed and used to determine impedance including complex impedance and capacitance through one or more conductive pathways. This information could be analyzed by coupled logic resources and then utilized to locate the position of and borders of the tumor volume and/or identify the tumor or tissue type. Also, the information could be processed by the logic resources or other processing means to generate an image of the tissue site including the tumor volume which could utilize the locus of impedance as way to indicate the center of the tumor mass or otherwise visually enhance the detection and display of the tumor mass. This information could then be used to position the energy delivery to produce the desired ablation volume. Once the energy delivery device was positioned, the impedance array could then be utilized to monitor and/or control the delivery of ablative energy or therapy to the tumor volume including monitoring the size and shape of a developing ablation volume in relation to size and location of the tumor volume. This allows the medical practitioner to not only determine the degree to which the tumor volume has been ablated, but also allows for the control of the amount of healthy tissue margin around the tumor volume. Such control and related capability allows for the determination of a desired clinical endpoint. Further, it allows the practitioner to titrate or otherwise control the delivery of energy or other ablative therapy to control rate of growth of the ablation volume (and in turn the overall ablation time) as well as the final shape and size of the tumor volume. Multiple tissue volumes can be simultaneously monitored and compared to monitor progress of the ablation volume, assure uniform ablation or necrosis throughout the tumor or ablation volume and provide real time assurance that surrounding healthy tissues and structure were not injured. For example, tissue volumes at the center and one or more peripheries of the tumor mass could be simultaneously or near simultaneously monitored to assure uniform necrosis at these locations and hence throughout the tumor volume. Impedance determinations can be simultaneously or sequentially determined at multiple conductive pathways passing through the target volume (at convergent divergent and paths) to provide a higher confidence of uniform ablation by reducing the size of un-sampled zones within the target volume as well any directional bias of the measurements. The multiple conductive pathways can be selected electronically via a controllable switching device or manually by rotational, lateral or longitudinal movement of the impedance array within the target volume. In the former case, the user could program the conductive pathways via a coupled monitoring device and in the later the user could rotate, advance, retract or deflect the impedance array via the elongated delivery device or via a deployment, advancement or deflection device mechanically coupled to the impedance array or delivery device. In addition to real time impedance determination during the ablation process, measurements can also be taken post ablation at one or more pathways, (including pathways different than those used during inter-ablative monitoring) and compared to baseline measurements or an impedance database to provide a further indication of a complete ablation and/or clinical endpoint. Endpoints can also be determined based on ratios of intracellular to interstitial impedance as well a characteristic shape of the impedance or complex impedance curve including determinations of thresholds, slopes or inflection points.

Various aspects of the invention can also be directed to display impedance determinations in a variety of manners that are both user-friendly and easily discernible by the user/medical practitioner. In an embodiment, the loci of impedance of a sample volume or an impedance vector of the sample volume can be displayed as icons to facilitate tumor identification and positioning of an energy delivery or ablative device within the tumor mass. In related embodiments logic resource of the apparatus could be configured to use impedance vector measurements to determine the radial direction of the tumor from the impedance array or energy delivery device and display this information in the form of a directional or pointing icon.

BRIEF DESCRIPTION OF THE FIGURES

FIG. 4a illustrates an embodiment having a centrally positioned a return electrode surrounded by other electrodes; FIG. 4b illustrates an embodiment having the return electrode eccentrically positioned respect to other electrodes; FIG. 4c illustrates an embodiment having multiple and independently positionable impedance sensor arrays.

FIGS. 15a-15h are lateral views illustrating various configurations of the electrode including ring-like, ball, hemispherical, cylindrical, conical and needle-like.

FIG. 23b is a perspective view illustrating the key components of a tissue infusion ablation apparatus including configurations of the infusion device having multiple syringes and multi-channel tubing.

FIG. 23c is an expanded view of the distal portion of the apparatus of the embodiment of FIG. 23b illustrating the components of the distal tip as well as the conductive pathways of a device for measuring and controlling impedance.

DETAILED DESCRIPTION

Definitions

Figure 1:
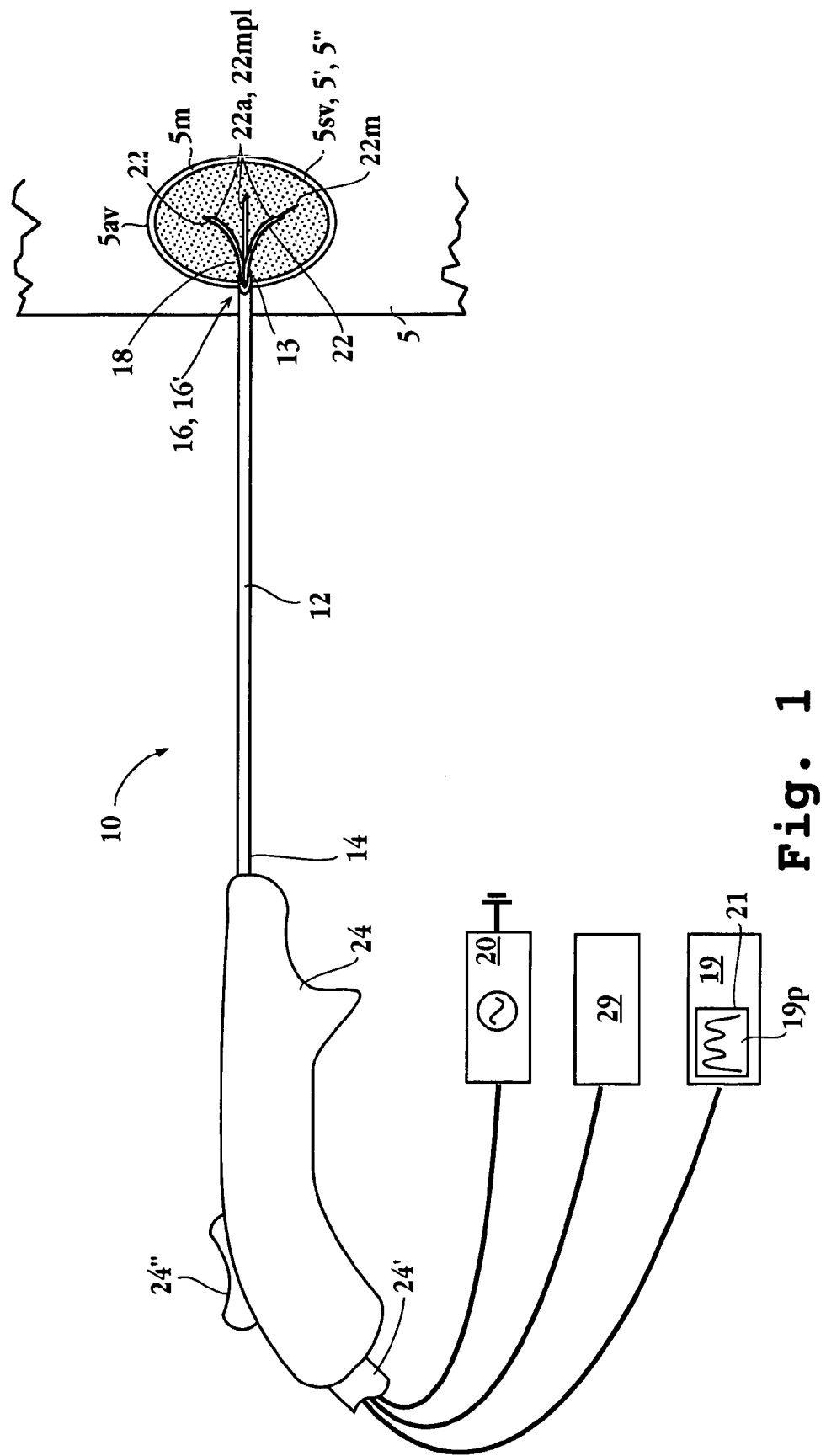
FIG. 1 is a lateral view illustrating the placement at a tissue site of an embodiment of an apparatus for detecting and treating tumors using localized impedance determination.

The terms below, as used herein, have the following meanings, unless indicated otherwise:

"Electrode", "resilient member" and "antenna" are interchangable and refer to a needle or wire for conducting energy to a tissue site. Electrodes may be passive, active or switchable between passive and active. Further, an electrode may be a ground pad electrode positionable at an exterior position on the patient.

A "sensing member" is a passive or active electrode for sensing an ablation parameter.

"Fluid delivery device" and "infusion device" are interchangable and refer to a device connected to, or including (i) a source of fluid to be infused, and (ii) one or more electrodes or the elongated delivery device for delivery of the fluid to a target tissue.

"Feedback control device", "control unit", "control resources", "feedback control system", and "controller" are interchangable and refer to a control capable of modulating an ablation parameter, i.e. power, temperature, infusion, etc. The control may be automatically or manually operated.

"Impedance measurement" or "impedance determination" are interchangable and refer to the calculation of impedance from a data source, i e. current sensor, voltage sensor, or power source, using any suitable calculation device or algorithm known in the art.

Embodiments of the present invention provide an apparatus and method for performing tissue characterization using localized impedance determination including complex impedance determination to locate and diagnose a tumor, accurately position an ablative apparatus, monitor the progress of an ablative treatment and determine clinical endpoints. Further these and other embodiments of the invention can be configured to measure and analyze bioelectric parameters with enhanced predictive power of cell metabolism along with associated images that allow for real time control of the ablative process awhile significantly reducing the risk of incomplete ablation or unwanted damage to critical anatomical structures. Each of the disclosed embodiments may be considered individually or in combination with other variations and aspects of the invention. The method and apparatus provided herein are useful in treating cancerous tumors in organs and tissue throughout the body including, but not limited to the liver, bone, breast, lung and brain. They are also useful and equally applicable to treatment of benign tumors, growths and otherwise abnormal or enlarged tissue that requires removal, resection or modification by surgical or minimally invasive means.

Localized monitoring of impedance provided in various aspects of the invention is particularly beneficial for use in the treatment of tumors and tumorous tissue by ablative therapies such as RF, microwave, laser and chemical ablation. These and related ablative therapies causes disruption of cell membranes resulting in impedance change in the interstitial fluid but only in the affected tissue with minimal or no changes to the surrounding tissue. Previous attempts to determine impedance using a full electrical circuit through the patients body had the drawback of not being able to detect tissue localized impedance by failing to consider the problems involved including the following:

(i) the signal is too small in relation to and/or mask out by the impedance of the entire impedance determination system including the conductive pathway through body the ground pad electrodes and associated wires;

(ii) the measurement was made too far away on the body from the desired tissue site and is thus again masked out; and (iii) the localized impedance was masked out by RF or other ablative energy signal delivered to the tissue. Embodiments of present invention provide solutions to these problems to detect localized impedance changes, particularly those changes occurring during an ablation procedure through the use of impedance arrays positioned at the target tissue to determine impedance including complex impedance and other bioelectric properties described herein.

A discussion will now be presented of impedance determination theory and impedance determination methods employed by embodiments of the invention. In order to determine tissue impedance or impedivity (which typically has units of impedance/cc of tissue at 20° C.) a current is applied across the tissue and the resulting voltages are measured. This current, known as the excitation current or excitation signal is relatively small in comparison to an ablative RF or other ablative current and hence results in no appreciable ablative effect. In various embodiments the excitation current can range from 0.01 ma to 100 amps with specific embodiments of 0.1, 1.0 and 10 amps which can be delivered in a continuous or pulsed fashion using a duty cycle. In various embodiments, the duty cycle can be in the range of 5 to 50% with a pulse duration of 10 to 200 ms. The average power delivered over the course of the duty cycle can be in the range of 0.1 to 10 watts. In these and related embodiments the excitation current source is used to measure voltage differences between two or more sites in a bipolar mode or one or more sites and a common ground. The known excitation current and measured voltage are then used to derive impedance using algorithms and methods described herein and/or known in the art.

Because different frequencies conduct differently through different tissue types some tissue is more or less conductive at certain frequencies. Accordingly, depending upon the tissue type or condition to be detected, the sensing or excitation signal can be varied or otherwise controlled to improve one or more of the sensitivity, accuracy, precision and resolution of an impedance determination. In various embodiments the excitation signal can be a mono-frequency or a multi-frequency signal and can be constant or variable. In an embodiment, improved signal resolution and thus more precise tissue analysis and characterization can be achieved by use of a multi-frequency excitation signal and/or an excitation signal varied across a broad range of frequencies. In various embodiments, this range of frequencies can be from about 1 Hz to about 1 MHz with specific embodiments of 0.5 Hz, 1, 5, 10, 25, 50, 100, 250, 500 and 750 kHz. Since the bioelectric distinctions (e.g. phase angle, impedance) between cancerous and healthy tissue can be the greatest at low frequencies such as 100 Hz, in exemplary embodiments measurements can be taken over a plurality of excitation frequencies below 100 Hz, with specific embodiments of 3, 4, 10 and 20 frequencies below 100 Hz. Other embodiment can be combine measurements below 100 Hz with those between 100 Hz to 5 kHz.

Further embodiments of the invention can be configured to determine impedance at different excitation frequencies (either concurrently or sequentially), to obtain more robust data and hence more refined clinical diagnostic information. Using these and other data and methods a plot of impedance versus frequency can be generated for a sampled tissue volume and analyzed to determine tissue type and tissue conditions of the sample volume as is more fully described herein.

Complex impedance includes both real and imaginary components, which reflect the phase shift between voltage and current (e.g. the voltage can lead or lag current depending on the electrical properties of the tissue). Various embodiments of the invention can be configured to record both the real and imaginary components of complex impedance. This provides the benefit of providing more comprehensive information on the tissue allowing analysis with a greater degree of accuracy, precision and resolution. These components can be determined by passing an excitation current through the target tissue and determining impedance and/or any phase shift between the current and voltage as the signal is conducted through the target tissue.

In related embodiments, real and imaginary components of impedance can be used to determine intracellular impedance, interstitial impedance and cell membrane capacitance. These three elements alone or in combination can be used to uniquely characterize and identify tissue type and condition with increased amounts of specificity. In an embodiment, the monitoring device, or other logic resources can be configured to utilize one or more of these three parameters (the "three parameters") to characterize an amount of ablation or progression of tissue ablation from an ablative treatment such as RF ablation or ablative method described herein. The characterization can be done by a software module resident within the monitoring device, power supply or coupled logic resources all described herein.

In specific embodiments, the thee parameters can be used to detect various physiologic indicators of ablation and cell necrosis including cell lysis, cell membrane swelling (indicated by an increase in membrane capacitance), cell membrane rupture (indicated by a sharp decrease in membrane capacitance), a decrease in extracellular fluid (indicated by an increase in intracellular impedance) and in increase in intracellular fluid (indicated by a decrease in extracellular fluid). Other parameters which can be calculated and used for detection and control purposes include the absolute value of the impedance or admittance, the phase of the impedance (e.g. the phase difference between the current and the voltage), the capacitance or a function of a combination of the impedance and admittance components.

Specific embodiments of the invention can be configured to detect and/or control for threshold increases or decreases in one or more of the three parameters (or other variables) including increases or decreases in the ranges of 1.1:1.0 to 100:1.0 with specific embodiments of 1.5:1.0, 2:1, 3:1, 4:1, 5:1, 10:1, 20:1 and 50:10. Related embodiments can be configured to detect and/or control for combinations of increases or decreases in the parameters including but not limited to a rise followed by a decrease in extracellular impedance, a decrease followed by an increase in intracellular impedance and an increase followed by a decrease in cell membrane capacitance. Other related embodiments can be configured to detect, monitor and control for changes in the slopes of the curves of one or more of the three parameters. Still other related embodiments can employ PID control methods known in the art utilizing combinations of proportional, integral or derivative changes in the three-parameter curves.

Embodiments of the invention can incorporate the three parameters into electronic algorithms/software programs which are configured to do one or more of the following: (i) control the delivery of power to the target tissue site, (ii) provide the medical practitioner with prompts and diagnostic information about the course of the ablation/treatment process, and (iii) provide the medical practitioner with an indication of a clinical endpoint.

Referring now to the drawings, FIG. 1 shows an embodiment of an impedance monitoring and treatment apparatus 10 configured to detect and treat a tumor mass 5" in a target tissue site 5' by sampling the impedance of the tissue mass and delivering energy or other ablative treatment to produce an ablation volume 5av. The apparatus can be configured to determine impedance, including complex impedance, before during and after an ablation so as to perform tissue identification at the target site, monitor the progress of an ablation procedure including the developing ablation volume and quantitatively determine a clinical endpoint for the procedure.

Figure 2:
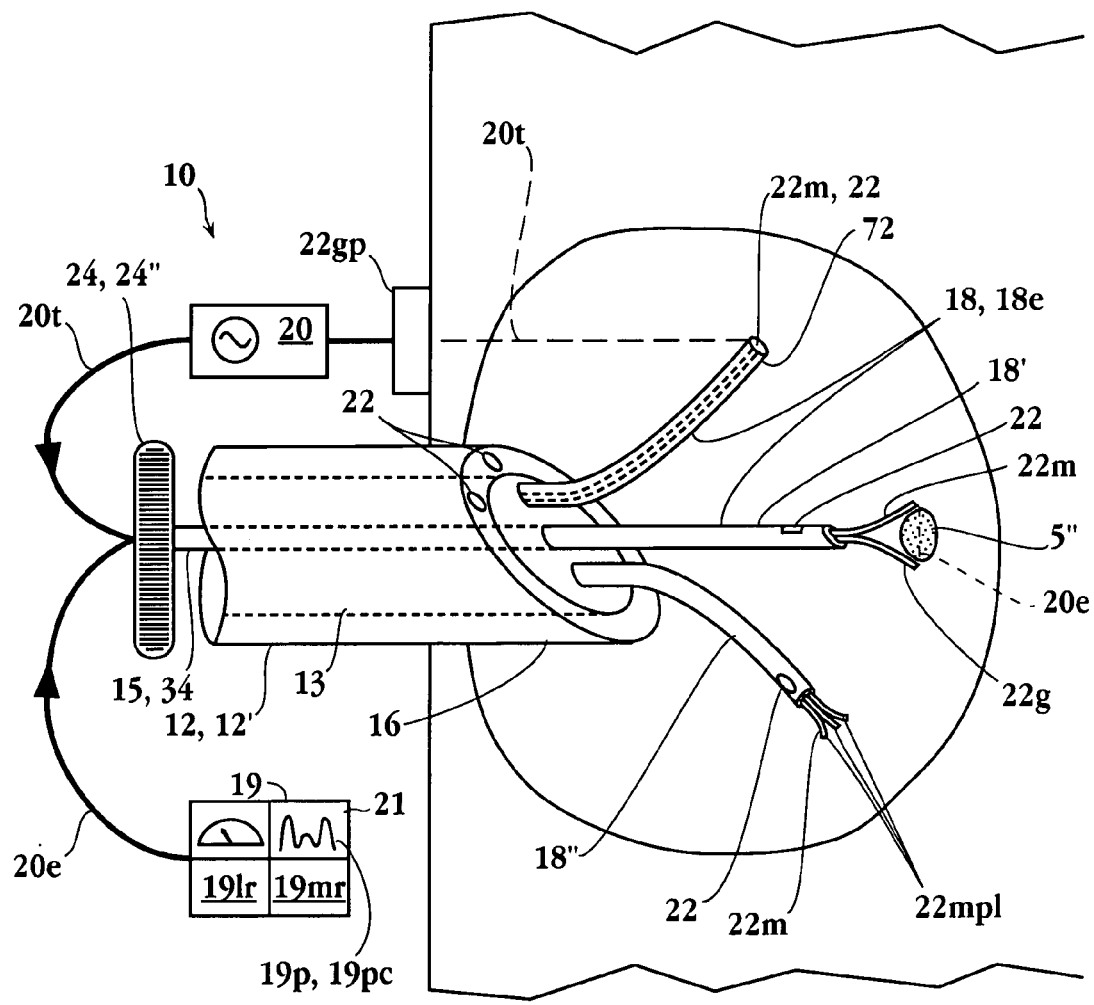
FIG. 2 is a lateral view illustrating the elements of an apparatus for detecting and treating tumors using impedance determination including an elongated delivery device, a sensor array, sensors, electrodes, energy delivery device and advancement member.

Referring now to FIGS. 1 and 2, an embodiment of impedance treatment apparatus 10 comprises an elongated member or introducer 12 having a lumen 13, a proximal portion 14, a distal end 16, one or more resilient members 18 positionable in the introducer lumen 13 and one or more sensors 22 disposed on members 18 or sensing members 22m positionabe in electrode lumen(s) 72 disposed within members 18. The electrode distal end may be sufficiently sharp to penetrate tissue including fibrous and/or encapsulated tumor masses, bone, cartilage and muscle. The introducer lumen 13 may extend over all or a portion of the length of introducer 12. Members 18 can comprise a plurality 18pl of resilient members 18 configured to be positionable in lumen 13 and advanceable in and out of distal end 16 by an advancement device 15 or advancement member or other means described herein. Resilient members 18 can be deployed with curvature from introducer 12 to collectively define a volume 5av in target tissue site 5'. In an embodiment all, or a portion, of one or more members 18 can be an energy delivery device or energy delivery member described herein. Energy delivery device 18e can be coupled to an energy source or power supply 20 and can also include one or more lumens 72.

Embodiments of the invention can be adapted, integrated otherwise applicable to a number of ablative therapies including, but not limited to, radio-frequency (RF) ablation, cryo-ablation, brachytherapy, alcohol tissue ablation, chemical ablation, microwave ablation, laser ablation, thermal ablation, electroporation ablation, conformal beam radiation ablation, standard radiation ablation, high intensity focused ultrasound ablation, photo-dynamic therapy ablation. These and related embodiments can comprise an energy delivery device and sensing device coupled to a power supply.

For ease of discussion, the energy delivery and sensing apparatus will be an RF based apparatus and power supply 20 will be a RF power supply; however, all other embodiments discussed herein are equally applicable. In and embodiment the RF power supply can be an RF generator configured to deliver a treatment current 20t for tissue ablation while simultaneously or near simultaneously (using a multiplexing/switching device) delivering a low power sensing or excitation signals 20e across at one or more frequencies for making complex impedance determinations and subsequent analysis of the target tissue. The excitation signal 20e can be delivered across a broad band of frequencies in the range of 1 to 1 MHz. In various embodiments, the excitation signal is delivered at a lower frequency then the treatment signal (typically 460+/−60 kHz). In an embodiment, the excitation signal is less than 400 kHz. In other embodiments, the sensing signal is in the range of 1 h to 100 kHz, with specific embodiments of 0.25, 0.5, 1, 5, 10, 25, 50 and 75 kHz. In alternative embodiments, the excitation signal is delivered at frequencies above the treatment frequency and thus can be greater than 520 kHz. Further the frequency and power differences between the excitation and treatment signals 20e and 20t can be monitored and set point controlled using circuitry and control algorithms known in the art. Also the frequency and power difference between the two signals can varied responsive to one or more electrical parameters to maximize the accuracy and precision of impedance determinations and reduce interference (e.g. bleed over) from the treatment signal 20t. These electrical parameters include but are not limited to impedance, treatment current, treatment frequency, excitation current and excitation frequency.

In various embodiments, introducer 12 can be flexible, articulated and steerable and can contain fiber optics (both illumination and imaging fibers), fluid and gas paths, and sensor and electronic cabling. In an embodiment introducer 12 can be configured to both pierce tissue and also be maneuverable within tissue. This can be achieved through the use of flexible portions coupled to a tissue piercing distal end 16 that can be a needle or trocar tip integral or joined to introducer 12. Introducer 12 can be sufficiently flexible to move in any desired direction through tissue to a desired tissue site 5'. In related embodiments, introducer 12 is sufficiently flexible to reverse its direction of travel and move in direction back upon itself. This can be achieved through the use of flexible materials and/or deflecting mechanisms described herein. Also, introducer 12 can be coupled at its proximal end to a handle 24 or handpiece 24. Handpiece 24 can be detachable and can include ports 24' and actuators 24".

One or more sensors 22 can be coupled to introducer 12, resilient members 18 or energy delivery device 18e. In an embodiment, sensors 22 can comprise one or more sensing members 22m that can be positionable within lumens 72 of members 18 and configured to be advanceable in and out of individual members 18 or can be coupled to an exterior of resilient member 18. Sensing members 22m can comprise a plurality of members 22mpl positioned in multiple resilient members 18. Also, apparatus 10 can also have sensors 22 disposed along elongated member 12 and other locations outside of the target tissue site for measurement and determination of the total impedance across the full electrical circuit between the terminals of power supply 20 (i.e. through the patient's body and into the ground pad). The total impedance can be monitored and otherwise utilized to improve the accuracy and precision of the localized impedance determination from the target site.

Impedance sensing members 22m, or sensors 22 coupled to resilient members 18 can be deployed independently or simultaneously to enable probing of target tissue 5' in multiple locations so as to determine impedance in multiple locations and/or through multiple conductive pathways 22cp. Deployment of impedance sensing member 22m or sensors 22 can be controlled such that telemetry can be used with impedance feedback to identify tissue types and map the topography of tissue masses, tumors or tissue structures.

Impedance sensing members 22m can also be deployed with curvature from members 18 to collectively define a volume 5sv (also called sample volume 5sv) that is volumetrically sampled by sensing member plurality 22mpl. Collectively, the plurality 22mp of deployed impedance sensing members 22m or plurality 18pl of deployed resilient members 18 with coupled sensors 22 can comprise a three-dimensional or volumetric impedance sensor array 22a. By having sensors 22 in multiple locations and planes sensor array 22a is configured to volumetrically sample (e.g. sample in multiple locations and through multiple conductive pathways) tissue within target tissue site 5' including tumor mass 5". Sensor array 22a is further configured to be able to simultaneously sample tissue at multiple locations within volume 5sv or tissue site 5' to perform one or more of the following: (i) locate the position of the tumor mass 5", (ii) discern the position or deployment distance of the energy delivery devices 18, (iii) monitor the developing ablation volume, (iv) perform tissue sensing identification by comparing signals between two or more sites (e.g. known healthy tissue and suspected diseased tissue). In various embodiments sensor array 22a and/or member plurality 18pl can be configured to define a variety of shapes for sample volumes 5sv including, but not limited to, a hemisphere, a sphere, an oval, a cone, pyramidal, a polyhedron or a tetrahedron.

Figure 3A:
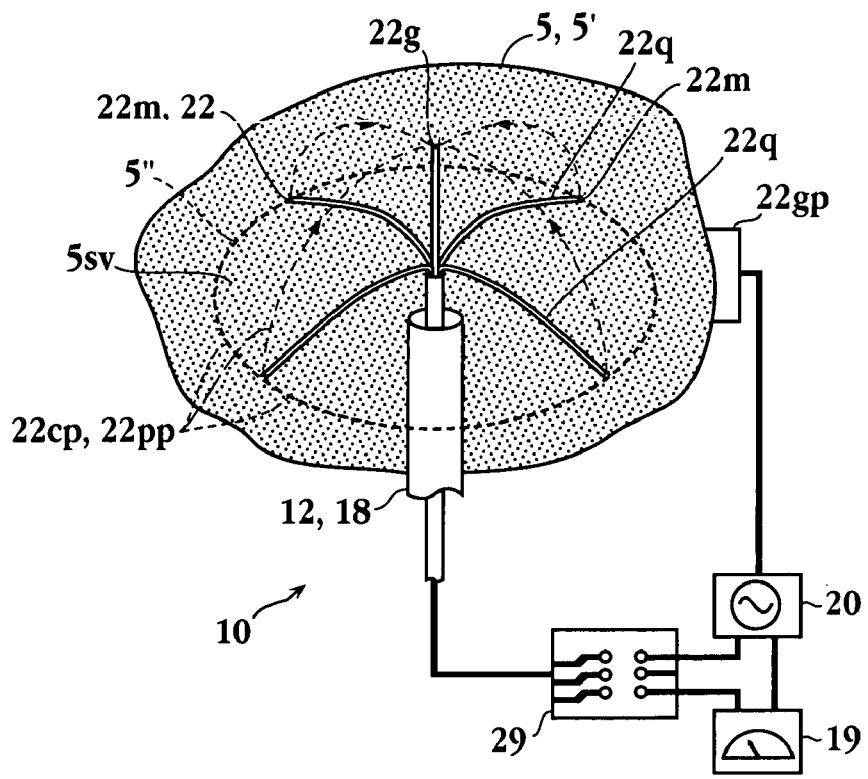
FIG. 3a is a schematic view of an embodiment of the impedance sensor array configured to determine impedance of a tissue volume via a plurality of selectable conductive pathways.

Each resilient member 18 can have one or more impedance sensing members 22m and/or sensors 22 that can be arranged in a variety of configurations to perform one or more desired functions described herein (e.g. tissue identification, ablative monitoring etc.). Referring now to FIG. 3a, sensing members 22m can be configured to determine impedance in either bipolar between two or more members 22m or a mono-polar mode between one or more selected members 22 and a common ground such as a ground electrode or ground pad electrode. Switching between the two modes can be controlled by logic resources and/or a switching or device 29 coupled to or integral with an impedance monitoring device 19 or power supply 20. Further, switching device 29 can be configured to allow the user to define and select one or more conductive pathways 22cp to determine impedance. In use, these and related embodiments allow the user to select any number of conductive pathways and in a pattern 22pp that circumscribe or otherwise defines a sample volume 5sv of interest. Also the use of switching device 29 in these embodiments allows the user to determine impedance simultaneously or sequentially through the selected pathways. Further switching device 29 and/or apparatus 10 can be so configured to allow the user to dynamically change or switch between pathways to do one or more of the following:

(i) change the number of pathways through a selected sample volume allowing increased signal resolution and statistical confidence of predicted tissue conditions;

(ii) change the angle between two or more conductive pathways; and (iii) change the size of the sample volume (iv); switch between a first and second sample volume; and (v) compare two or sample volumes simultaneously.

Figure 3B:
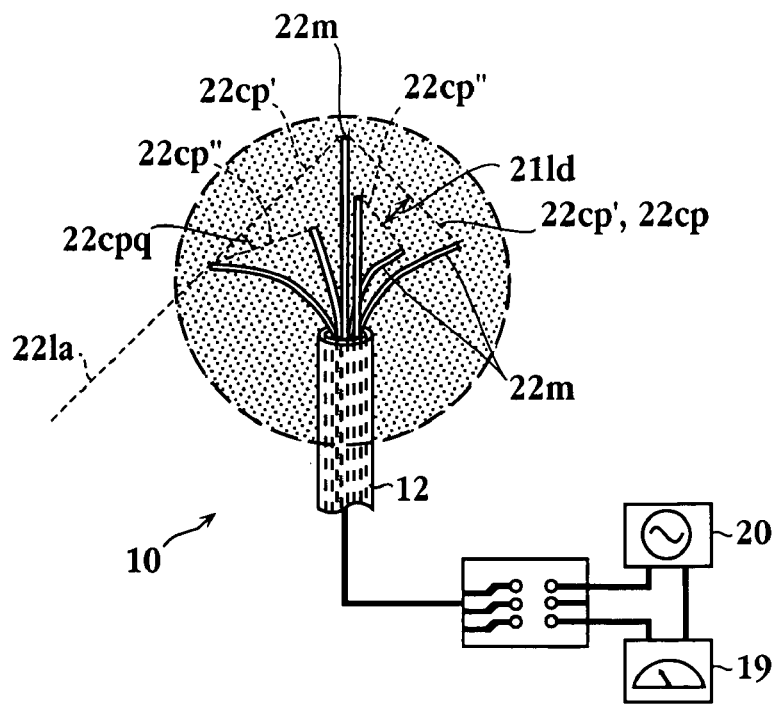
FIG. 3b is a schematic view illustrating of an embodiment of the apparatus illustrating the use of primary and secondary conductive pathways and conductive pathway angle.

In an embodiment shown in FIG. 3b, conductive pathways 22cp can include a primary pathway(s) and an alternative pathway(s). The alternative pathway can be at a selectable angle from the primary pathway and can share points in common with the primary pathway. Suitable angles include the range of 1 to 360° with particular embodiments of 30, 45, 90 and 270° from a lateral axis 22la of the primary pathway. Alternatively, the alternative conductive pathway can share one or more points in common with the original pathway or be parallel with the original pathway but offset a selectable lateral distance 22ld. Also repetitive scans of impedance including sweep scans and sequential sweep scans (e.g. sequentially sampling from one side of a sample volume to the other, similar to radar) can be made through one or more selected conductive pathway of a selected sample volume to monitor the time course of ablation as well obtain improved signal to noise ratios and signal resolution for image analysis.

Changing the angle and/or lateral offset of the conductive pathway used to determine impedance can be accomplished through a variety of means including but not limited to: (i) selectively switching sensors 22 or sensing elements 22m off and on (ii) selectively switching sensing elements 22m from a monopolar mode to a bipolar mode and visa versa, (for RF embodiments) using switching device 29 (iii) configuring the probe array to be rotatable and/or deflectable, and (iv) the use and/or deployment of a second array either on the same or different device. Switching can be accomplished through the use of a switching or multiplexing device 29 which can be programmable or controlled by logic resources 19lr described herein.

In one embodiment the data from alternative conductive pathways or group of pathways can be integrated with measurements from the primary conductive pathways for analysis and imaging purpose or in an alternative embodiment can be analyzed and displayed separately allowing for a comparison of both measurement and image from the primary and alternative group of pathways. The benefit of the former is a more representative and uniform sample of impedance and the later the ability to detect for uniformities of impedance within the sample volume.

In use, such embodiments allow the medical practitioner to sample or image a larger tissue volume than single pathway sampling, sample multiple tissue volumes including simultaneous sampling without having to reposition the apparatus or impedance array. This capability reduces procedure time generally enhances the usability of the apparatus. Further, such embodiments also provides a more accurate and representative signal of the target tissue volume by selecting conductive pathways to control the shape and size of the sample volume to sample only the area of interest eliminating any potential masking or undesired impedance contribution from surrounding non-target tissue. Also the ability to switch the angle of the pathway eliminates or reduces any directional bias in the impedance determinations. Finally, by virtue of having a larger and volume distributed sample size for a given volume of tissue, the use of multiple conductive pathway impedance determinations provides a more representative measurement of impedance for the selected volume improving the accuracy and precision of the impedance determination as well as improving signal and image resolution in one or all three dimensions.

Figure 4A:
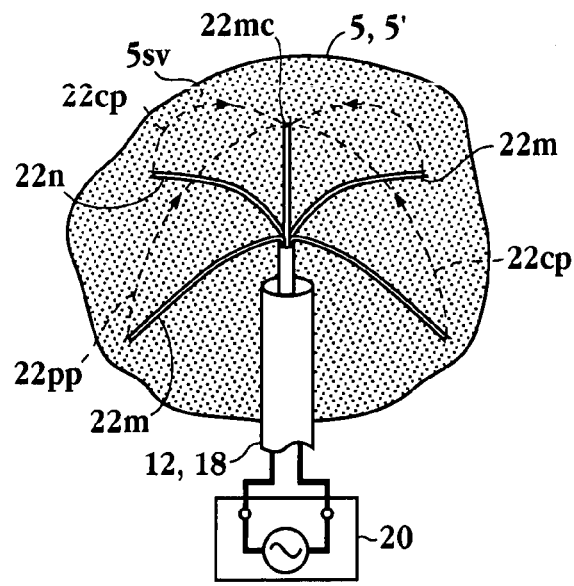
FIGS. 4a-4c are perspective views illustrating various arrangements of the emitting and detecting members.
Figure 4B:
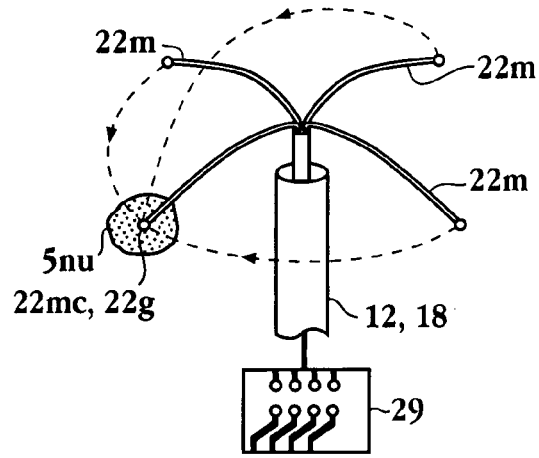
Figure 4C:
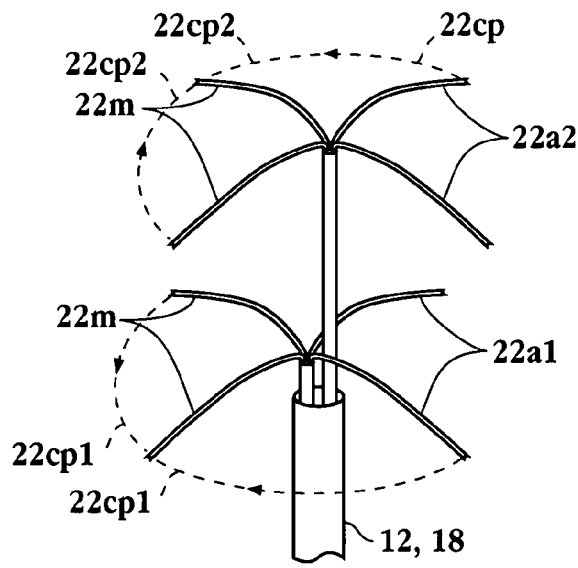

Referring now to FIGS. 4a-4c in various embodiments, impedance sensing members 22m can be arranged in arrays 22a having a variety of geometric arrangements and relationships so as to electrically sample different volumes of tissue 5sv using different conductive pathways 22cp. Such embodiments provide the benefit of improved acquisition, accuracy and analysis of the impedance signal 19p from a given sample volume 5sv to compensate for signal hysteresis, noise (due to energy delivery etc.) directional bias or other error. They also provide the benefit of simultaneous sampling and comparison of two or more tissue volumes to perform tissue identifications.

Referring now to FIGS. 4a-4c, conductive pathways 22cp can have a variety of configuration and orientations all selectable by the user. In an embodiment the conductive pathways 22cp can be evenly distributed or spaced within the sample volume 5sv. This can be achieved by either the configuration of the members 22m, through the use of switching device 29 or a combination of both. Alternatively, the conductive pathways can be aligned with respect to one or more sensing members 22m, the introducer or the tumor volume 5" itself. In an embodiment shown in FIG. 4a, one member 22mc can be positioned at the center of tissue volume 5sv with other members 22m positioned in a surrounding relationship so excitation current travels in a plurality 22pp of conductive pathways 22cp to and from the center of the sample volume 5sv to the outlying impedance sensor members 22m. In use, this configuration results in an impedance determination for the sample volume 5sv which is an average of the individual impedance for each conductive pathway providing the benefit of a more a statistically representative sample of impedance for a selected tissue volume than provided by a single pathway alone. Members 22m can be collectively coupled to a positive terminal of power supply 20 with member 22m configured as a return electrode and coupled to a return terminal of power supply 20.

In a related embodiment shown in FIG. 4b, member 22m can be eccentrically positioned with respect to members 22m and/or positioned on the periphery of a sample volume defined by members 22m. Again, this embodiment provides the benefit of an average and more representative impedance determination for the sample volume. However, this configuration also provides the benefit of being able to more readily detect and locate non-uniformities in impedance and hence tissue properties occurring on the boundaries or otherwise non centered portions of the tissue volume. Use of switching device 29 allows for the dynamic switching of any of the sensing members 22m to a return electrode to more readily detect the location of a potential non-uniformity within the sample volume by rapidly scanning different portions of the periphery of the volume.

Alternatively as shown FIG. 4c, members 22m can comprise a first array (such as perpendicular array) and a second array. The first array can be rotated to obtain different conductive paths to the second array so as to sample different tissue volumes and/or provide multiple samplings of the same volume (via different conductive paths) to improve accuracy and precision of the measurement and reduce noise. In use, this embodiment also allows detection of incomplete ablation by comparing a determined impedance from a first group of conductive pathways 22cp1 defined by first array 22a1 to a second group of conductive pathways 22cp2 defined by second array 22a2.

Figure 5:
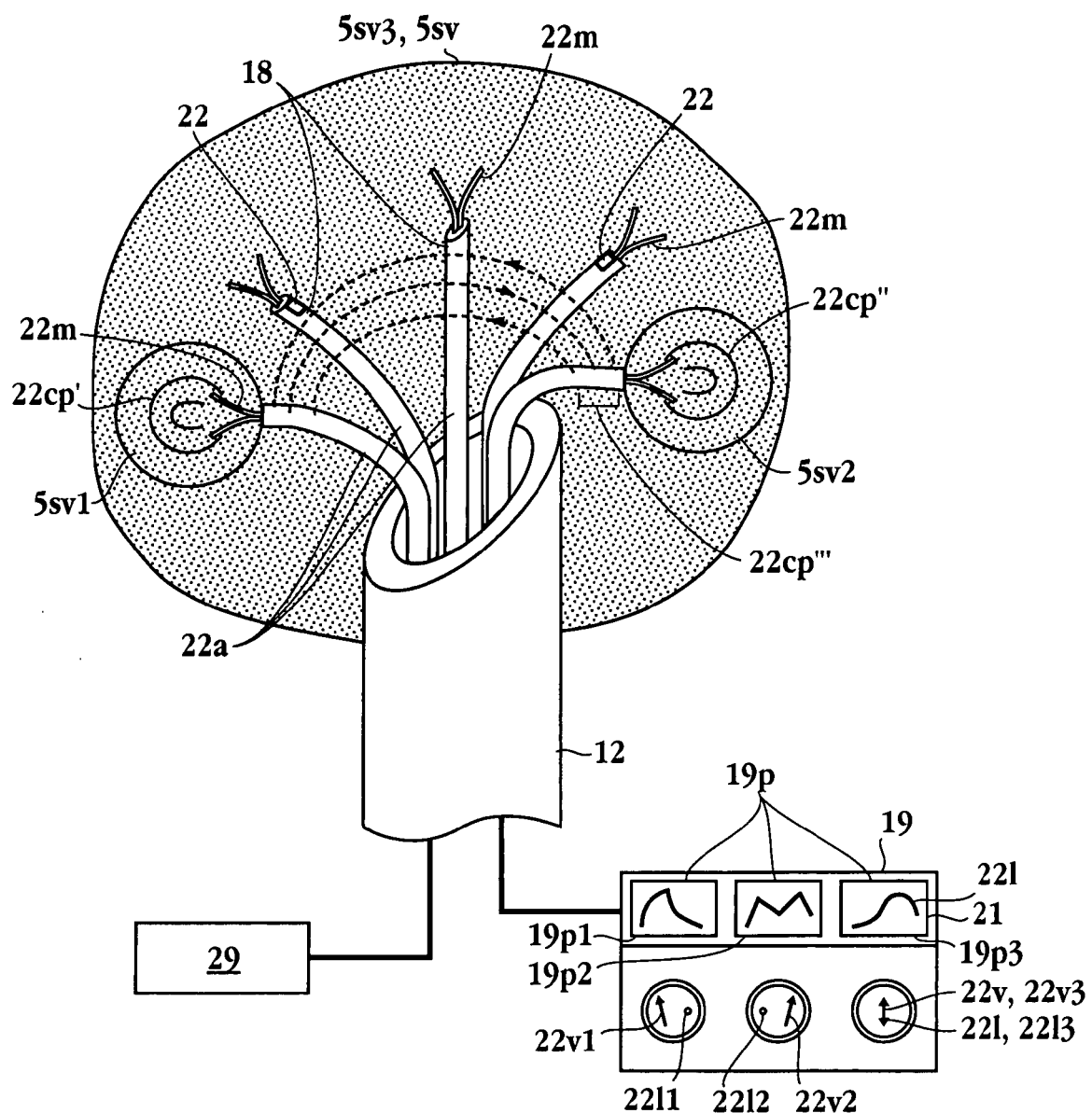
FIG. 5 is a perspective view illustrating the use of multiple groups of conductive pathways to sample multiple tissue volumes in an embodiment of the invention as well as determine impedance vectors and loci of impedance for each sample volume.

In various embodiments apparatus 10 can be configured to simultaneously sample different locations within target tissue site 5' utilizing switching device or multiplexer 29 or other switching means described herein or known in the art. In an embodiment shown in FIG. 5 a first group of selected conductive pathways 22cp' can be used to sample a local first volume 5sv1 and a second group of selected conductive pathways 22cp" can selected to do so for a second volume 5sv2 and a third group of selected conductive pathways 22cp'; can be so selected to do so for a larger or global sample volume 5sv3 defined or circumscribed by multiple sensor tipped members 18 or sensing members 22m. Each sample volume results in a separate impedance profile 19p. Thus sample volumes 5sv1, 5sv2 and 5sv3 produce impedance profiles 19s1, 19s2 and 19s3 respectively, all or portion of which can be compared to one another or a database of impedance profiles 19db using comparison/pattern recognition algorithms of module 19m other software or computational means. In a related embodiment the determined impedance signal for each sample volume can integrated or otherwise analyzed by module 19m or other computational means to determine an impedance vector 22v and loci of impedance 22i for each respective sample volume (e.g. impedance vectors 22v1, 22v2, 22v3; and impedance loci 22/1, 22/2 and 22/3).

Figure 6:
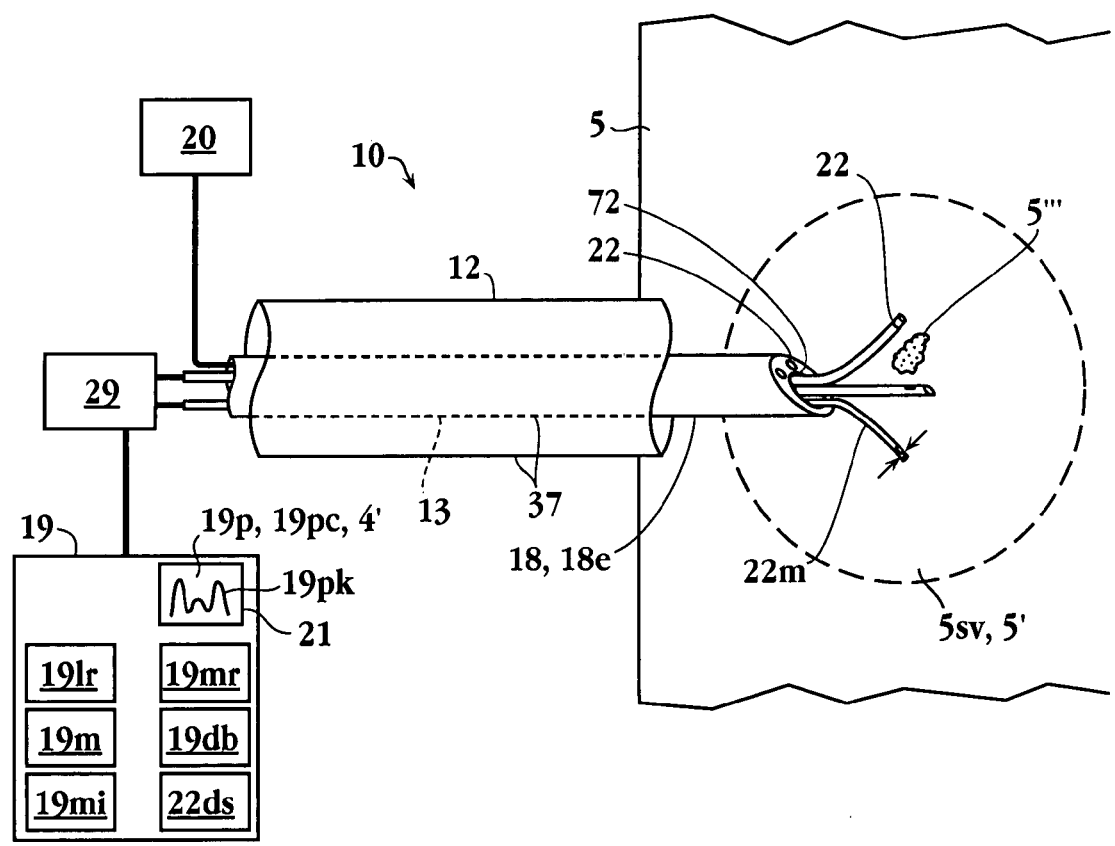
FIG. 6 is a perspective view illustrating an embodiment of an apparatus for detecting and treating tumors including an impedance monitoring device having memory resource and logic resources including software modules to analyze impedance data and generate impedance profiles and images.
Figure 7A:
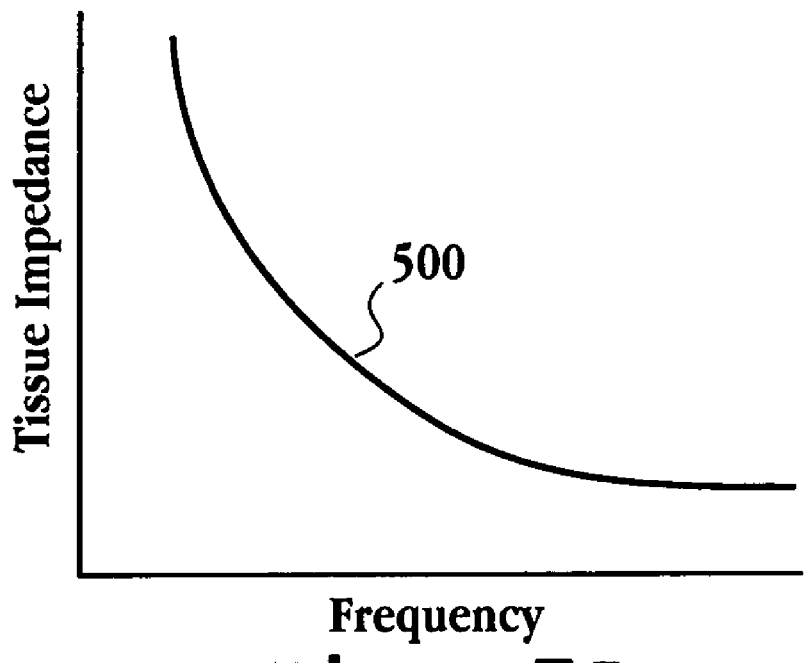
FIG. 7a is a plot of tissue impedance curve illustrating the frequency dependency of impedance.
Figure 7B:
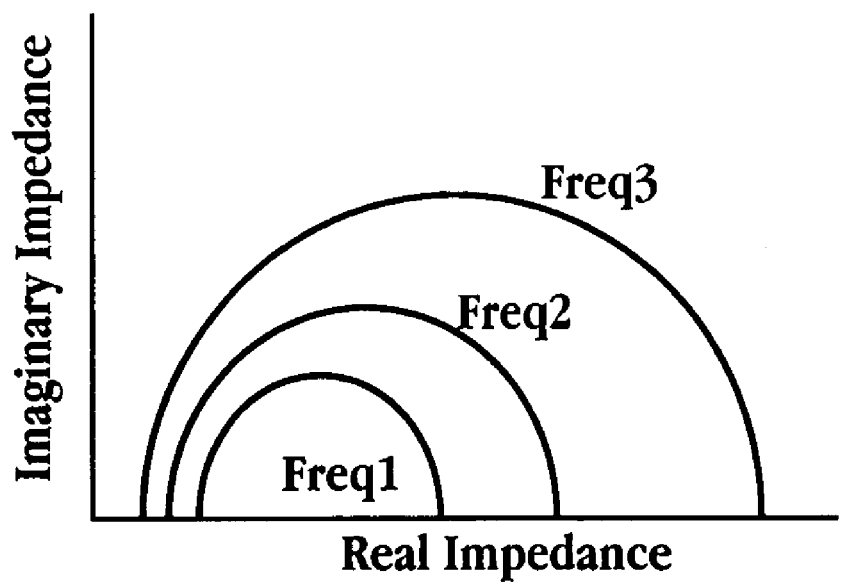
FIG. 7b is a plot of tissue complex impedance curves illustrating the frequency dependency of complex impedance.

Referring now to FIG. 6, in an embodiment one or more sensors 22 or sensing members 22m can be coupled to an impedance determination and monitoring device 19. Monitoring device 19 includes circuitry described herein to measure voltage from the excitation current and subsequently calculate impedance. Further monitoring device 19 can also be configured to measure, calculate and record complex impedance, an impedance profile 19p and a complex impedance profile 19pc resulting from various tissue bioelectric properties including, impedance conductance, capacitance, etc. In an embodiment, monitoring device 19 can include logic resources 19lr such as a microprocessor and memory resources 19mr such as RAM or DRAM chip configured to analyze, store and display tissue impedance profile 19p and/or other bio-electric information derived from sensing member 22m and/or sensing array 22a. Impedance monitoring device 19 can also be coupled to a display device 21 so as to display real time or stored impedance profiles images and other data generated by impedance monitoring device 19. Examples of display devices 21 include cathode ray tubes (CRTs), liquid crystal displays, plasma displays, flat panel displays and the like. Display device 21 can also be incorporated in an external computer coupled to impedance monitoring device 19.

In various embodiments, impedance monitoring device 19 or power supply 20 can be equipped with a number of feature including but not limited to the following:

(i) memory resources containing a database of characteristic impedance profiles;

(ii) a readout window for the impedance based diagnosis of tissue type and/or condition;

(iii) artificial intelligence algorithms/programming enabling the generator to learn from newly acquired impedance scans;

(iv) ability for the user to enter and teach the generator the correct tissue type and condition based on biopsy or pathology data;

(v) ability to sense impedance on multiple frequencies simultaneously to improve speed, accuracy, and reduce effects of interference;

(vi) ability to work with non-invasive pads (like electro-physiology pads) for measurement of complex impedance and performing targeted tissue assessment non-invasively;

(vii) ability to monitor a reference signal and/or basic patient electro-physiological conditions for baseline comparisons with impedance readings and as additional information for the user; and (viii) programming to utilize the reference signal or signal to account for hysteresis, signal noise, cross talk and other signal interference using digital subtraction, suppression and other signal processing methods known in the art and thus improve a signal to noise ratio, signal sensitivity or resolution.

In various embodiments, apparatus 10 along with impedance monitoring device 19 can be configured to perform tissue identification, differentiation, ablation monitoring and mapping of tissue masses and structures. In specific embodiments, monitoring device 19 is configured to perform a tissue identification function using impedance information derived from sensors 22, sensing members 22*m* or array 22*a*. A discussion will now be presented on the background of tissue monitoring and identification using impedance determination. Owing to variations in composition and morphology various tissue types have different electrical properties (e.g. conductance, inductance, capacitance etc) and therefore conduct electrical energy differently particularly at certain frequencies. For example cancerous tissue will typically have a significantly higher phase than the health tissue, particularly at low frequencies. These difference in electrical properties, particular conductance result, in a characteristic impedance profile 19*p* for a given tissue type or condition when the tissue is exposed to an excitation current at one or more specific frequencies. Impedance profile 19*p* can have one or more peaks, curves and other shapes that serve as a fingerprint of the tissue type or tissue condition. Accordingly by analyzing the impedance profile 19*p* and matching peaks, curve shapes, thresholds etc, profile 19*p* can be utilized by embodiments of the invention to identify tissue types and conditions such as malignancy, vascularity, necrosis, thermal injury etc. Related conditions that can also be identified using this approach include abnormally mutated tissue, abnormally dividing tissue or hypoxic tissue.

Further, many tissue types including cancerous tissue such as metastatic tissue, will have a signature profile 19*p* that can be readily identified and matched to a database of profiles using pattern recognition techniques or algorithms known in the art. Accordingly, apparatus 10 can include electronic algorithms or software modules 19*m* resident in logic resources 19*lr* of monitoring device 19 or microprocessor 339 that are configured to analyze an impedance profile 19*p* including real and imaginary components and perform tissue identification and/or tissue differentiation between one or more sampled volumes 5*sv*. Modules 19*m* can include pattern recognition algorithms, curve fitting, fuzzy logic or other numerical methods known in the art. Also in an embodiment, modules 19*m* can be configured to compare profile 19*p* to a database of profiles 19*db* stored in memory resources 19*mr* an use curve fitting or other numerical methods known in the art to provide and display a correlation coefficient or statistic (e.g. p value) indicative of the probability of a match to a given tissue type or condition.

In various embodiments the impedance and other bioelectric properties that can be analyzed to determine a tissue type or condition include, but are not limited to complex impedance (real and imaginary components), extracellular impedance, intracellular impedance, interstitial impedance, cell membrane capacitance, intracellular capacitance. In an embodiment, monitoring device 19 can be configured to analyze only selected frequencies of an impedance profile or other bioelectric property measurement that are known to identify or correlate to selected tissue characteristics, rather than analyzing the full frequency spectrum of the profile. Such frequencies can be selected from a pre-existing database or determined in vivo using swept frequency methods described herein. This approach presents the advantage of faster signal processing times, allowing a faster tissue assessment and diagnosis using fewer computational resources. In turn this enables the size, power requirements and complexity of the control and display instrumentation to be reduced.

Referring now to FIGS. 7-10, in related embodiments apparatus 10 and monitoring device 19 can be configured to utilize complex impedance curves to identify and characterize different tissue types and conditions. Accordingly, monitoring device 19 can be configured to measure generate and display curves or profiles 19*pc* of complex impedance. Curves can be both two-dimensional and three-dimensional. For two-dimensional plots the x-axis can be the real component and the y-axis the imaginary component while three-dimensional plots can include an axis for time or frequency. This can be accomplished via algorithms within modules 19*m* that receive input from impedance array 22*a*, perform complex impedance calculations known in the art and curve fitting or transform functions described herein and subsequently output an impedance profile 19*p* that is displayed on display device 21. As shown in FIGS. 7*a* and 7*b*, because tissue conducts differently at frequencies, measurements made across a range of excitation frequencies results in an impedance frequency response curve 500 (FIG. 7*a*) or a series of complex impedance frequency response curves (FIG. 7*b*). Using either of the frequency response curves from FIG. 7*a* or 7*b*, a particular frequency can be selected for subsequent impedance complex impedance determinations and analysis which has the greatest sensitivity for a given tissue type or condition and/or results in a complex impedance curve having the greatest predictive value for the desired tissue type or condition. The selection can done using methods described herein or by calibration against a set of in vitro standards representative of the desired tissue condition, by visual determination/estimation of the user or a combination of both.

Figure 8A:
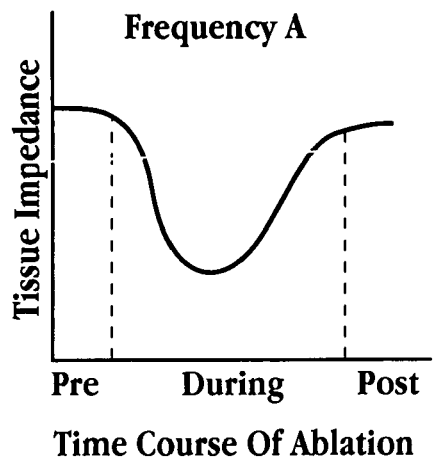
FIGS. 8a-8d are plots of impedance curves illustrating the use of multiple frequency impedance curves to monitor the time course of an ablation.
Figure 8B:
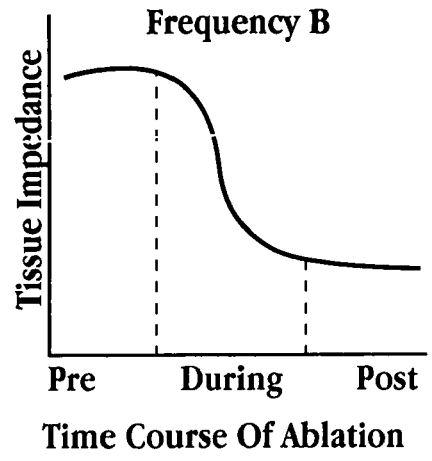
Figure 8C:
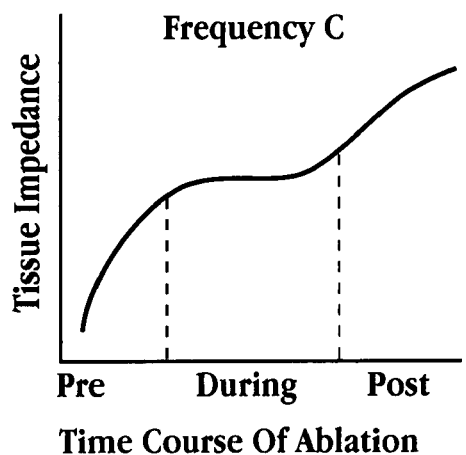
Figure 8D:
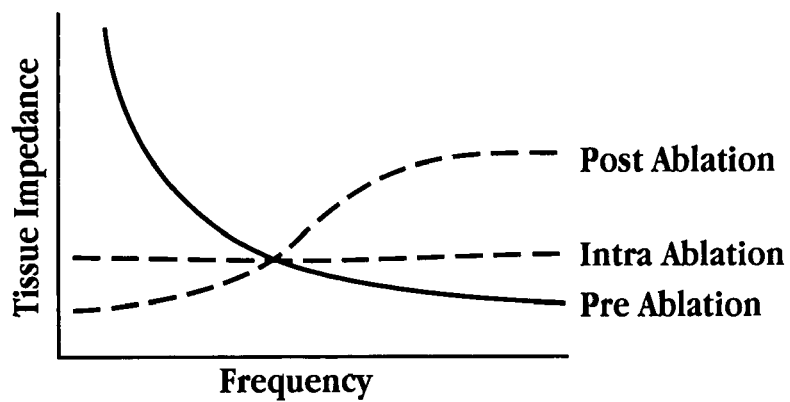
Figure 8E:
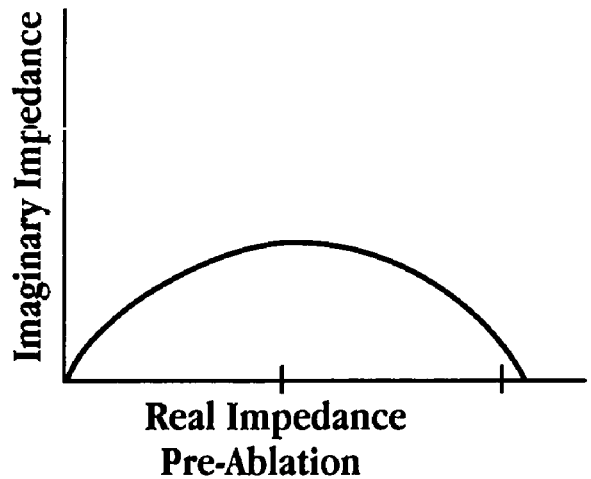
FIGS. 8e-8g are plots of complex impedance curves (imaginary vs. real values) illustrating the use of complex impedance curves to monitor the time course of an ablation.
Figure 8F:
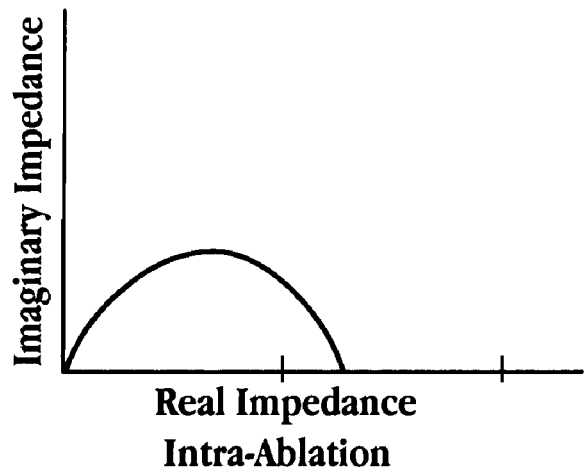
Figure 8G:
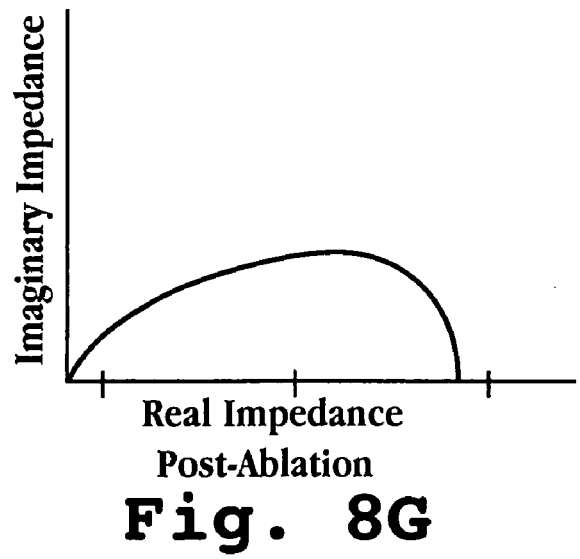

As shown in FIGS. 8*a*-8*c*, in an embodiment, the course of an ablation can be monitored using impedance determinations made at multiple frequencies. The impedance at some frequencies will rise, fall or do both over the time course of the ablation. By combining impedance data from multiple curves the overall predictive value of the measurements for an ablation event or endpoint is greatly increased. Accordingly, using differential diagnosis methodology an ablation monitoring algorithm or module can be configured to look for impedance characteristic curve shapes, slopes threshold, etc. in two or more impedance curves made at different frequencies as a predictor of an ablation endpoint. Such information can be used to provide a more reliable indicator of clinical endpoint as well monitor and titrate the delivery of ablative energy or ablative therapy to the requirements. Similarly, as shown in FIG. 8*d*, differences in the impedance-frequency spectrum, pre-, inter- and post-ablation can also be also used to monitor and evaluate the ablation process.

Figure 9A:
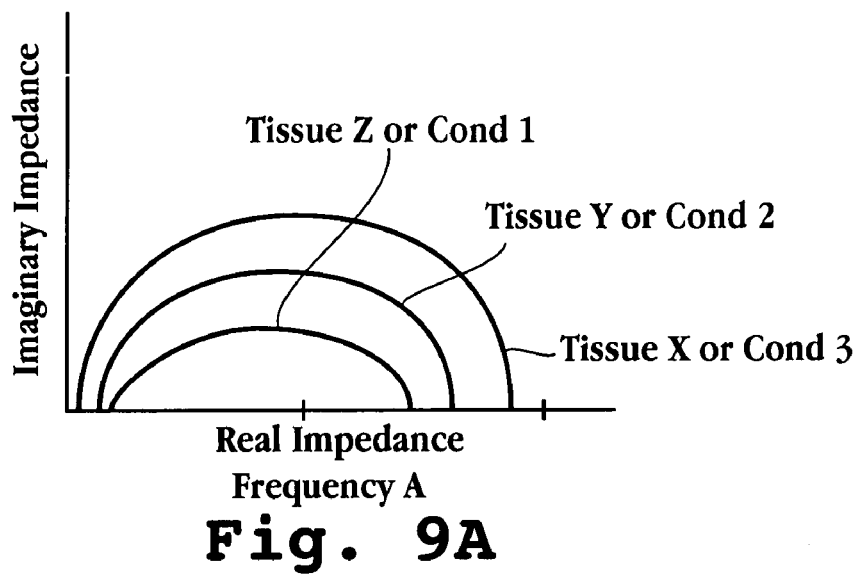
FIGS. 9a-9c are plots of complex impedance curves illustrating the use of complex impedance curves to identify tissue type or condition.
Figure 9B:
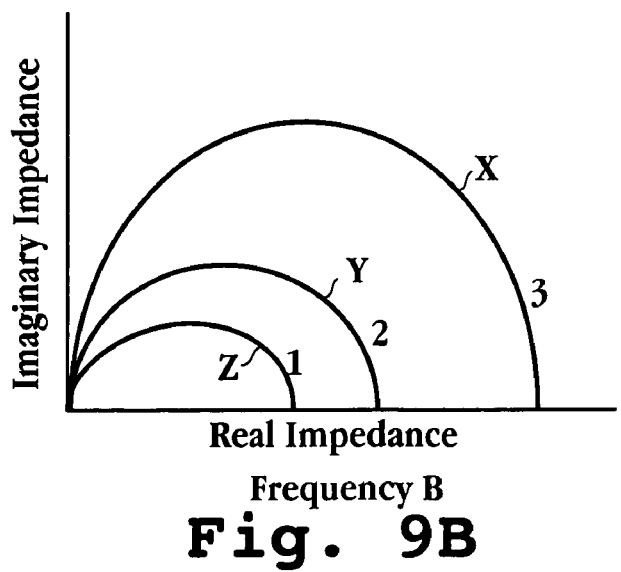
Figure 9C:
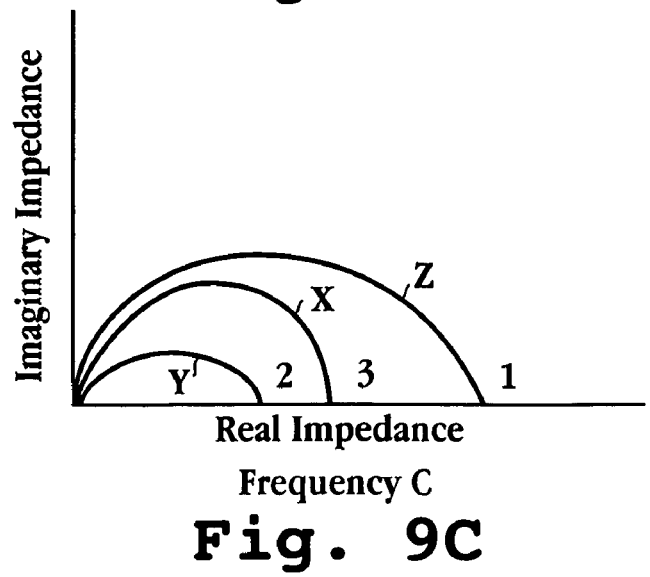
Figure 10:
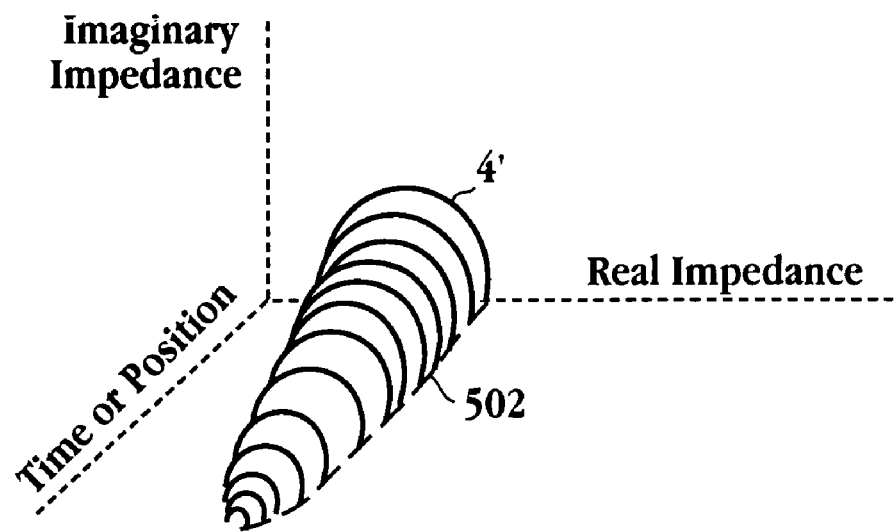
FIG. 10 is a plot of spectral signal intensity verses time for a sample volume of ablating tissue illustrating quantitative determinants of an ablation endpoint.

In related embodiments shown in 8*e*-8*g*, complex impedance curves can be used to monitor and assess the ablation process including determination of clinical endpoints as described herein. Further as shown in FIGS. 9*a*-9*c*, the apparatus can be configured to utilize complex impedance curves to identify and characterize different tissue types, tumors etc. Related embodiments can be configured to generate and display three-dimensional plots of complex impedance utilizing time and or position as the third axis. For positional 3-D plots the locus of impedance 502 can be calculated and graphically displayed as is shown in FIG. 10 or in another graphical format known in the arts including 2-D. Also, the impedance locus can be utilized to characterize the ablation process and can be used to perform vector analysis of RF or microwave current or other ablative energy vector, (e.g. the magnitude and direction of the ablative energy), as well as vector analysis of physiologic indicators of cell necrosis, such as changes in interstitial conductivity. In various embodiments, the impedance locus can be utilized to facilitate location and display of a tumor volume, ablation volume, or other desired tissue mass or volume at the target tissue site. The generation and display of the impedance locus 5li (in 2-D or 3-D) can be configured to provide the medical practitioner an easily discernable visual cue as to the location, size or movement of the ablation, tumor or other selected tissue volume.

In addition to identifying tissue types, the monitoring device, along with the impedance sensing array(s), can also be employed to monitor in real time the progression of an ablative procedure including the progression of an ablation volume resulting from the delivery of energy to a target tissue volume. This reduces damage to tissue surrounding the targeted mass to be ablated. By monitoring the impedance at various points within and outside of the interior of a tissue site, a determination of the selected tissue mass periphery can be made, as well as a determination of when cell necrosis is complete. If at any time sensor results determine that an impedance level or ablation endpoint has been met or exceeded, then an appropriate feedback signal is inputted to power source which then stops or otherwise adjust the levels of ablative energy delivered to the electrodes. The target tissue site can also be probed and interrogated by the sensor array after the completion of ablation to confirm that ablation is complete for the entire desired volume ablation volume. By probing the ablated region with the sensor array, the three-dimensional volume of the ablation can be assessed and the margin of ablated healthy tissue beyond the tumor mass can also be measured.

Figure 11:
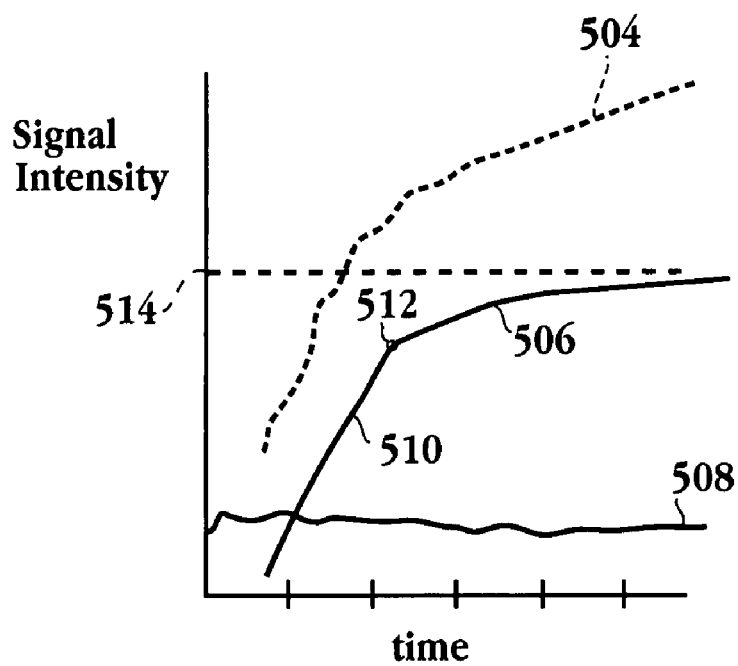
FIG. 11 is a perspective view illustrating a three-dimensional plot of complex impedance.

Referring now to FIG. 11, an embodiment for monitoring the ablative process the impedance signal intensity 510 for a sample volume of tissue bounded by two or sensing members or array can be monitored over time using a monitoring device, a power supply or other bioelectric signal monitoring means known in the art. An endpoint for ablation can be determined based on either a selectable threshold value 514 of signal 510 or an inflection point or change in slope 512 (e.g. a derivative) of curve 506 or a combination of both. In an embodiment signal 506 can comprise the subtraction of a baseline (or reference) impedance determination 508 of a nearby, but non-ablated tissue volume, from a real time measurement 504 of the target tissue volume during the time course of ablation. This compensates for any signal or tissue hysteresis over time. Threshhold values 514 and signals 510 can be input and stored in logic resource coupled to the impedance monitoring device or incorporated into an electronic algorithm controlling the delivery of energy which can be stored in a controller or processor coupled to the power supply.

Figure 12A:
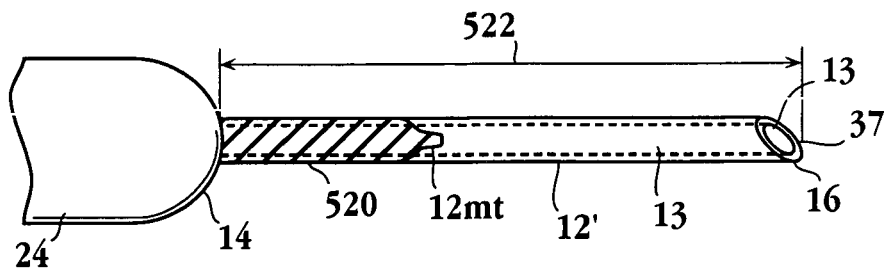
FIG. 12a is a lateral view illustrating an embodiment of the introducer.

Turning now to a further discussion of the introducer, in various embodiments, introducer can be a trocar, catheter, multi-lumen catheter, or a wire-reinforced or metal-braided polymer shaft, a port device, a subcutaneous port device, an elongated delivery device, or other medical introducing device known to those skilled in the art. In various embodiments, the introducer as well as resilient member can be configured to have varying mechanical properties along their respective lengths including, but not limited to variable stiffness, torquability, column strength, flexural modulus, pushability, trackability and other mechanical performance parameters known in the catheter arts. Referring to FIG. 12a, this can be achieved through the use of stiff shafts sections 520 disposed within portions of the introducer along its length 522. It can also be accomplished through the use of braids, varying/tapered diameters and different materials (e.g. stiffer materials joined to flexible materials) positioned over portions of introducer. Sections 520 made from different materials can be joined using introducer bonding methods known in the art such as hot melt junctions (with and without capture tubes/collates), adhesive joints, but joints and the like. The joining method can be controlled/selected so as to control the mechanical transition 12mt between two sections to a desired gradient (e.g. smooth vs. abrupt). In related embodiments, introducer 12 and/or member 18 can be configured to have stiffer proximal portions and more flexible distal portions so as to facilitate one or more of the following (i) introducer steerability and positioning of the introducer distal tip 16 at a selectable target tissue site, (ii) reduced risk of perforation, abrasion and other trauma during the positioning the introducer to the tissue site. In various embodiments, the transition from the stiffer to the more flexible portion can be configured to be either (i) gradual with a linear or curve-linear transition, (ii) a step or abrupt transition, and (iii) combinations thereof.

Figure 12B:
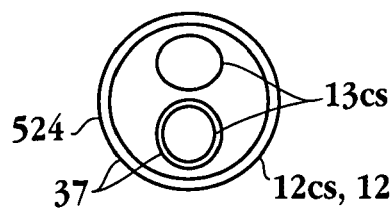
FIGS. 12b and 12c are cross sectional views illustrating cross-sectional profiles of the introducer.
Figure 12C:
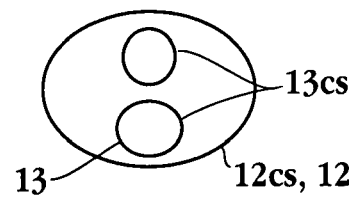

Referring to FIGS. 12b and 12c, introducer 12 can have a substantially circular, semicircular, oval or crescent shaped cross sectional profile 12cs, as well as combinations thereof along its length. Similarly, lumens 13 can have a circular, semicircular, oval or crescent shaped cross section for all or a portion of the length of introducer 12.

Suitable materials for introducer 12 and resilient member 18 include, but are not limited to, stainless steel, shape memory alloys such as nickel titanium alloys, polyesters, polyethylenes, polyurethanes, Pebax®, polyamides, nylons, copolymers thereof and other medical plastics known to those skilled in the art. All or portions of introducer 12 can be coated with a lubricious coating or film 524 which reduces the friction (and hence trauma) of introducer 12 with hepatic, pulmonary, bone and other tissue. Such coatings can include but are not limited to silicones, PTFE (including Teflon®) and other coatings known in the art. Also, all or portions of apparatus 10, including introducer 12 and members 18, can be constructed of materials known in the art that are optimized and/or compatible with radiation sterilizations (e.g. Gamma or E-beam). In related embodiments, all or portions of apparatus 10 can be configured (e.g. lumen diameter to length ratio, etc.) to be sterilized by plasma (e.g. $H_2O_2$) sterilization by systems.

Figure 13:
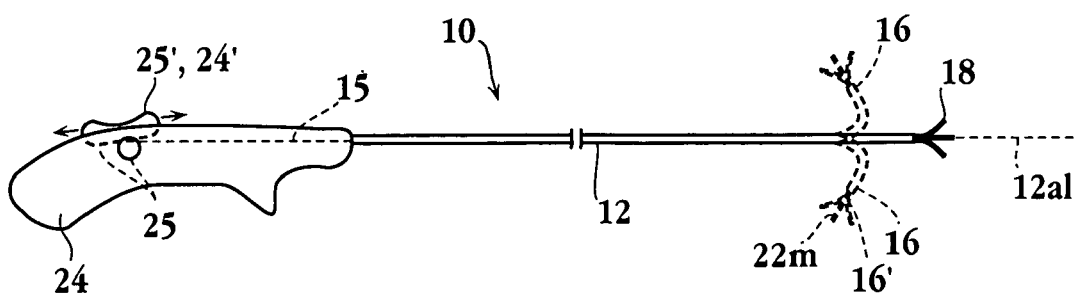
FIG. 13 is a lateral view illustrating an embodiment of a deflectable introducer along with the components of the introducer.

Referring now to FIG. 13, in other embodiments all or portions of introducer 12 or resilient members 18 can be configured to be deflectable and/or steerable using deflection mechanisms 25 which can include pull wires 15, ratchets, cams, latch and lock mechanisms, piezoelectric materials and other deflection means known in the art. The amount of deflection of introducer 12 is selectable and can be configured to allow the maneuvering of introducer 12 through oblique turns in tissue, organs, organ ducts and blood vessels. In specific embodiments, the distal portions of introducer 12 can be configured to deflect 0-180° or more in up to three axes to allow the tip of introducer 12 to have retrograde positioning capability. Deflection mechanism 25 can be coupled to, or integral with, a moveable or slidable actuator 24", 25' on handpiece 24. Mechanism 25 and coupled actuator 25' are configured to allow the physician to selectively control the amount of deflection 25 of distal tip 16 or other portion of introducer 12. Actuator 25' can be configured to both rotate and deflect distal tip 16 by a combination of rotation and longitudinal movement of the actuator.

Figure 14:
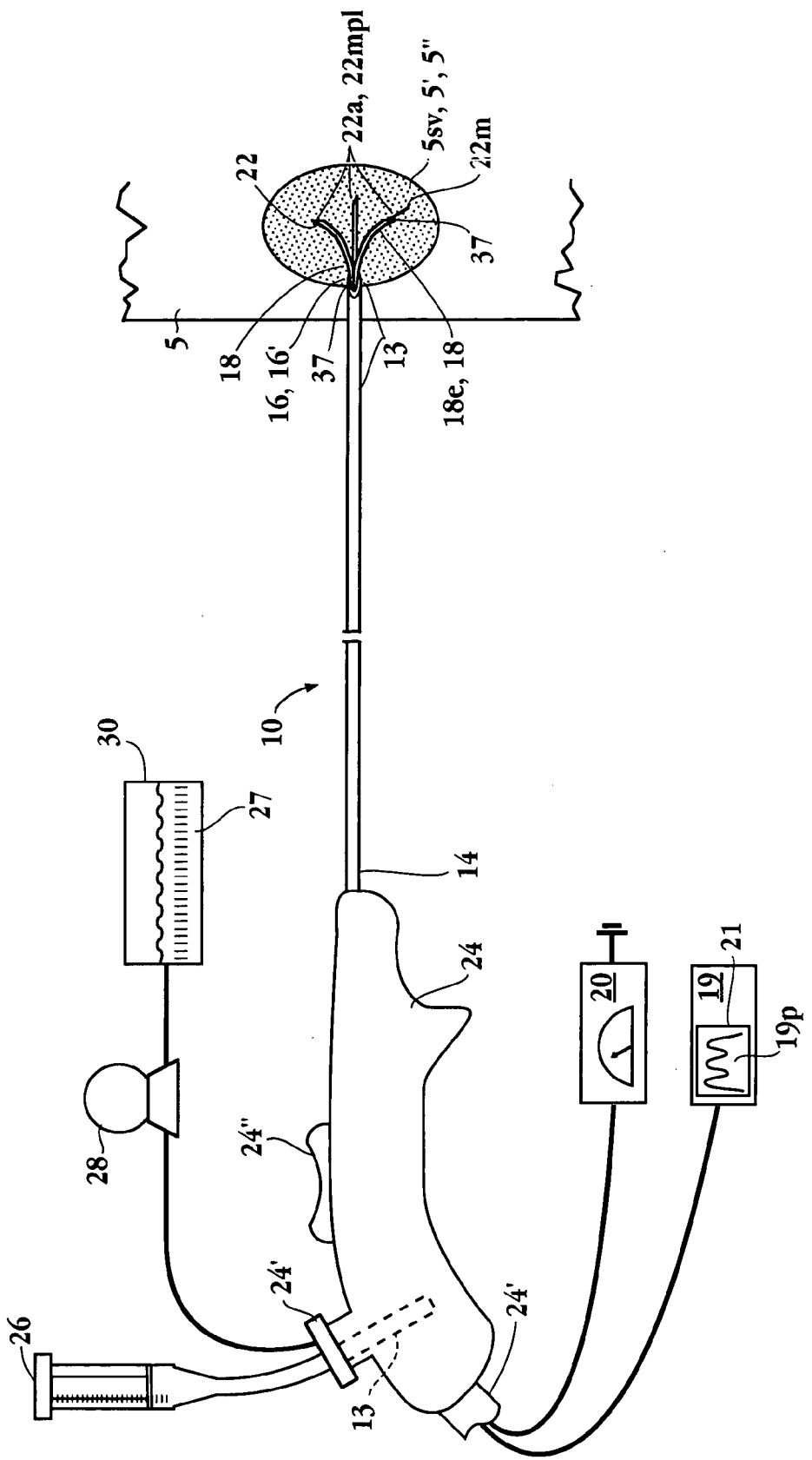
FIG. 14 is a lateral view illustrating an embodiment of a tissue biopsy and treatment apparatus with a hand piece and coupled aspiration device, fluid delivery device and fluid reservoir.

Referring now to FIG. 14, in various embodiments introducer 12 can be coupled at its proximal end 14 to a handle 24 or handpiece 24. Handpiece 24 can be detachable and can include ports 24' and actuators 24". Ports 24' can be coupled to one or more introducer lumens 13 (and in turn electrode lumens 72) and can include fluid and gas ports/connectors and electrical, or optical connectors. In various embodiments, ports can be configured for aspiration (including the aspiration of tissue), and the delivery of cooling, electrolytic, irrigation, polymer and other fluids (both liquid and gas) described herein. Ports can include but are not limited to luer fittings, valves (one-way, two-way), toughy-bourst connectors, swage fittings and other adaptors and medical fittings known in the art. Ports can also include lemoconnectors, computer connectors (serial, parallel, DIN, etc) micro connectors and other electrical varieties well known to those skilled in the art. Further, ports can include optoelectronic connections which allow optical and electronic coupling of optical fibers and/or viewing scopes to illuminating sources, eye pieces, video monitors and the like. Actuators 24" can include rocker switches, pivot bars, buttons, knobs, ratchets, levers, slides and other mechanical actuators known in the art, all or portion of which can be indexed. These actuators can be configured to be mechanically, electro-mechanically, or optically coupled to pull wires, deflection mechanisms and the like allowing selective control and steering of introducer 12. Handpiece 24 can be coupled to tissue aspiration/collection devices 26, fluid delivery devices 28 (e.g. infusion pumps) fluid reservoirs (cooling, electrolytic, irrigation etc) 30 or power source 20 through the use of ports 24'. Tissue aspiration/collection devices 26 can include syringes, vacuum sources coupled to a filter or collection chamber/bag. Fluid delivery device 28 can include medical infusion pumps, Harvard pumps, syringes and the like. In specific embodiments, aspiration device 26 can be configured for performing thoracentesis.

Turning now to a discussion of electrodes or resilient members 18 and sensing members 22*m*, these members can be of different sizes, shapes and configurations with various mechanical properties selected for the particular tissue site. In one embodiment, members 18 can be needles, with sizes in the range of 28 to 12 gauge with specific embodiments of 14, 16 and 18 gauges. Resilient members 18 are configured to be in non-deployed positions while retained in introducer 12. In the non-deployed positions, resilient members 18 may be in a compacted state, spring loaded and generally confined within introducer 12 or substantially straight if made of a suitable memory metal such as nitinol. As resilient members 18 are advanced out of introducer 12 they become distended to a deployed state as a result of their spring or shape memory that collectively defines an ablative volume 5*av*, from which tissue is ablated as illustrated more fully in FIGS. 1 and 2. The selectable deployment of resilient members 18 can be achieved through one or more of the following approaches (i) the amount of advancement of resilient members 18 from introducer 12;

(ii) independent advancement of resilient members 18 from introducer 12;

(iii) the lengths and/or sizes of energy delivery surfaces of electrodes 18 and 18';

(iv) variation in materials used for electrode 18;

(v) selection of the amount of spring loading or shape memory of electrode 18;

(vi) variation of the geometric configuration of electrode 18 in their deployed states; and (vii) preformed to assume curvature when the resilient members 18 are advanced from the introducer 12.

As described herein, in various embodiments all or a portion of resilient member 18 can be an energy delivery device or member 18*e*. Turning to a discussion of energy delivery device and power sources, the specific energy delivery devices 18*e* and power sources 20 that can be employed in one or more embodiments of the invention include but are not limited to, the following:

(i) a microwave power source coupled to a microwave antenna providing microwave energy in the frequency range from about 915 MHz to about 2.45 GHz;

(ii) a radio-frequency (RF) power source coupled to an RF electrode;

(iii) a coherent light source coupled to an optical fiber or light pipe;

(iv) an incoherent light source coupled to an optical fiber;

(v) a heated fluid coupled to a catheter with a closed or at least partially open lumen configured to receive the heated fluid;

(vi) a cooled fluid coupled to a catheter with a closed or at least partially open lumen configured to receive the cooled fluid;

(vii) a cryogenic fluid;

(viii) a resistive heating source coupled to a conductive wire;

(ix) an ultrasound power source coupled to an ultrasound emitter, wherein the ultrasound power source produces ultrasound energy in the range of about 300 KHZ to about 3 GHz, (xi) and combinations thereof. For ease of discussion for the remainder of this application, the energy delivery device 18*e* is one or more RF electrodes 18 and the power source utilized is an RF power supply. For these and related embodiments, RF power supply 20 can be configured to deliver 5 to 200 watts, preferably 5 to 100 watts, and still more preferably 5 to 50 watts of electromagnetic energy is to the electrodes of energy delivery device 18*e* without impeding out. The electrodes 18 are electro magnetically coupled to energy source 20. The coupling can be direct from energy source 20 to each electrode 18 respectively, or indirect by using a collet, sleeve and the like which couples one or more electrodes to energy source 20.

Figure 16:
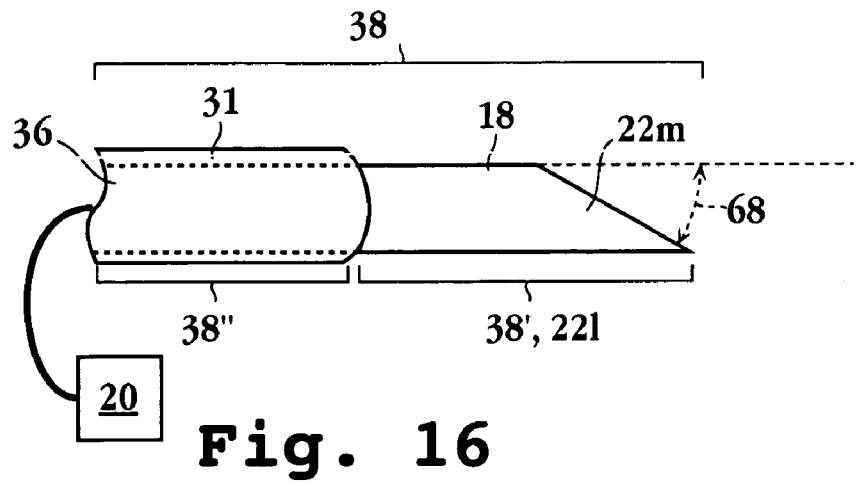
FIG. 16 is lateral view illustrating an embodiment of a needle electrode configured to penetrate tissue.

In various embodiments, electrodes 18 include at least one sensor 22 and sensing members 22*m* can have a variety of shapes and geometries. Referring now to FIGS. 15*a*-15*f*, example shapes and geometries can include, but are not limited to, ring-like, ball, hemispherical, cylindrical, conical, needle-like and combinations thereof. Referring to FIG. 16, in an embodiment electrode 18 can be a needle with sufficient sharpness to penetrate tissue including fibrous tissue including, encapsulated tumors cartilage and bone. The distal end of electrode 18 can have a cut angle that ranges from 1 to 60°, with preferred ranges of at least 25° or, at least 30° and specific embodiment of 25° and 30°. The surface of electrode 18 can be smooth or textured and concave or convex. Electrode 18 can have different lengths 38 that are advanced from distal end 16' of introducer 12. The lengths can be determined by the actual physical length of electrode(s) 18*e*, the length 38' of an energy delivery surface 18*eds* of electrode 18 and the length, 38" of electrode 18 that is covered by an insulator 36. Suitable lengths 38 include but are not limited to a range from 1-30 cms with specific embodiments of 0.5, 1, 3, 5, 10, 15 and 25.0 cm. The conductive surface area of the electrode 18 can range from 0.05 mm$^2$ to 100 cm$^2$. The actual length of the electrode 18 depends on the location of tissue site to be ablated, its distance from the site, its accessibility as well as whether or not the physician performs an endoscopic or surgical procedure. Meanwhile, the conductive surface area 18*eds* depends on the desired ablation volume to be created.

Figure 17:
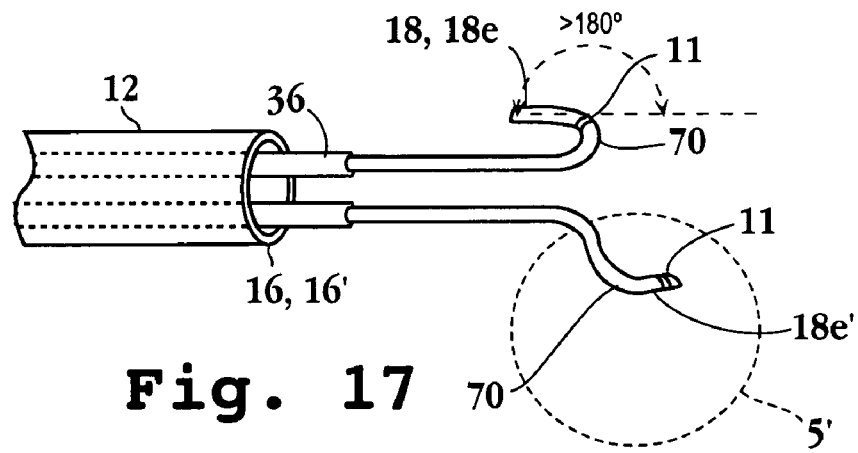
FIG. 17 is lateral view illustrating an embodiment of an electrode having at least one radius of curvature.
Figure 18:
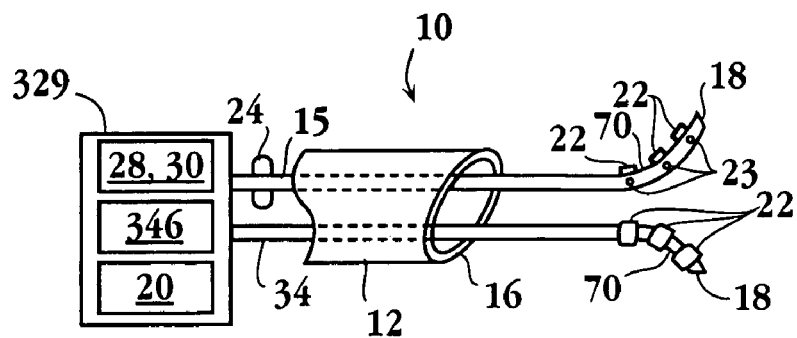
FIG. 18 is lateral view illustrating an embodiment of the electrode having at least one radius of curvature, sensors and a coupled advancement device.
Figure 19:
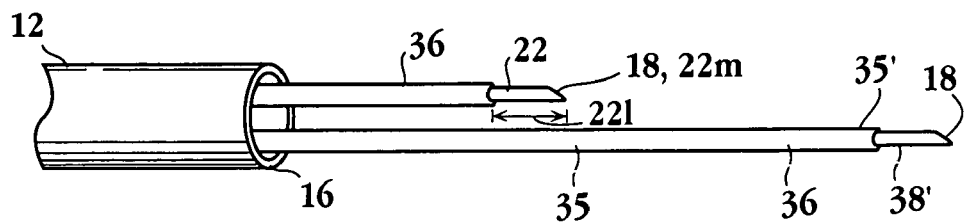
FIG. 19 is a perspective view illustrating an embodiment of the electrode that includes insulation sleeves positioned at exterior surfaces of the resilient members or electrodes so as to define an impedance sensor length or an energy delivery surface.

Referring now to FIGS. 17 and 18, electrode 18 can also be configured to be flexible and or deflectable having one or more radii of curvature 70 which can exceed 180° of curvature. In use, electrode 18 can be positioned to heat, necrose or ablate any selected target tissue volume. A radiopaque marker 11 can be coated on the electrodes 18e for visualization purposes. Electrode 18 can be coupled to introducer 12 and or an advancement member or device 15 or an advancement-retraction member using soldering, brazing, welding, crimping, adhesive bonding and other joining methods known in the medical device arts. Also, the electrode 18 can include one or more coupled sensors 22 to measure temperature and impedance (both of the electrode and surrounding tissue), voltage and current other physical properties of the electrode and adjacent tissue. Sensors 22 can be at exterior surfaces of electrodes 18 at their distal ends or intermediate sections.

Electrode 18 can be made of a variety of conductive materials, both metallic and non-metallic. Suitable materials for electrode 18 include, steel such as 304 stainless steel of hypodermic quality, platinum, gold, silver and alloys and combinations thereof. Also, electrode 18 can be made of conductive solid or hollow straight wires of various shapes such as round, flat, triangular, rectangular, hexagonal, elliptical and the like. In a specific embodiment all or portions of electrodes 18 or a second electrode can be made of a shaped memory metal, such as NiTi, commercially available from Raychem Corporation, Menlo Park, Calif.

Referring now to FIGS. 19 through 22 in various embodiments one or more resilient members or electrodes 18 can be covered by an insulative layer 36 so as to have an exterior surface that is wholly or partially insulated and provide a non-insulated area which is an energy delivery surface. In an embodiment shown in FIG. 19, insulative layer 36 can comprise a sleeve that can be fixed or slidably positioned along the length of electrode 18 to vary and control the length of the energy delivery surface. Suitable material for insulative layer 36 includes polyamide and fluorocarbon polymers such as TEFLON.

Figure 20:
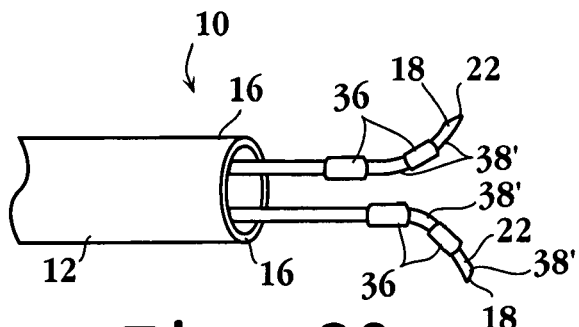
FIG. 20 is a perspective view illustrating an embodiment of the electrode that includes multiple insulation sleeves that circumferentially insulate selected sections of the electrode(s).
Figure 21:
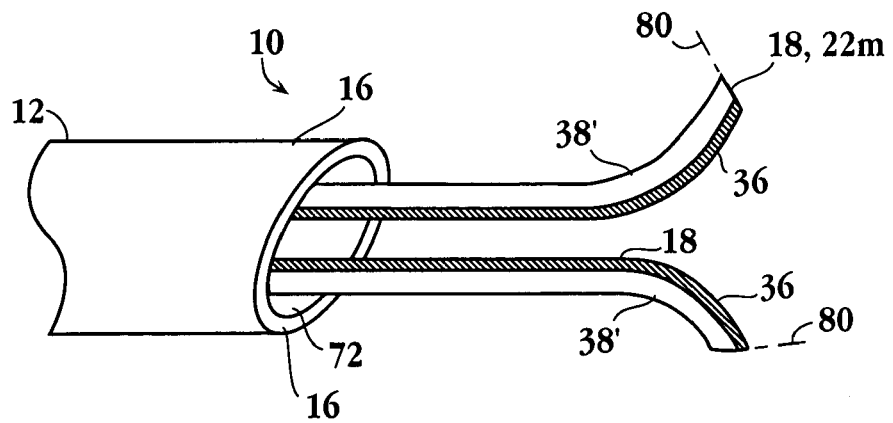
FIG. 21 is a perspective view illustrating an embodiment of the electrode with insulation that extends along longitudinal sections of the electrodes to define adjacent longitudinal energy delivery surfaces.
Figure 22:
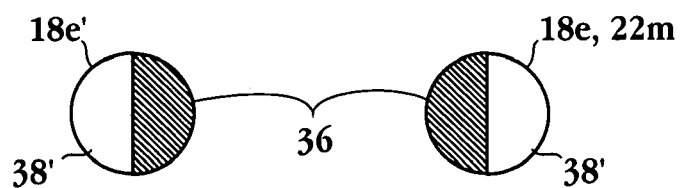
FIG. 22 is a cross-sectional view of the embodiment of FIG. 21.

In the embodiment shown in FIG. 20, insulation 36 is formed at the exterior of the electrodes 18 in circumferential patterns, leaving a plurality of energy delivery surfaces. In an embodiment shown in FIGS. 21 and 22, insulation 36 extends along a longitudinal exterior surface of the electrodes 18. Insulation 36 can extend along a selected distance along a longitudinal length of the electrodes and around a selectable portion of a circumference of the electrodes. In various embodiments, sections of the electrodes can have insulation 36 along selected longitudinal lengths of electrodes as well as completely surround one or more circumferential sections of electrodes. Insulation 36 positioned at the exterior of electrodes 18 can be varied to define any desired shape, size and geometry of energy delivery surface.

Figure 23A:
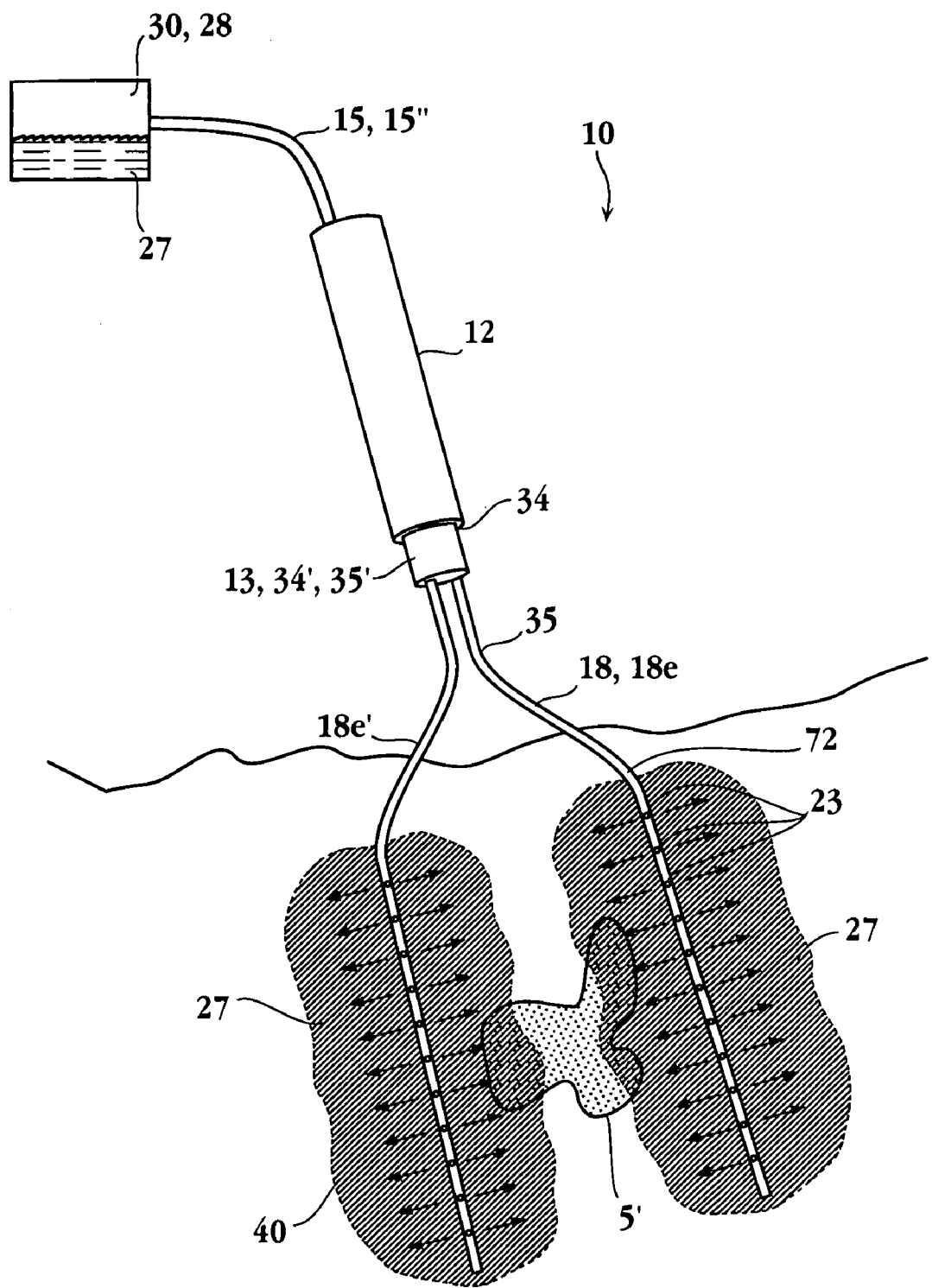
FIG. 23a is a lateral view illustrating an embodiment of the apparatus with an electrode having a lumen and apertures configured for the delivery of fluid and the use of infused fluid to create an enhanced electrode.

Referring now to FIGS. 23a and 23b, in various embodiments electrode 18 can include one or more lumens 72 (which can be contiguous with or the same as lumen 13) coupled to a plurality of fluid distribution ports 23 (which can be apertures) from which a variety of fluids 27 can be introduced, including conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media and combinations thereof. This is accomplished by having ports or apertures 23 that are fluidically coupled to one or more lumens 72 coupled to lumens 13 in turn coupled to fluid reservoir 30 and/or fluid delivery device 28.

In an embodiment shown in FIG. 23a, a conductivity enhancing solution 27 can be infused into a target tissue site 5' including a tissue mass. The conductivity enhancing solution can be infused before during or after the delivery of energy to the tissue site by the energy delivery device. The infusion of a conductivity enhancing solution 27 into the target tissue 5' creates an infused tissue area that has an area of increased or otherwise controlled electrical conductivity (verses non-infused tissue) so as to act as an enhanced electrode 40 or an area of controlled tissue impedance 40. During RF energy delivery, tissue impedance and the current densities in enhanced electrode 40 are controlled to an optimum level allowing the delivery of greater amounts of RF power into electrode 40 and target tissue 5' without shut downs of the RF power supply due to excessive localized impedance. In use, the infusion of the target tissue site with conductivity enhancing solution provides two important benefits: (i) faster ablation times; (ii) the creation of larger lesions; and (iii) reduced incidence of impedance-related shut downs of the RF power supply. This is due to the fact that the conductivity enhancing solution reduces current densities and prevents desiccation of tissue adjacent the electrode that would otherwise result in increases in tissue impedance. Also, these and related embodiments provide the benefit of a significantly reduced risk of pad burns to the patient due to the use of lower power levels which lowers the current density at the interface between the patients skin and a ground pad electrode.

A preferred example of a conductivity enhancing solution is a hypertonic saline solution. Other examples include halide salt solutions, colloidal-ferro solutions and colloidal-silver solutions. The conductivity of enhanced electrode 40 can be increased by control of the rate and amount of infusion and the use of solutions with greater concentrations of electrolytes (e.g. saline) and hence greater conductivity. In various embodiments, the use of conductivity enhancing solution 27 allows the delivery of up to 2000 watts of power into the tissue site impedance shut down, with specific embodiments of 50, 100, 150, 250, 500, 1000 and 1500 watts achieved by varying the flow, amount and concentration of infusion solution 27. The infusion of solution 27 can be continuous, pulsed or combinations thereof and can be controlled by a feedback control system 329 described herein. In a specific embodiment, a bolus of infusion solution 27 is delivered prior to energy delivery followed by a continuous delivery initiated before or during energy delivery with energy delivery device 18e or other means.

In various embodiments, the apparatus can include impedance determination, tissue ablation capabilities and can be configured to not only infuse fluid but also to do so as to control tissue impedance at the target tissue site. An embodiment of an ablation apparatus configured for tissue infusion tissue for impedance control is shown in FIG. 23b. In this and related embodiments, fluid delivery device 28 can be a syringe pump configured with multiple syringes 28s, multiple-bore syringes 28b with each syringe coupled to a separate fluid lumen or channel 72 directly or via a valve such as an indexing valve. Related embodiments of infusion device 28 can include an indexing valve as well as multi-lumen tubing or multi-channel tubing connected to one or more electrode lumens 72 via introducer lumen 13 or other channel within external to introducer 12. Multi-channel tubing can be fabricated from PEBAX, silicone, polyurethane or other resilient polymer using extrusion technology known in the art. Use of an indexing valve allows independent control of flow rates through individual lumens 72 in turning allowing for independent control of infusion through electrodes 18. This in turn, allows for greater control of the infusion process including the creation of smaller or larger zones of infusion around individual electrodes 18. Such control is particularly beneficial for bipolar embodiments where, in order to prevent shorting, it is desirable not to have a continuous infusion zone between one or more bipolar electrodes 18 and a return electrode.

As described herein the tissue ablation apparatus can be configured to infuse a fluid 27 to control or maintain tissue impedance at the target tissue site. In various embodiments this can be accomplished using feedback control devices, systems, a control for the fluid delivery device, and algorithms described herein and known in the art such as proportional, proportional-integral control or proportional-integral-derivative methods. Further as shown in FIG. 23c, feedback control system can be coupled to fluid delivery device (or the fluid delivery control, not shown) and the impedance monitoring device in order to receive an input or monitoring signal from the monitoring device and output a control signal to device. The delivery of fluid to tissue site can be flow or pressure controlled. Accordingly, in various embodiments the control system regulates impedance by regulating the infusion flow rate through one or more channels, the infusion fluid pressure within channels or a combination of both. Flow rates can be controlled to a range of about 0.01 to about 2.5 ml/per channels with specific embodiments of 0.1, 0.25, 0.5, 0.75, 1.0, 1.5 and 2.0 ml/min. Pressure can be control to a range of 0.01 to 5 atms with specific embodiments of 0.1, 0.25, 0.5, 0.75, 1.0, 1.5 and 2.5 atms.

Other embodiments of fluid delivery methods and ablation apparatus with associated features can be employed such as those described in U.S. patent application Ser. No. 60/290,060 filed May 10, 2001 which is fully incorporated by reference herein.

A discussion will now be presented of types of impedance that can be measured and controlled in various embodiments of the invention, these include system impedance and local impedance. The local impedance is the impedance along a conductive pathway 22 within target tissue site which in bipolar embodiments can be measured between one or more electrodes. The system impedance is the cumulative impedance of the local impedance along conductive pathway, the impedance on the conductive pathway between the rest of the body (the abdomen, legs, skin etc) and a ground pad electrode, the impedance of the groundpad electrode, the impedance of the RF generator, the impedance of the trocar or delivery device, the impedance of electrodes and the impedance of all the associated cabling coupling one or more components of the apparatus to devices and component described herein (e.g. the RF generator, etc.). Local impedance can be measured directly by measuring the impedance along conductive pathways between one or more electrodes in bipolar embodiments. Alternatively, local impedance can be measured indirectly by taking baseline impedance determinations of system impedance prior to ablative therapy and then subtracting this value from impedance determinations during ablative therapy. In related embodiments the impedance of the apparatus and RF generator can be predetermined using a calibration device or a pre-calibrated tissue/body impedance simulator. Again these values can be stored and subtracted from real time system impedance determinations to yield local impedance.

Local impedance can determined between one or more electrodes or can be determined between the interior and exterior of a hollow electrode by coating an exterior portion of electrode with an insulative coating such that current flows between non-insulated exterior portions of the electrode and the interior portions. Alternatively all or portions of electrode can comprise a coaxial cable with an interior electrode and an exterior electrode.

A discussion will now be presented of the impedance determinations and calculations used by various embodiments of the invention. In an embodiment the impedance measured by impedance determination device or power generator is system impedance. System impedance includes the local impedance (LI) from the target tissue site and from the rest of the body (BI) as well as the groundpad and the generator and cables. Typically the impedance from the rest of the body (BI) is fixed while the local impedance (LI) is variable. This allows for an indirect determination of local tissue impedance by taking a baseline impedance determination (either before or at the onset of RF power delivery) and then subtracting out the baseline determination. Determination of local tissue impedance and system impedance allows for the determination of a parameter known as impedance efficiency (IE). This value is the ratio of local tissue impedance over the system impedance (LI/SI). The IE value allows for the determination of another parameter known as power dissipation efficiency (PDE). This value is the ratio of the amount of the RF power actually dissipated at the target tissue site (due to ohmic heating) to the total power delivered from the RF generator for a given power setting. PDE can be theoretically determined by multiplying the RF power setting by the IE. Maximizing PDE maximizes the amount of power dissipated at the lesion and hence lesion heating and thermally induced necrosis. Generally, higher PEDs allow for faster, larger and more optimal ablations while minimizing the risk of pad burns by reducing the amount of power required to produce an ablation volume and hence the resulting current density at the interface between the patients skin and a ground pad or return electrode coupled the RF generators.

PDE can be optimized/maximized by a variety of means including control systems and methods described herein. Accordingly, various embodiments of the invention can be configured to optimize PDE by control of one or more of the following parameters including, but not limited to, target tissue site impedance including target tissue impedance gradients as function of distance from the electrode, electrode impedance, electrode surface impedance, system impedance and target tissue current density including current density gradients as a function of distance from the electrode. One or more of these parameters can be set point controlled using control systems and methods described herein. In an embodiment shown in FIG. 23d, PDE is maximized by controlling system impedance and/or local impedance to an optimal value 526 or range. Prior RF ablative approaches sought to maximize the delivery of power to the tissue site by minimizing system impedance. Embodiments of the present invention utilize a contrary and novel approach by controlling impedance (either local or system) above a minimum value or to an optimum value in order to maximize PED. This optimal value is above a minimum value because when local impedance is too low, there is a reduced power dissipation at the target tissue site in relation to the rest of body, (e.g. the legs, torso and interface between the ground-pad and skin). This approach employed by various embodiments of the invention represents a radical departure from previous RF ablative methodologies which were based on the belief that the lower the tissue impedance the better. Embodiments of the present invention are configured to achieve increased power delivery to the tissue site by actually increasing local impedance to higher levels so as to obtain an increased IE value.

Figure 23D:
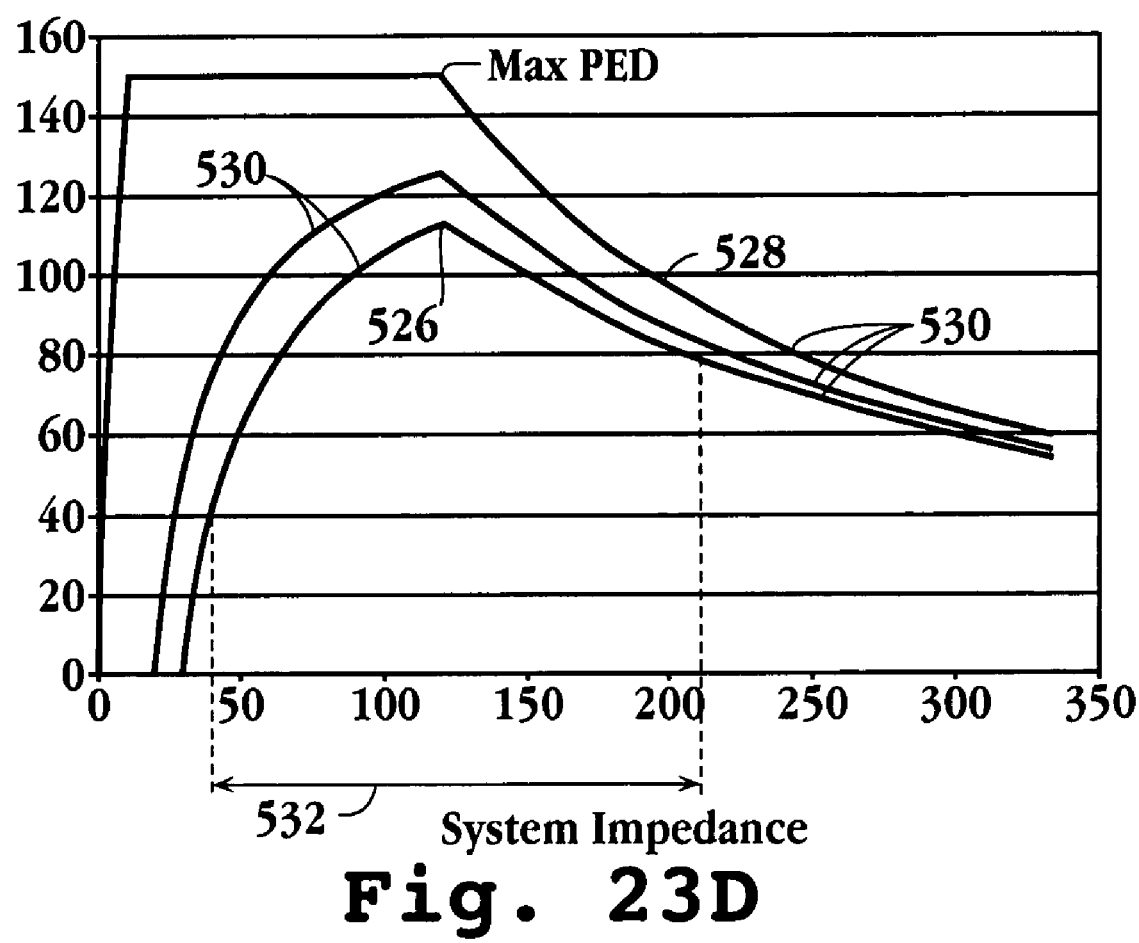
FIG. 23d are plots of dissipated power verses impedance illustrate a novel approach of maximizing ablative power delivery at a target tissue site at a non-minimal impedance.

As shown in FIG. 23d, tissue impedances below the optimal impedance 526 result in sharp drop off (e.g. a second order, curvlinear or logarithmic decrease) of the delivered power 528 on the curve 530, while values above the optimal impedance results in a more gradual linear or asymptotic decrease. Using this and related curves, delivered power to the target tissue site can be controlled by controlling local impedance via the infusion rate of a conductive solution or other means described herein. Accordingly, in various embodiments local impedance can be controlled to be not only set at the optimal impedance value, or optimal impedance range 532, but can also be maintained at values above or below the optimal impedance over the time course of the ablative therapy. In use, this allows the medical practitioner to more precisely titrate the delivery of ablative energy to the size, shape and consistency of a specific tumor volume, as well as account for local anatomy such as nearby or internal blood vessels. Further, these and related embodiments allow the medical practitioner to rapidly increase or decrease delivered power over the time course of the ablation without having to change the power setting on the RF generator. Various embodiments of the invention can include preprogrammed flow rate profiles or programs (stored in memory resources described herein) so as to produce a time variable local impedance profile over the time course of the ablation. For example, the flow rate could be programmed to operate to right of the linear portion of the curve 530 so as to gradually increase delivered power, then shift to impedance value at optimal impedance and then shift the impedance to the left of optimal impedance to rapidly decrease delivered power near the end of the ablation. This embodiment provides the benefit of minimizing damage to surrounding healthy tissue near the end of ablation. Alternatively, a reverse profile could be employed. Related embodiments could include infusion/impedance profiles that have multiple intervals shifting to the left and the right of the optimal impedance. The apparatus could also be configured to allow the practitioner to manually control the flow rate/impedance profile to meet the requirements of individual tumor volumes. A database of infusion/impedance profiles could be stored in a memory resources or a database.

As described herein, in various embodiments optimal impedance can be controlled and maintained by the infusion of a conductive solution to the target tissue site to control local impedance. This can be accomplished by inputting measurements from sensors and/or electrodes to a control system electronically coupled to an infusion device described herein. In various embodiments control system can be a closed loop system employing Proportional, PI, PID methods as well as fuzzy logic algorithms known in the art. A control system can be configured to control both the flow rate as well as the conductivity of the infused solution by controlling the electrolyte concentration/salinity of the infused solution. Referring back to FIG. 23*a*, the latter can be accomplished by coupling a source of dilute solution to the reservoir via a control valve or by configuring the reservoir to have two or more chambers containing concentrated and dilute electrolytic solutions. In either embodiment, control valve can be utilized to mix the two solutions in a proportion to achieve the desired electrolyte concentration using conductivity/pH sensors known in the art to monitor the output electrolyte concentration.

In related embodiments, two or more process parameters can be controlled to maintain local or system impedance at an optimal impedance value. In an embodiment, RF generator power and the infusion rate can be controlled in concert to control local or system impedance. In situations where impedance is too low, RF power can be increased and infusion rate decreased. This serves to dry out the target tissue site by vaporizing or otherwise driving out fluid from the target tissue site and/or allowing the fluid to dissipate from the tissue site. Alternatively, the fluid delivery device can be coupled to a vacuum source or otherwise be configured to apply negative pressure to suction off fluid from the target tissue into the lumen(s) of the electrode or lumen(s) of the introducer. When impedance is too high infusion rates can be increased in combination with a decrease in RF power levels.

In various embodiments, the optimal impedance or impedance range can be maintained in the range of 5 to 200 ohms with a preferred range of 30 to 150 ohms and specific embodiments of 10, 15, 20, 30, 40, 50, 75, 80, 90, 100, 110 and 120 ohms. The value of the optimal impedance can be determined using a calibration software program and/or a calibration test fixture (not shown) which can be configured to simulate local tissue and/or body impedance using biomedical instrument calibration methods known in the art. In use, the doctor would connect an ablation apparatus or catheter to a RF generator in order to determine a unique value of the optimal impedance for given catheter generator combination. Alternatively, each catheter can be factory calibrated using biomedical instrument calibration methods known in the art. The value could be stored in a microprocessor or ROM chip known in the art that is integral or coupled to the apparatus and configured to electrically signal the measurement device and/or the generator. Also the control system, measurement device, or the generator can be configured to allow the medical practitioner to manually enter a value for the optimal impedance.

Figure 23E:
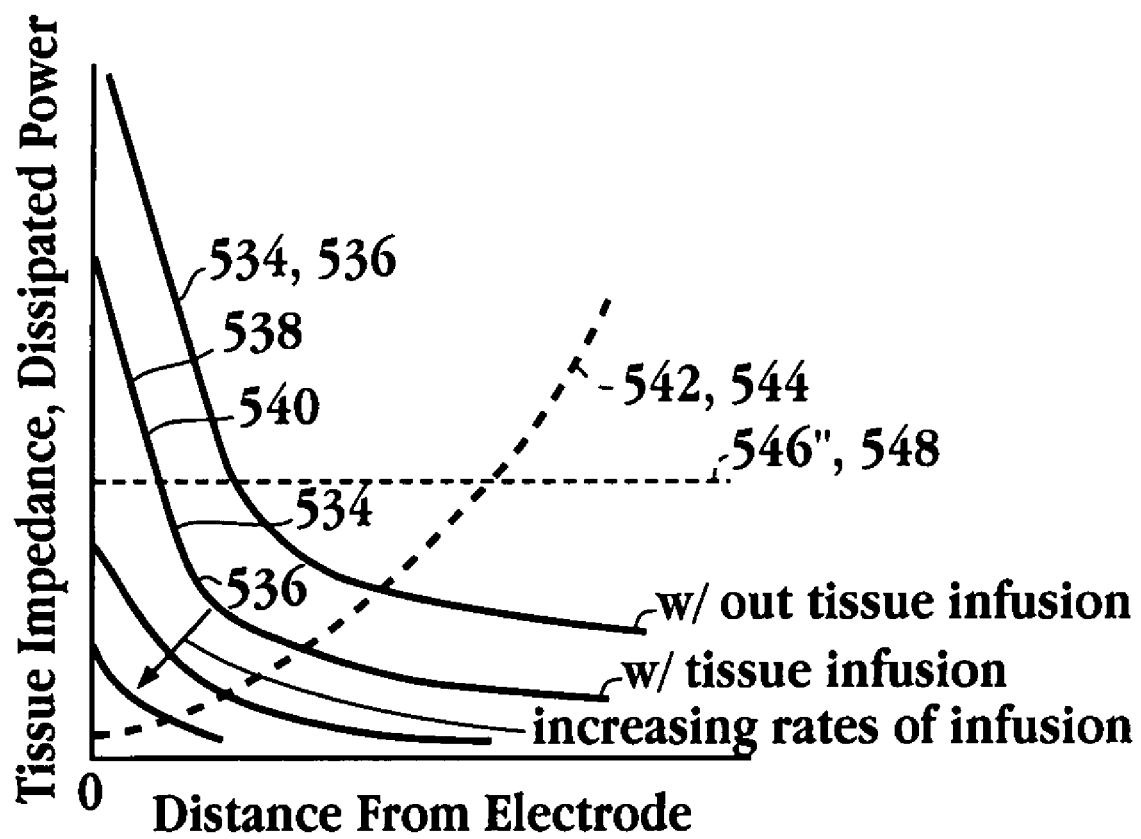
FIG. 23e is a plot of tissue resistance versus distance from embodiments of the electrode which illustrate the use of infusion to reduce tissue charring adjacent the electrode.

In embodiment shown in FIG. 23*e*, the infusion of solution can be controlled to control the positional impedance profile or gradient 534 (that varies as a function of the distance from the electrode) and hence a power dissipation gradient 536. An optimal impedance gradient 538 can be selected to in turn produce an optimal power dissipation gradient 540 to optimize the delivery of power in the target tissue site. In an embodiment, the infusion flow rate can be controlled to maintain the impedance gradient substantially constant (ins shape and position) over the time course of the ablation. Alternatively, flow rates can be increased or decreased as needed by control system 329 to shift the impedance gradient over the time course of ablative RF power delivery to optimize ablation volume and minimize ablation times. Decreasing infusion rates (and/or decreasing electrolytic concentration) shifts the impedance gradient to the right to allow more power to be delivered to target tissue to produce larger ablation volumes in short periods of time. Increase infusing rates allows the impedance gradient to be shifted to the left to minimize tissue desiccation and charring and prevent or reduce impedance induced shut downs of the generator (so called impeding out). In an alternative embodiment, the infusion of fluid can be configured to produce a constant impedance profile 546, 548 or a increasing gradient 542, 544. The use of an optimal impedance gradient provides the benefit of a more precise or fine tuned control of the ablation process by accounting for impedance differences within the target tissue site particularly those adjacent the electrode. In various embodiments, the impedance gradient 534 can be configured to be linear, logarithmic, second order, third order or other polynomial function. Flow rate programs or subroutines that can be used to produce such gradients can be stored in memory resources and/or logic resources.

Figure 24:
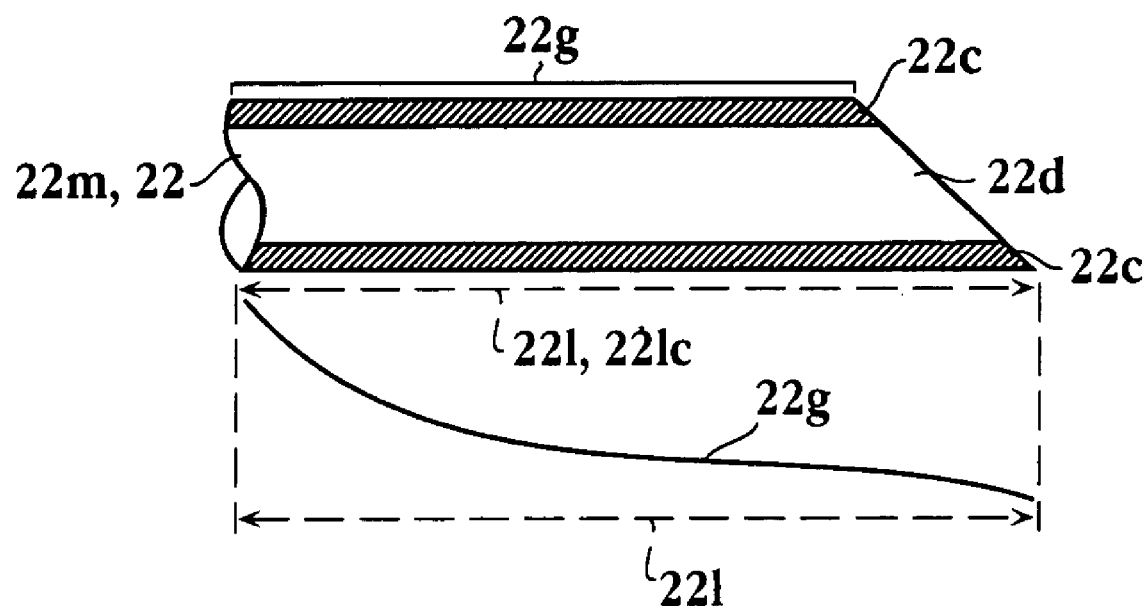
FIG. 24 is a perspective view illustrating an embodiment of an impedance-sensing member that includes a conductive coating that can be configured to produce an impedance gradient within the sensing member.

Turning now to a discussion of sensors, in various embodiments, sensors can include all or a portion of the resilient members. Referring back to FIG. 19, when resilient member 18 is made of a conductive material the length of the sensor 221 can be defined by the placement of a slidable or fixed insulative layer 36. Also in various embodiments, sensors 22 can fabricated from a variety of conductive materials and metals known in the art including stainless steel, copper, silver, gold, platinum and alloys and combinations thereof. Referring now to FIG. 24, similarly all or portions of sensors 22 or sensing members 22m can comprise a conductive metal layer or conductive polymer coating 22c that is coated or deposited (onto a selected portion of resilient member 18 using methods known in the art such as sputtering, vacuum deposition, dip coating, photolithography and the like. In a related embodiment, sensing members 22m and/or sensor 22 can be configured to have a resistance gradient 22g along all or portions of their lengths 22l. The resistance gradient can be increasing or decreasing in a linear, second order, third order, exponential or other fashion. In a specific embodiment, the resistance gradient is configured to compensate for resistance losses (i.e. of voltage) and/or hysteresis occurring along the length of sensor 22, as well as changes in the overall resistance of sensor 22 due changes in the temperature and/or conducting/sensing length 22lc (and area) of sensor 22 as might occur due to advancement or retraction of slidable insulation layer, or fowling of the sensor with, desiccated, burnt tissue or otherwise adherent tissue. In this, and related embodiments, the gradient can be so configured to produce the least resistance (e.g. maximum conductance) at the distal tip 22d of the sensor 22 and increasingly moving in a proximal direction along. The gradient can be produced via the use of coating 22c either by varying the thickness or composition of the coating, or a combination of both along the length 22l of the sensor using methods known in the art. Further, by compensating for such resistance changes or losses along the length or area of the sensor, these and related embodiments also improve the detection of real and imaginary components of complex impedance. In other related embodiments, the resistance gradient can be in a radial direction or a combination of radial and linear directions with respect to the sensor length 22l.

In other embodiments the sensors can comprise a number of biomedical sensors known in the art including but not limited to thermal sensors, acoustical sensors, optical sensors, voltage sensors, current sensors, pH sensors, gas sensors, flow sensors positional sensors and pressure/force sensors. Thermal sensors can include thermistors, thermocouples, resistive wires, optical sensors and the like. Acoustical sensors can include ultrasound sensors including piezoelectric sensors which can be configured in an array. Pressure and force sensors can include strain gauge sensors including silicon-based strain gauges.

In an embodiment, the sensor can be selected to measure temperature along with impedance to compensate for any temperature related bias or hysteresis in the impedance determination. Accordingly, in an embodiment a feedback signal from a temperature sensor or temperature calculation device can be inputted to an impedance calculation device described herein to compensate for such variation. Temperature monitoring can also be used for real time monitoring of energy delivery. If at any time date from the sensors determines that a desired cell necrosis temperature is exceeded, then an appropriate signal is sent to the controller which then regulates the amount of electromagnetic energy delivered to the electrodes.

Figure 25A:
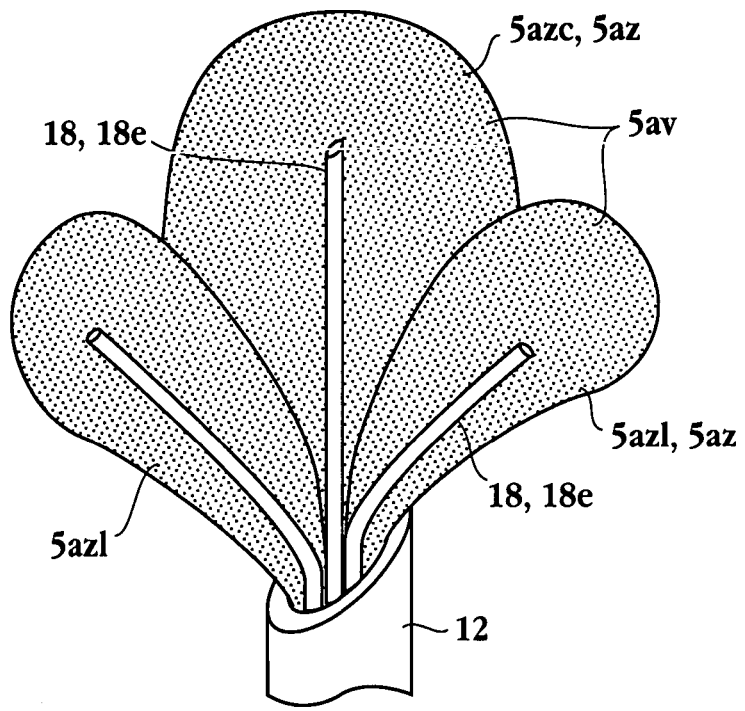
FIGS. 25a-25c are perspective views of an embodiment of an energy delivering ablation apparatus using frequency controlled positionable ablation fields.
Figure 25B:
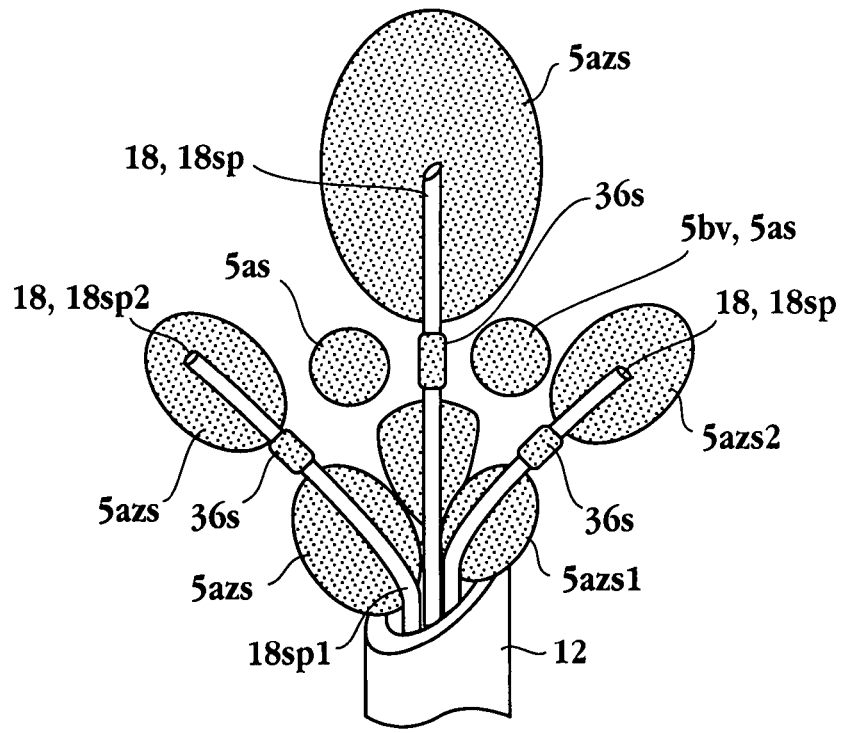
Figure 25C:
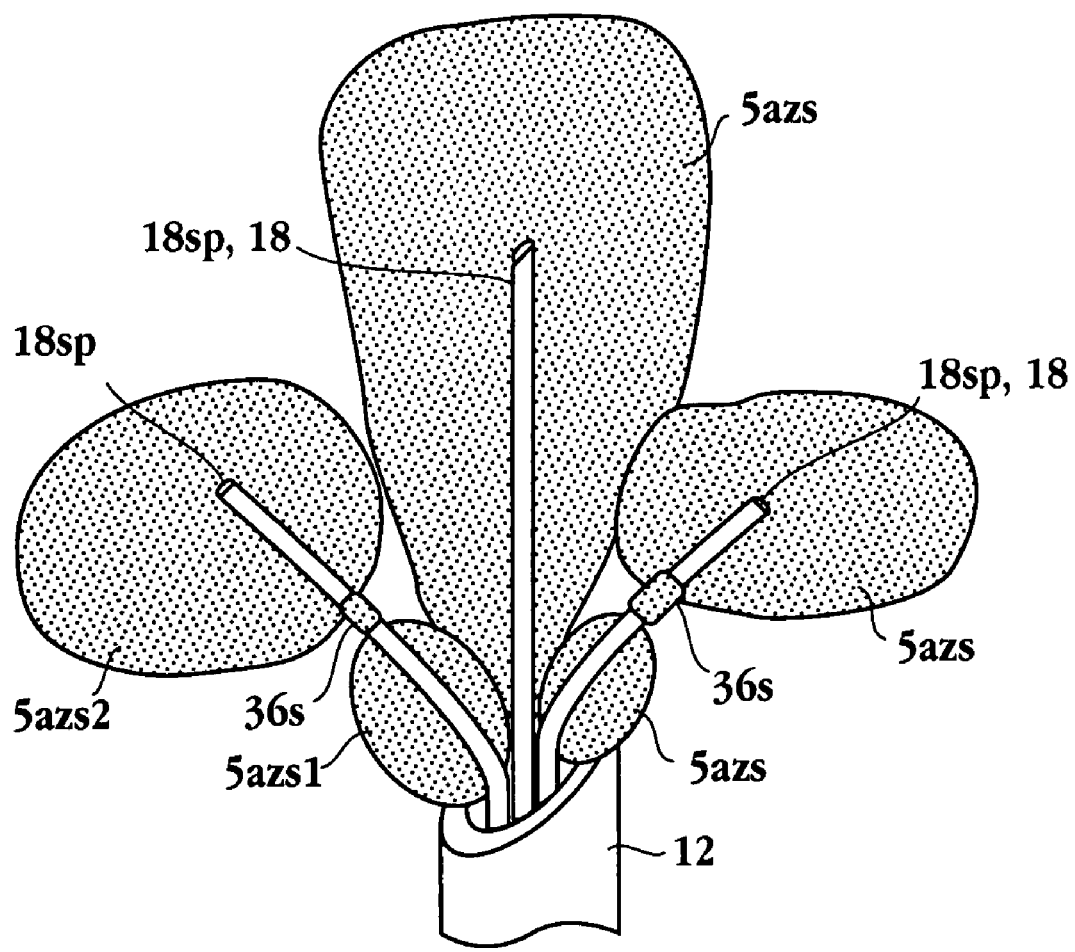
Figure 26A:
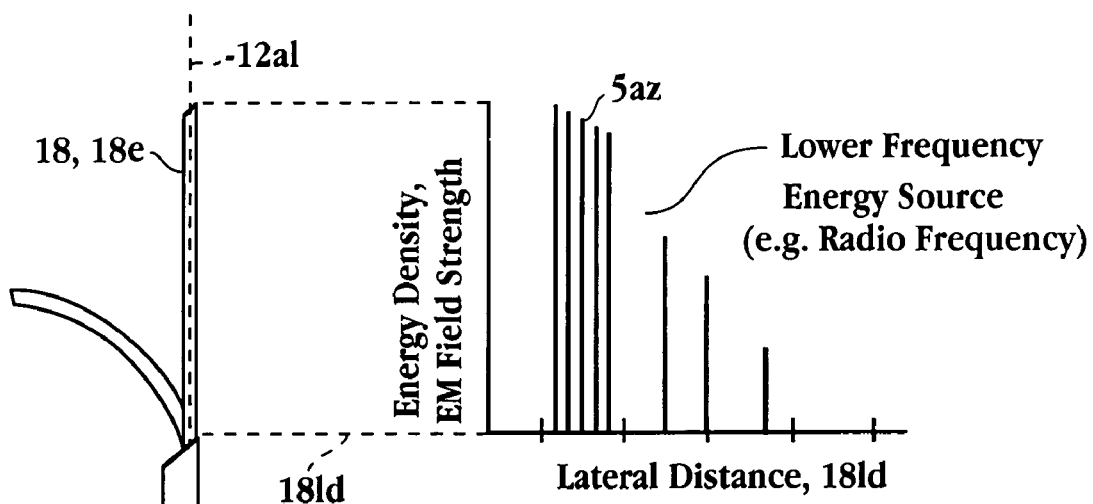
FIGS. 26a-26c are plots of energy density or concentration versus lateral distance from the electrode/energy delivery device of the embodiment of FIGS. 25a-25c.
Figure 26B:
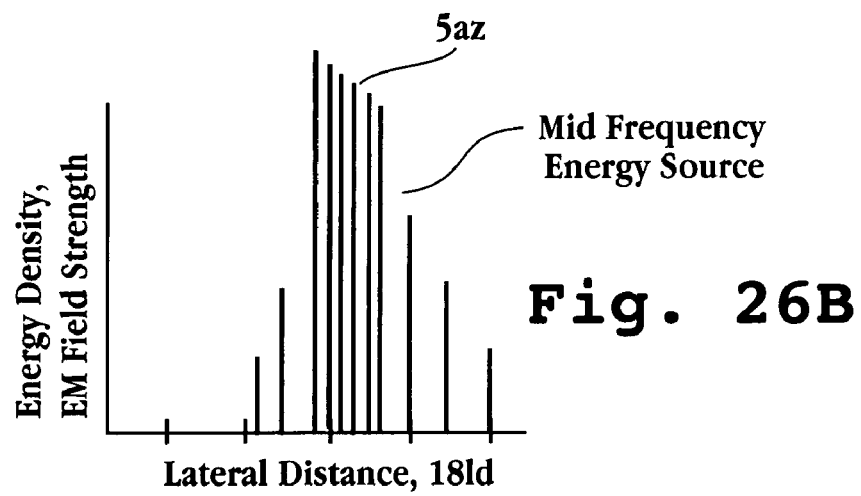
Figure 26C:
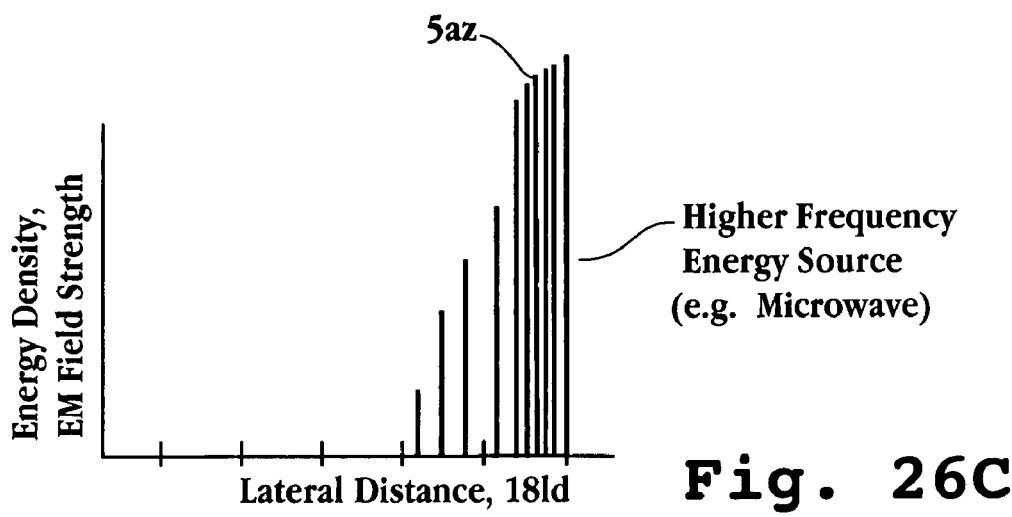

Referring now to FIGS. 25a-25c and 26a-26c, in an embodiment, the position and size of an ablation volume produced by the delivery of electromagnetic energy can be controlled via the frequency of the ablative energy delivered. Lower electromagnetic frequencies such as RF frequencies (e.g. 1 kHz to 1 MHZ) produce a more localized energy concentration (e.g. current density) with the resulting zone of energy concentration or ablation zone 5az occurring close to the energy delivery electrode/antenna in terms of a lateral distance 18dl or other direction. Higher frequencies such as microwaves result in a more distant energy concentration and resulting ablation zone. As shown in FIGS. 25a-25c, by varying the frequency of the delivered energy and/or utilizing energy delivery electrodes/antenna coupled to different frequency energy source (e.g. microwave vs. RF) the position, shape and size of the resulting lesion can be precisely controlled and even steered. This can be accomplished by electrically isolating one or more electrodes 18 to allow for the use of separate frequencies for each electrode. Further, one or more isolated electrodes can be coupled to multiplexing circuitry, and/or control resources coupled to the power sources and individual electrodes/antenna. Such circuitry and control resources can be used to turn individual electrodes or antenna off and on as well as control/set the frequency of each. In use, these and related embodiments provide the benefit of allowing the size, position and shape of the lesion to be precisely controlled and/or titrated in order to meet the therapeutic needs of the target tissue.

Referring now to FIGS. 25b and 25c, in various embodiments, one or more electrodes can have segmented portions 18sp so as to allow the electrodes to emit or radiate energy at different wavelengths from different segmented portions 18sp of the electrode 18. Segmentation can be achieved through the use of electrically insulated sections 36s.

In an embodiment shown in FIG. 25b, the use of segmented electrodes allows the creation of segmented ablation zones 5azs including a first and second segmented zone 5azs1 and 5azs2. The size and shape of the segmented ablation zones can be controlled by be discontinuous or overlapping. Such embodiments also provide the ability to avoid injury to anatomical structure such as blood vessels, nerves etc., which may be in close proximity or actually be surrounded by the tumor to be treated. For example, in an embodiment shown in FIG. 25b, the segmented ablation zones 5azs1 and 5azs2 can be sized and positioned (via frequency control of the ablative frequencies delivered to each electrode) to have sufficient space between each zone to avoid damaging a blood vessel 5bv or other critical structure 5as which lies between two or more electrodes 18. Alternatively, if desired, the ablative frequencies delivered to each electrode segmented portion 18sp could be reconfigured to produce overlapping segmented ablation zones 5azs as is shown in FIG. 25c.

In use, the medical practitioner would position the apparatus and then image the target tissue site (using imaging systems known in the art such as medical ultrasound or CAT scan technology) to identify both the tumor and critical structures and then utilize that image to control the input frequency to the energy delivery device to produce the desires lesion size and shape to completely ablate the tumor while avoiding the critical structure. In an embodiment, the image could be electronically stored and be analyzed to identify tumors and surrounding anatomy (using imaging processing methods known in the art such as edge detection algorithms resident within a processor of the imaging device) with the output feed into a power control software module, coupled to the power supply, that controls the power frequency to produce the desired ablation volume. Another benefit, of these and related embodiments, is the ability to produce an energy or thermal gradient within a target tissue site. That is, the ability to deliver more or less energy to discrete sections of the target tissue volume in order to titrate the delivery of energy to address the physical and thermal conditions of a particular tumor mass and even subsections of the tumor mass. This is an important capability because tumors are often morphologically, and therefore thermally non-homogeneous, a problem which current ablative therapies have not recognized or addressed.

Exemplary embodiments for the use of this capability include delivering larger amounts of energy to the center of a tumor and less to the periphery in order to produce higher temperatures and ensure complete ablation at the center and minimize risk of thermal injury to surrounding healthy tissue. Alternatively, increased energy could also selectively be directed to the tissue tract made by the RF needle or probe (or other penetrating energy delivery device) in penetrating the tumor and surrounding tissue to ensure that no living malignant tissue is dragged back through the tract upon removal of the RF needle.

Figure 27:
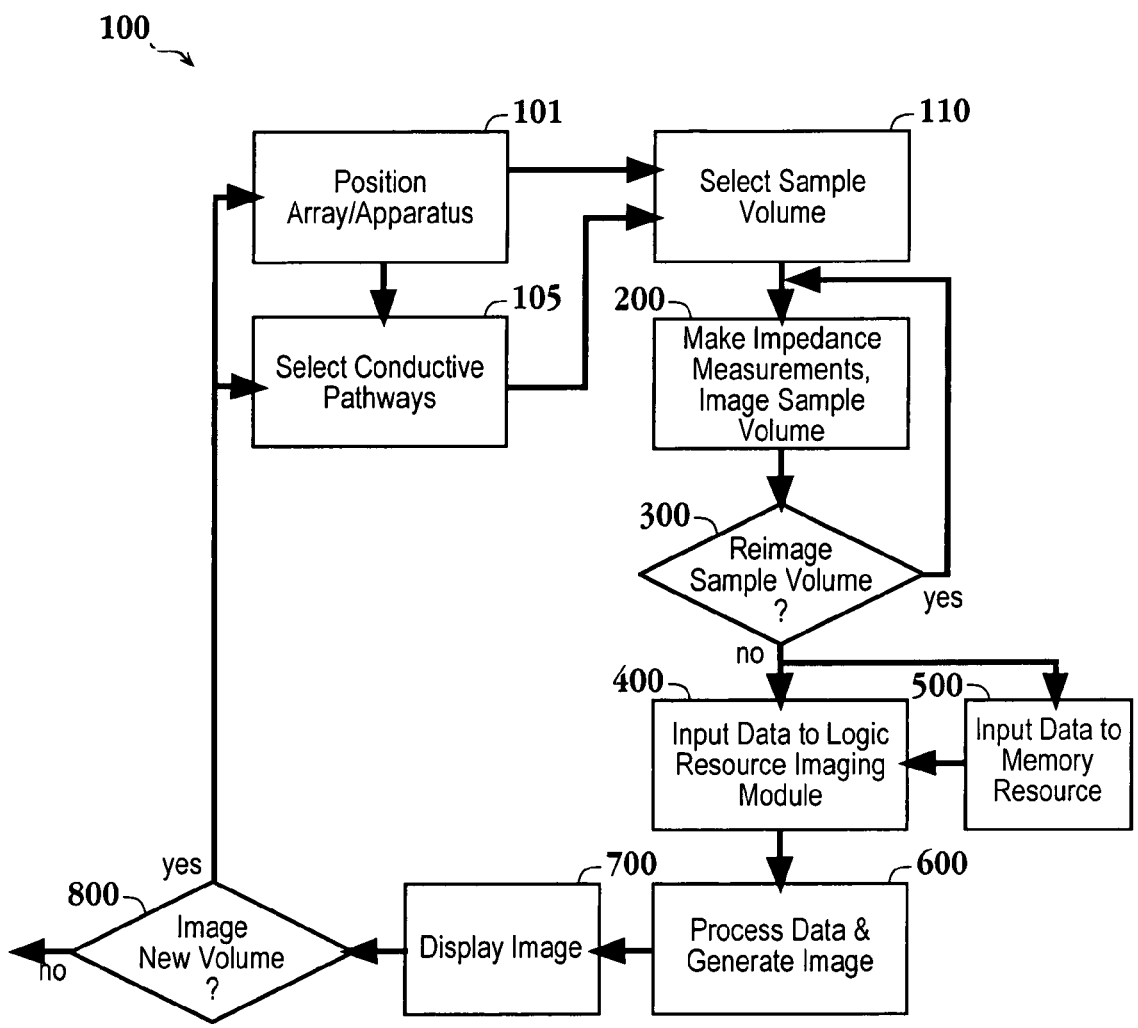
FIG. 27 is a flow chart illustrating a method for generating and displaying impedance derived images.

Referring now to FIGS. 3 and 27, various embodiments of the invention can be configured to generate and display images or maps from one or more impedance determinations including but not limited to complex impedance, impedance vectors, impedance loci and combinations thereof In an embodiment, a process 100 for generating and displaying an impedance map or impedance derived image 4' includes one or more of the following steps, all or a portion of which, can be implemented as an electronic instruction set on a processor or logic resources described herein. Impedance array 22$a$ and/or apparatus 10 can be positioned 101 within or near the desired sample volume 5$sv$ and/or conductive paths 22$cp$ can be selected 105 so as to define, and thus select 110, a particular sample volume 5$sv$. The volume is then imaged 200 using all or a portion of the sensing members 22$m$ or sensors 22 that comprise array 22$a$. A decision 300 can then be made to perform one or more re-images of the sample volume in order to enhance image resolution. Further, different excitation currents can be applied to the target tissue site and the voltage measurements repeated over time to increase measurement accuracy and precision through increased sampling and reducing signal bias or noise that may occur at a particular excitation current. Signals 22$i$ from impedance array 22$a$ can then be signaled or inputted 400 to logic resources 19$lr$ include module 19$m$ which can include an image processing sub-module 19$mi$. Sub-module 19$mi$ includes subroutines or algorithms configured to generate an impedance map or derived image 4' of all or a portion of the target tissue volume 5' using image/signal processing methods including, but not limited to, edge detection, filtering, approximating techniques, volume imaging, contrast enhancement, fuzzy logic and other methods known in the art. Alternatively, one or more signals 22$i$ from array 22$a$ can be inputted or signaled 500 to memory resources 19$mr$ (or an externally coupled data storage device) and stored as an impedance data set 22$ds$ in memory resources 19$mr$. Subsequently, all or a portion of data set 22$ds$ can inputted to sub-module 19$mi$ and processed 600 as described herein to generate an impedance map or impedance derived image 4' which can then be displayed 700 on display device 21 or other display means. A decision 800 can then be made to image a new sample volume and the process can repeated starting at the positioning step 101 or the selecting conductive pathway step 105. In an embodiment, the imaging or mapping process can be facilitated by rotating array 22$a$ about introducer axis 12$al$ or advancing and retracting one or more sensing members 22$m$ from members 18 or a combination of both.

In an embodiment, module 19$m$ or 19$mi$ can include an algorithm utilizing Laplace's equation to calculate impedivity or resistivity from the known voltages and currents measured at one or more conductive pathways 22$cp$ within the target tissue volume. Reference measurements or normalization methods may be used to account for noise in the measurements. In related embodiments impedance and other bioelectric measurements described herein can be analyzed and converted from the frequency domain to the time using transform function including Fourier transforms, fast Fourier transforms, wavelet analysis methods and other numerical methods known in the art. These functions and methods can be incorporated into algorithms or subroutine within module 19$m$ or 19$mi$. These algorithms incorporating wavelet functions and transforms (including packets) can be configured to analyze and solve multidimensional and multifrequency data and associated functions and equations. This approach provides the benefit of more flexibility in applying wavelets to analyze impedance, conductivity and other bioelectric data gathered using systems and apparatus of the present invention. One or more of the following wavelet functions can be incorporated into an algorithm or subroutine of module 19$m$ or 19$mi$: spline wavelets, waveform modeling and segmentation, time-frequency analysis, time-frequency localization, fast algorithms and filter banks, integral wavelet transforms, multiresolution analysis, cardinal splines, orthonormal wavelets, orthogonal wavelet spaces, wavelets of haar, shannon, and meyer; spline wavelets of battle—lemarié and strömberg; the daubechies wavelets; biorthogonal wavelets, orthogonal decompositions and reconstruction; and multidimensional wavelet transforms. In an exemplary embodiment modules 19$m$ or 19$mi$ utilizes spline wavelets to allow analysis and synthesis of discrete data on uniform or non-uniform tissue sample sites without any boundary effect.

Image module 19$mi$ can also include subroutines to perform interpolation such as linear, quadratic or cubic spline interpolation between individual determined impedance values from image data set of a given sample volume. This improves image quality including resolution without any substantial loss of spatial or contrast detail. In related embodiments, the image processing module 19$mi$ can be configured to allow the user to select both the interpolative or other image processing algorithms to be performed as well as the area of the image to be so processed. Thus, the user can select all or a portion of the image to enhance, providing faster image processing times (by not having to process the entire image) as well improving image quality and other overall usability of the imaging apparatus/system. The image processing module 19$mi$ can also include gray scale and color contrast capabilities which can be selectable. Both the gray scale and color can be scaled or normalized against a baseline measurement obtained from the individual patient, a calibration measurement or a statistic (e.g. mean) value for a patient sample group or a parameter (e.g. average) for a patient population or a combination thereof.

In related embodiments, monitoring apparatus 19 and module 19$mi$ can be configured to generate impedance images with the maximum visual distinction or contrast between tumorous tissue and healthy tissue. This can be accomplished by using the frequency or combination of frequencies that yield the maximum sensitivity for selected tissue types or tissue conditions indicative of a tumor (e.g. degree of vascularity temperature etc). In an embodiment, such frequencies can be determined by performing swept frequency measurements and generating an impedance map or image using one or more frequencies which resulted in the best contrast between healthy tissue and tumorous tissue or other tissue condition (e.g. thermal injury, necrosis etc.).

Figure 28:
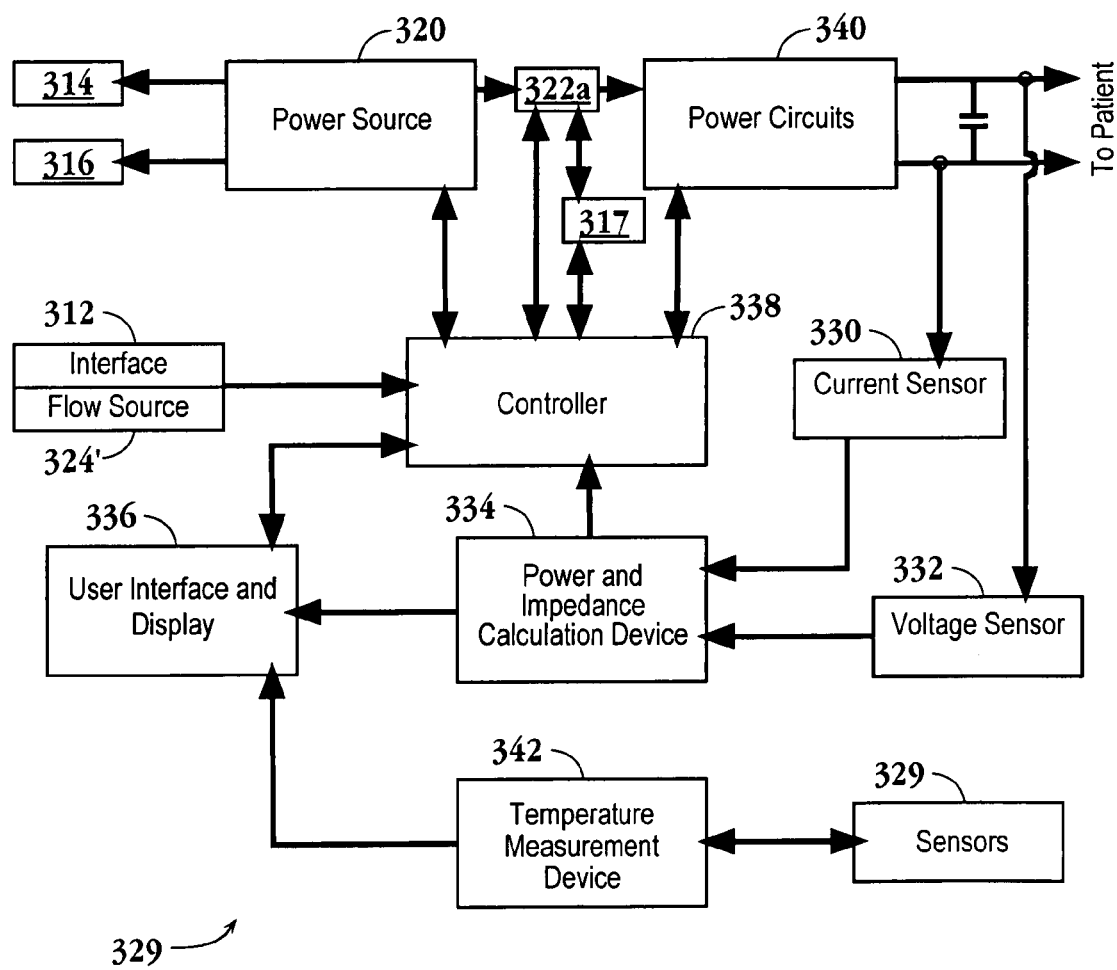
FIG. 28 is a block diagram illustrating a controller, power source, power circuits and other electronic components used with an embodiment of a control system other embodiments of the invention.
Figure 29:
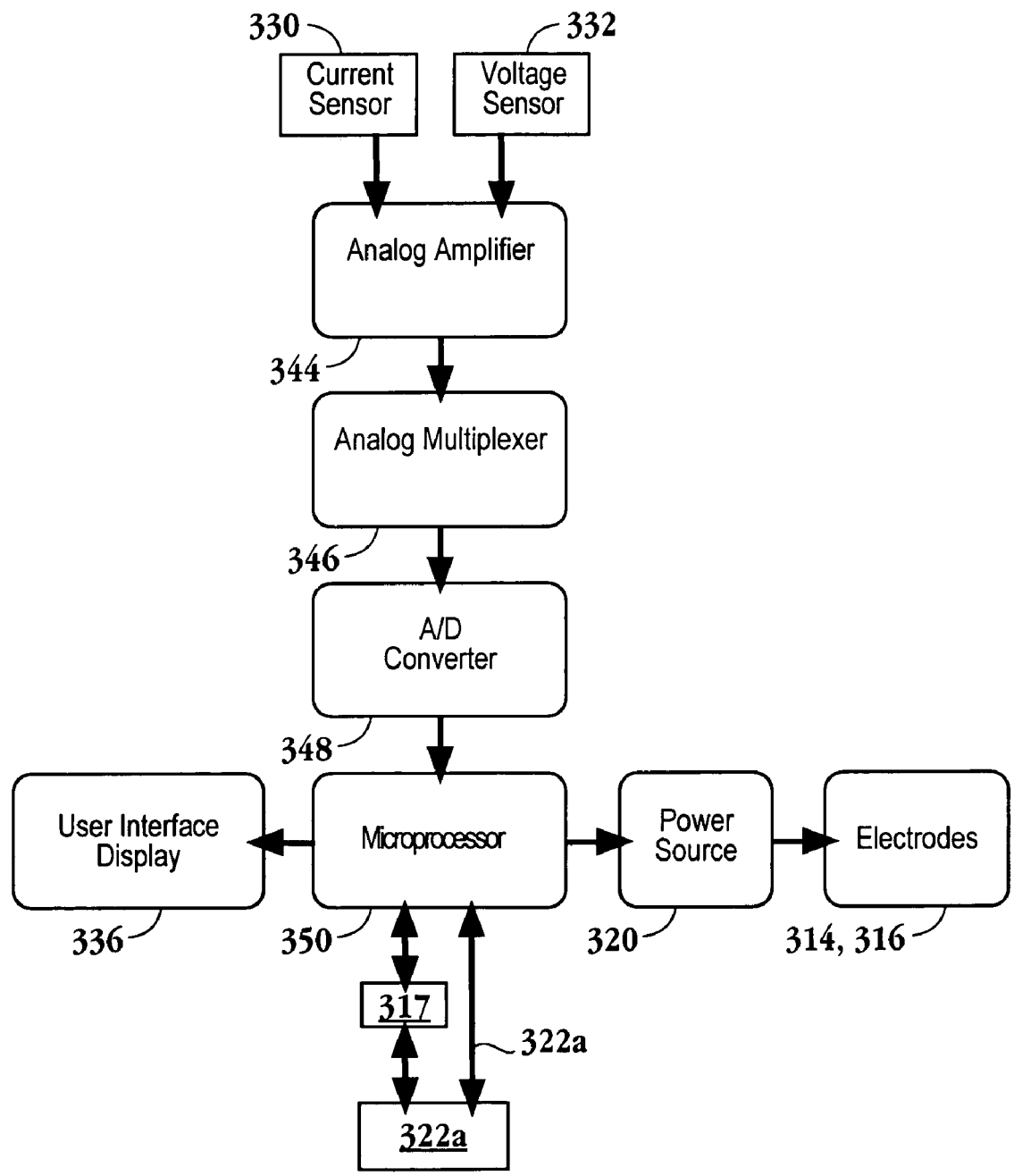
FIG. 29 is a block diagram illustrating an analog amplifier, multiplexer and microprocessor used with an embodiment of a control system or other embodiments of the invention.

Referring now to FIGS. 28 and 29, a feedback control system 329 can be connected to energy source 320, sensors 324 impedance array 322a and energy delivery devices 314 and 316. Feedback control system 329 receives temperature or impedance data from sensors 324 and the amount of electromagnetic energy received by energy delivery devices 314 and 316 is modified from an initial setting of ablation energy output, ablation time, temperature, and current density (the "Four Parameters"). Feedback control system 329 can automatically change any of the Four Parameters. Feedback control system 329 can detect impedance or temperature and change any of the Four Parameters in response to either or a combination. Feedback control system 329 can include a multiplexer (digital or analog) to multiplex different electrodes, sensors, sensor arrays and a temperature detection circuit that provides a control signal representative of temperature or impedance detected at one or more sensors 324. A microprocessor can be connected to the temperature control circuit.

The following discussion pertains particularly to the use of an RF energy as an ablative energy source for the apparatus. For purposes of this discussion, energy delivery devices 314 and 316 will now be referred to as RF electrodes/antennas 314 and 316 and energy source 320 will now be an RF energy source. However it will be appreciated that all other energy delivery devices and sources discussed herein are equally applicable and devices similar to those associated with the treatment apparatus can be utilized with laser optical fibers, microwave devices and the like. The temperature of the tissue, or of RF electrodes 314 and 316 is monitored, and the output power of energy source 320 adjusted accordingly. The physician can, if desired, override the closed or open loop system.

The user of the apparatus can input an impedance value that corresponds to a setting position located at the apparatus. Based on this value, along with determined impedance values, feedback control system 329 determines an optimal power and time needed in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 316 from the distal end of the introducer to a position corresponding to a desired lesion size and monitoring the temperature at the periphery of the lesion such that a temperature sufficient to produce a lesion is attained.

The closed loop system 329 can also utilize a controller 338 to monitor the temperature, adjust the RF power, analyze the result, refeed the result, and then modulate the power. More specifically, controller 338 governs the power levels, cycles, and duration that the RF energy is distributed to electrodes 314 and 316 to achieve and maintain power levels appropriate to achieve the desired treatment objectives and clinical endpoints. Controller 338 can also in tandem analyze spectral profile 19p and perform tissue biopsy identification and ablation monitoring functions including endpoint determination. Further, controller 338 can in tandem govern the delivery of electrolytic, cooling fluid and, the removal of aspirated tissue. Controller 338 can be integral to or otherwise coupled to power source 320. In this and related embodiments, controller 338 can be coupled to a separate impedance determination current source 317 and can be configured to synchronize the delivery of pulsed power to tissue site to allow for sensing by sensors or sensor array 322a during off power off intervals to prevent or minimize signal interference, artifacts or unwanted tissue effects during sampling by sensors 324 or sensor array 322a. The controller 338 can also be coupled to an input/output (I/O) device such as a keyboard, touchpad, PDA, microphone (coupled to speech recognition software resident in controller 338 or other computer) and the like. In an embodiment current source 317 can be a multi-frequency generator such as those manufactured by the Hewlett Packard Corporation (Palo Alto, Calif.) and can include or be coupled to a spectrum analyzer manufactured by the same company.

Referring now to FIG. 28, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334. These values can then be displayed at a user interface and display 336. Signals representative of power and impedance values are received by controller 338 which can be a microprocessor 338.

A control signal is generated by controller 338 that is proportional to the difference between an actual measured value and a desired value. The control signal is used by power circuits 340 to adjust the power output in an appropriate amount in order to maintain the desired power delivered at the respective primary and/or secondary antennas 314 and 316. In a similar manner, temperatures detected at sensors 324 provide feedback for maintaining a selected power. The actual temperatures are measured at temperature measurement device 342, and the temperatures are displayed at user interface and display 336. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensor 324. A multiplexer 346 can be included to measure current, voltage and temperature, at the numerous sensors 324 as well as deliver and distribute energy between primary electrodes 314 and secondary electrodes 316. Suitable multiplexers include but are not limited to those manufactured by the National Semiconductor® Corporation (Santa Clara, Calif.) such as the CLC 522 and CLC 533 series; and those manufactured the Analog Devices® Corporation (Norwood, Mass).

Controller 338 can be a digital or analog controller, or a computer with embedded, resident or otherwise coupled software. In an embodiment controller 338 can be a Pentium® family microprocessor manufacture by the Intel® Corporation (Santa Clara, Calif.). When controller 338 is a computer it can include a CPU coupled through a system bus. On this system can be a keyboard, a disk drive, or other non-volatile memory systems, a display, and other peripherals, as are known in the art. Also coupled to the bus are a program memory and a data memory. In various embodiments, controller 338 can be coupled to imaging systems, including but not limited to ultrasound, CT scanners (including fast CT scanners such as those manufacture by the Imatron® Corporation (South San Francisco, Calif.), X-ray, MRI, mammographic X-ray and the like. Further, direct visualization and tactile imaging can be utilized.

User interface and display 336 can include operator controls and a display. In an embodiment user interface 336 can be a PDA device known in the art such as a Palm® family computer manufactured by Palm® Computing (Santa Clara, Calif.). Interface 336 can be configured to allow the user to input control and processing variables, to enable the controller to generate appropriate command signals. Interface 336 can also receives real time processing feedback information from one or more sensors 324 for processing by controller 338, to govern the delivery and distribution of energy, fluid etc.

The output of current sensor 330 and voltage sensor 332 is used by controller 338 to maintain a selected power level at primary and secondary antennas 314 and 316. The amount of RF energy delivered controls the amount of power. A profile of power delivered can be incorporated in controller 338, and a preset amount of energy to be delivered can also be profiled.

Circuitry, software and feedback to controller 338 results in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 324. A controller 338 can be incorporated into feedback control system 329 to switch power on and off, as well as modulate the power. Also, with the use of sensor 324 and feedback control system 329, tissue adjacent to RF electrodes 314 and 316 can be maintained at a desired temperature for a selected period of time without causing a shut down of the power circuit to electrode 314 due to the development of excessive electrical impedance at electrode 314 or adjacent tissue.

Referring now to FIG. 29, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage which represents the respective sensed temperatures. Digitized amplifier output voltages are supplied by A/D converter 348 to a microprocessor 350. Microprocessor 350 may be a Power PC® chip available from Motorola or an Intel® Pentium® Series chip. However, it will be appreciated that any suitable microprocessor or general purpose digital or analog computer can be used to calculate impedance or temperature or perform image processing and tissue identification functions.

Microprocessor 350 sequentially receives and stores digital representations of impedance and temperature. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with power and impedance limits. When the values exceed predetermined power or impedance values, a warning can be given on user interface and display 336, and additionally, the delivery of RF energy can be reduced, modified or interrupted. A control signal from microprocessor 350 can modify the power level supplied by energy source 320 to RF electrodes 314 and 316. In a similar manner, temperatures detected at sensors 324 provide feedback for determining the extent and rate of (i) tissue hyperthermia (ii) cell necrosis; and (iii) when a boundary of desired cell necrosis has reached the physical location of sensors 324.

Figure 30:
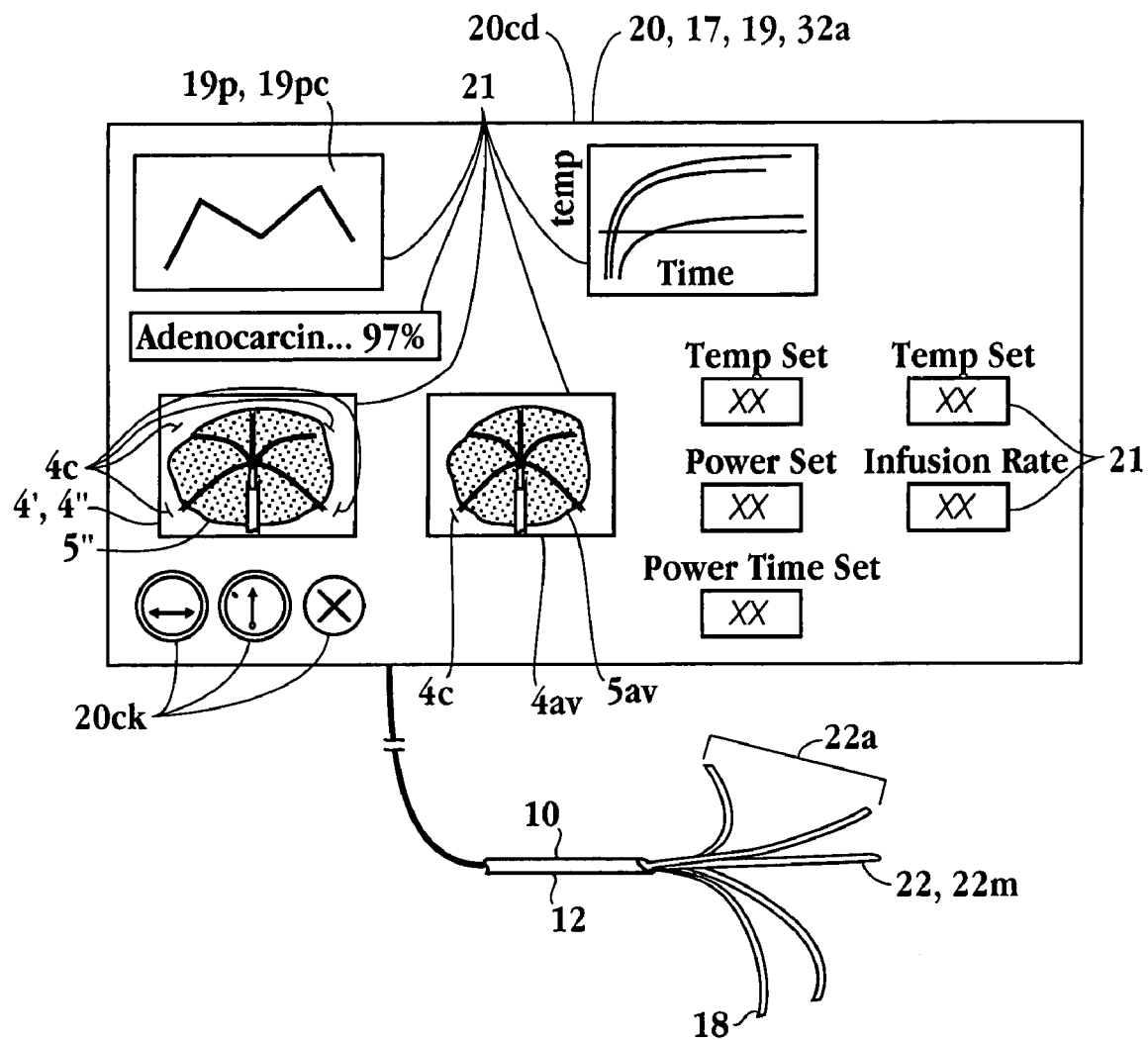
FIG. 30 is a lateral view illustrating a control and display unit used in various embodiments of the invention.

Referring now to FIG. 30, in an embodiment one or more of the impedance determination device 19, power supply 20, display device 21 and control system, the controller can be incorporated or integrated into a single control and display device or unit 20cd. Device 20cd can configured to include display one or more of the following: impedance profile 19p, tissue site image 4', tumor volume image 4", ablation volume image 4av, time temperature profiles, tissue identification information, and ablation setting information (e.g. power setting, delivery time etc.). The device 20cd can also be configured to superimpose ablation volume image 4av onto tumor volume image 4" or tissue site image 4' as well as superimpose visual cues 4c on the placement (including proper and improper placement) of the apparatus 10 including energy delivery devices within the tumor volume or a tissue site. The device 20cd can also include controls knobs 20ck for manipulating any of the images (4', 4" or 4av) in one or more axis.

Figure 31:
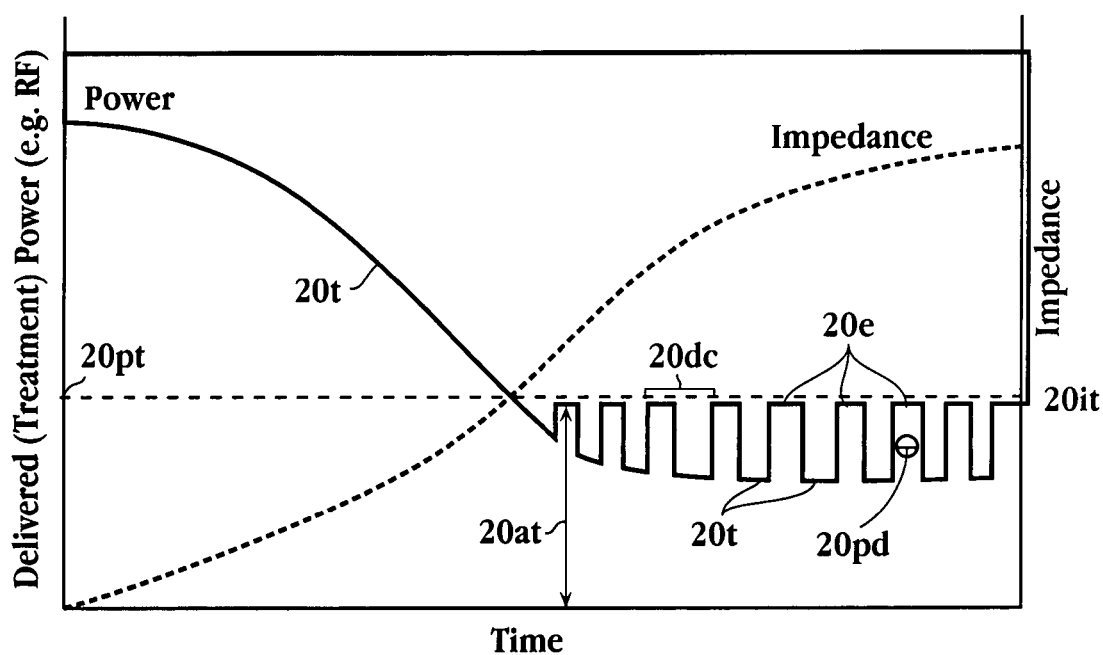
FIG. 31 is a plot showing an embodiment of an impedance determination duty cycled signal super-imposable on an RF treatment signal under selectable threshold conditions.

Referring now to FIG. 31, in various embodiments, impedance determination apparatus or the control system can be configured to switch from a first mode of measuring impedance to a second mode when certain system impedance or power conditions occur. In an embodiment, the first mode of measuring impedance is done utilizing the RF treatment power and then impedance is calculated using a measured current and voltage as described herein. However, when system impedance rises greatly and the resulting RF power treatment power level drops below a threshold the accuracy and precision of localized impedance determinations decreases as a result due in part to the decrease in the impedance determination current in relation to noise levels of the RF power system. This is a problem not recognized nor addressed by current RF ablative/impedance determination devices. Under such conditions logic resources within monitoring device can be configured to switch to a second mode of measuring localized impedance. The threshold event causing the mode switching can be selectable and include one or more of the following: threshold decreases in treatment (e.g. RF) power, increases in system impedance, changes in slope (e.g. derivative) of the RF power or system impedance curves. In various embodiments, the threshold level of RF treatment power causing mode switching can be in the range from 1 to 50 watts with specific embodiments of 5, 10 and 25 watts.

In an embodiment shown in FIG. 31, an alternative mode of measuring impedance is shown comprising superimposing a duty cycled measurement signal 20e onto the treatment signal 20. The pulse duration 20pd of signal 20e can be in the range of 1 to 500 ms with specific embodiments of 50, 100 and 250 ms. The duty cycle 20dc of signal 20e can be in the range from 1 to 99% with specific embodiments of 10, 25, 50 and 75%. The monitoring device, power source or control system can be configured to control the power amplitude of the measurement signal to maintain a selected total signal amplitude 20at. In an embodiment the total signal amplitude 20at can range from about 5 to about 50 watts, with specific embodiments of 10, 20, 30 and 40 watts Also the duty cycle, pulse duration and total signal amplitude can be controlled to deliver a selectable average power over the duty cycle which can be in the range of about 0.5 to about 10 watts with specific embodiments 1, 2, 5 and 5 watts. By controlling the average power delivered over the duty cycle higher measurements currents can be used in short pulse duration without appreciably affecting delivered treatment power, system performance or causing additional or unwanted energy delivery to the target tissue site.

In use, these and related embodiments of alternative measurement of impedance determinations including superimposed duty cycle measurement, provide the benefit of improved accuracy and signal to noise ratios of impedance and related bio-electric measurements under conditions of high system impedance and/or lower levels of delivered RF treatment power (i.e. ablative power).

In related embodiments, the duty cycle and/or pulse duration can be configured to vary responsive to one or more selected parameters which can include frequency of the treatment signal, power of the treatment signal, or impedance of the treatment signal. The variation in either the pulse duration or duty cycle can be controlled by a control system and/or logic resources of the impedance monitoring device or power supply using control methods known in the art such as PID control. In use, these embodiments allow the impedance determinations to be continuously fine tuned to changing system conditions to improve the accuracy and precision of impedance and related bioelectric measurements.

Figure 32:
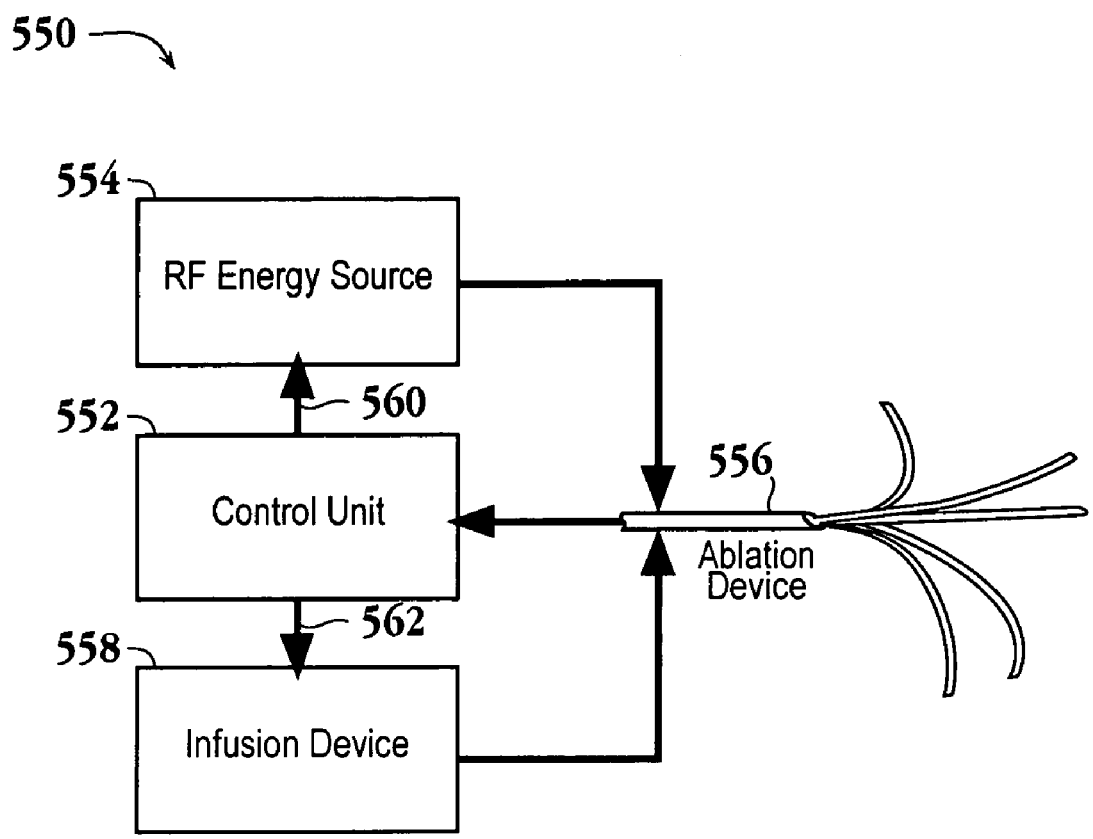
FIG. 32 is a diagram illustrating an embodiment of the device for impedance modulation with infusion.

FIG. 32 illustrates a tissue ablation system or apparatus 550, much of which has been described above. The apparatus generally includes a control unit 55 which is designed to operate in the manner described more fully below with respect to FIG. 33. The control unit is operably connected to an RF energy source 554, such as an energy source of the type described above, for controlling the energy output, e.g., power output, from the energy source to the electrodes in a multi-electrode ablation device 556, of the type described above. The operable connection between unit 552 and energy source, indicated at 560, may be any conventional electronic or mechanical control, e.g., a servo motor, by which electronic signals from the control unit can be used to vary the power output of source 554.

The output of the energy source is electrically connected to the electrodes of a multi-electrode ablation device, as above, for varying the RF power delivered to the electrodes, for varying the rate of ablation by the device, when the electrodes are deployed in a target tissue, as detailed above.

The control unit is also operably connected to an infusion device 558, such as a pump or the like, to control the rate and/or pressure of fluid, e.g., saline solution, supplied to electrodes or other fluid-infusion channels in the ablation device through fluid-carrying tubes, indicated 561. The operative connection between unit 552 and the infusion device is indicated at 562, and may be may be any conventional electronic or mechanical control, e.g., a servo motor, by which electronic signals from the control unit can be used to vary the pumping rate or pressure at which fluid is supplied by device 558 to the ablation device.

An electrical connection 553 between the ablation device and control unit is used for transmitting electrical signals related to the output of temperature sensors carried on the ablation device electrodes, as described above and/or for transmitting current-level information relating to current flow between electrodes and an exterior body surface, (for global impedance measurements) or between electrodes or regions of one electrode (for local impedance measurements). Such impedance and/or temperature measurements may be instantaneous values, or values relating to change in impedance and/or temperature over time.

Figure 33:
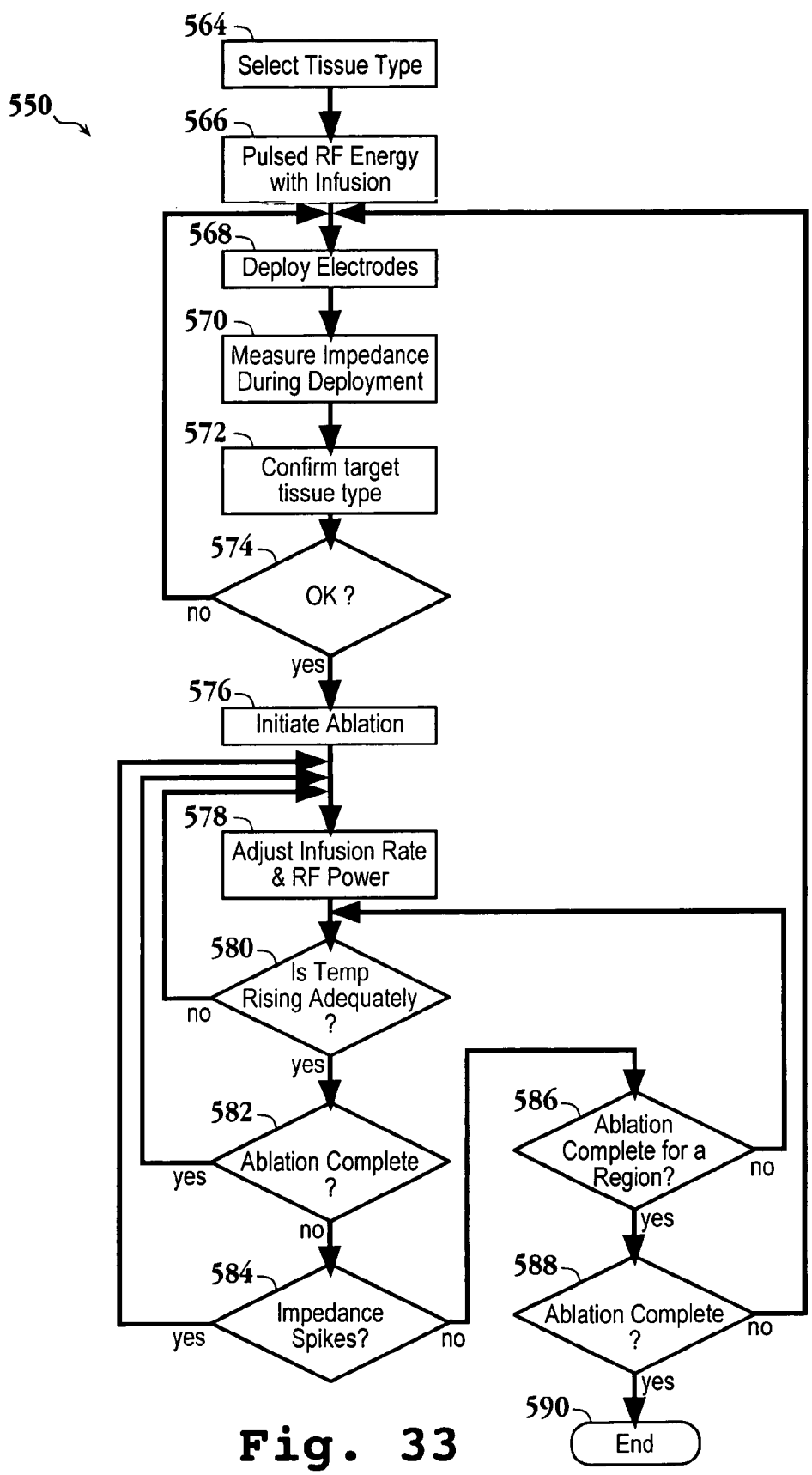
FIG. 33 is a flow chart illustrating the use of one embodiment of the device.

FIG. 33 is a flow diagram illustrating various functions and operations in the control unit, as they related to control of the RF energy source and control of the infusion device. At the outset, it is noted that control unit may automatically control the operation of the both the energy and infusion devices, without user intervention, or may provide information to the user which indicates how the user should control the operational levels of one or both of the energy device and infusion device, to optimize the ablation procedure, and in particular, to ensure complete tissue ablation with a minimum of charring and collateral damage to nearby healthy tissue.

Initially, the user may input the type of target tissue, e.g., liver tumor, bone tumor, or the like, as indicated at 564. The control unit preferably stores data relating to the impedance characteristics of tissue and/or rates of heating and changes in impedance for specific tissue types, when a given power level is applied, preferably in the presence of infusate. This internal data will be used, as seen below, to confirm that the tissue into which the electrodes of the ablation device have been deployed is the desired tissue type, based on impedance and/or temperature changes detected during an initial phase of system operation.

When the user is ready to insert the device into the patient, and deploy the electrodes into the target tissue, to define a selected volume for tissue ablation, the system operates to begin fluid infusion through the device and also controls the energy device to deliver low-power, pulsed RF energy to the electrodes being deployed, as indicated at 566. The low-power pulses are used to generate global or localized current values for purposes of measuring global or local impedance values as the electrodes are being deployed, as indicated at 568 and 570. The power supplied to the electrodes during deployment may also be sufficient to cause very localized heating around the electrodes, to facilitate entry of the electrodes into the target tissue. The ablation device may also signal the control unit, through connection 553 (FIG. 33) when a selected degree of electrode deployment, corresponding to a desired tissue volume, is reached.

The Impedance (and/or temperature) measurements made during electrode deployment may be compared with the tissue-specific impedance or temperature data stored in the control unit, to confirm that the tissue enveloped by the electrodes is in fact the selected target tissue. If the program finds a mismatch, as at 574, control unit may signal the user to redeploy the electrodes, as indicated. If a tissue-confirmation is made, the program proceeds, indicating to the user to initiate the ablation procedure, or automatically initiating the ablation phase of the operation, by advancing the power level delivered by the energy source to a desired level, and optionally, increasing the rate of fluid infusion to the tissue, as indicated at 576.

Once the ablation operation is underway, system makes continual and periodic impedance and/or temperature measurements at the target-tissue site, and performs automatic or user-controlled adjustments in the power level and/or infusion rate, to achieve a desired rate and extent of ablation, as indicated at 570. As indicated above, when this adjustment is carried out automatically, the control unit operates to automatically adjust the power level and/or infusion rate of devices 554, 562, respectively (FIG. 32). Alternatively, the control unit may have a display for indicating to the user the direction and extent of adjustment requirement, and controls for making those adjustments.

Throughout the period of adjustment, the control unit is receiving periodic and repeated impedance and/or temperature data which is being processed to guide the control of the energy and infusion devices. The data-processing operations are indicated at the bottom in FIG. 32. Initially, and as indicated at 580, the program asks whether the temperature is rising adequately (it is desired to complete the ablation within as short a time as possible, consistent with the objective of optimal tissue ablation). If the rate of temperature rise is below a selected threshold, the control unit may operate (or instruct the user) to adjust the power and/or rate of infusion to the tissue, to enhance the rate of heating, for example, by increasing power or reducing infusion. The program also asks whether the measured impedance is above a desired threshold, as at 582. If the measured impedance is too low, again the program will operate (or instruct the user) to adjust the power delivery to the electrodes and/or the rate of infusion of electrolyte to the tissue. This procedure is repeated until both temperature change and impedance levels are within selected acceptable ranges.

The program also looks for impedance spikes, indicative of charring or overheating. If these are observed, through logic decision 584, the control unit may operate to adjust (or instruct the user to adjust) either power level of rate of infusion to minimize so as to reduce impedance spikes.

Assuming all of these variables are within acceptable levels, the system is properly adjusted to maximize the ablation process, that is, to achieve ablation at about the highest rate that does not lead to tissue charring (or excessive tissue charring) or ablation damage to collateral healthy tissue. The program now monitors when complete ablation is achieved in the region of the electrodes, as at 586. If ablation is incomplete, the program may continue ablation at the existing power and/or infusion rate levels, or adjust the levels as appropriate.

If complete local ablation is achieved, the system may then ask whether ablation of the total target area is ablated, as at 558. If it is, the program operation is at end, and the system may terminate or power down to a lower power/infusion levels. For example, some RF power may be supplied to the electrodes during electrode retraction or catheter retraction, to reduce the risk exposing healthy tissue to tumor cells, during removal of the ablation device from the patient.

If the total ablation is incomplete, the system signals the user to advance the deployment of the electrodes, and the above ablation process is repeated until a final target-tissue ablation is achieved.

CONCLUSION

It will be appreciated that the applicants have provided a novel and useful apparatus and method for the diagnosis and treatment of tumors using minimally invasive methods including tissue impedance determinations. The foregoing description of various embodiment of the invention has been presented for purposes of illustration and description. It is not intended to be exhaustive or to limit the invention to the precise forms disclosed. Embodiments of the invention can be configured for the treatment of tumor and tissue masses at or beneath a tissue surface in a number of organs including but no limited to the liver, breast, bone and lung. However, embodiments of the invention are applicable to other organs and tissue as well. Obviously, many modifications and variations will be apparent to practitioners skilled in this art. Further, elements from one embodiment can be readily recombined with elements from one or more other embodiments. Such combinations can form a number of embodiments within the scope of the invention. It is intended that the scope of the invention be defined by the following claims and their equivalents.

What is claimed is:

1. A cell necrosis apparatus for use in ablating target tissue, comprising, in operative condition:
    an elongated delivery device including a lumen;
    an energy delivery device including a plurality of electrodes, each electrode having a tissue piercing distal portion and being positionable in the elongated delivery device in a compacted state and preformed to assume a curved shape when deployed, the plurality of electrodes exhibiting a changing direction of travel when advanced from the elongated delivery device to a selected tissue site and defining an ablation volume when in said deployed state, said energy delivery device being operably connected to a source of energy;
    at least two of the plurality of electrodes being adapted for fluid delivery therethrough to at least one infusion port, wherein said at least two electrodes adapted for fluid delivery are operably connected to a fluid delivery device
    an energy control unit operably connected to (i) the source of energy, for controlling energy delivery to said energy delivery device, and to (ii) the energy delivery device for use in detecting impedance; and
    a fluid control operatively connected the fluid delivery device by which the amount of fluid infused from the device into the target tissue can be controlled in response to said detected impedance, wherein said fluid control is operable to provide independent control of infusion through the separate infusion lumens.

2. The apparatus according to claim 1, wherein said energy control unit is operably connected to at least one of the plurality of electrodes to determine tissue impedance.

3. The apparatus of claim 2, wherein local impedance is determined directly by determining the impedance along conductive pathways between one or more sites on at least one of the plurality of electrodes.

4. The apparatus of claim 3, wherein said one or more sites is at least two sites on the same electrode for determining local impedance across a fixed distance.

5. The apparatus according to claim 2, wherein at least one of said plurality of electrodes is a passive electrode, and the energy control unit is operably connected to said passive electrode(s).

6. The apparatus according to claim 1, further comprising:
    a temperature sensor positioned on at least one of the plurality of electrodes and operably connected to the control unit.

7. The apparatus according to claim 1, where said energy control unit is operably connected to said fluid delivery device for regulating the amount of fluid infused from the fluid delivery device in response to said detected impedance.

8. The apparatus according to claim 1, where the energy control unit is manually adjustable for regulating the amount of energy delivered to said at least one electrode in response to said detected impedance.

9. The apparatus according to claim 1, where the energy control is manually adjustable for regulating the amount of fluid infused from the fluid delivery device in response to said detected impedance.

10. The apparatus of claim 1, said elongated delivery device being adapted for fluid delivery therethrough to at least one infusion port.

11. A method for use in ablating target tissue in a patient, comprising:
    positioning in the patient an energy delivery device having (a) an elongated delivery device that includes a lumen, (b) a plurality of electrodes, with a tissue piercing distal end, that are positionable in the delivery device in a compact state and preformed to assume a curved shape when deployed, the plurality of electrodes exhibiting a changing direction of travel when advanced from the delivery device to a selected tissue site, at least two of the plurality of electrodes being adapted for fluid delivery therethrough to at least one infusion port; and wherein said positioning is effective to place the distal tip of the elongated delivery device in or adjacent a target tissue;

deploying said plurality of electrodes from said delivery device to define an ablation volume that includes at least a portion of the target tissue, selectively infusing a fluid from a fluid delivery device operatively connected to said at least two electrodes and through the electrodes into the defined ablation volume to provide independent infusion through each of the electrodes;

applying an ablating current to the electrodes, by said applying, ablating target tissue contained within the defined volume, determining impedance; and regulating the impedance by controlling the amount of fluid infused from the at least two electrodes.

12. The method of claim 11, where said infusing step is performed at one or more of prior to, during, and after said ablating step.

13. The method of claim 11, wherein said regulating step includes varying the fluid flow at different electrodes of the at least two of electrodes.

14. The method of claim 11, wherein said ablating step is additionally performed during said deploying step.

15. The method of claim 11, wherein the fluid infused is an infused electrolytic solution and the method further comprises varying the conductivity of the infused solution, by controlling the concentration of an electrolyte in the infused electrolytic solution.

16. The method of claim 15, wherein said infused electrolytic solution is a saline solution and the conductivity of the infused electrolytic solution is controlled by varying the salinity of the solution.

17. The method of claim 15, wherein said infusing step is effective to control a zone of infusion around individual electrodes of the plurality of electrodes.

18. The method of claim 11, wherein said impedance is system or local impedance determined from the impedance between one or more electrodes of the plurality of electrodes and an exterior of the patient for system impedance, and between electrodes or between two or more sites on the same electrode for local impedance.

19. The method of claim 18 further comprising:

maximizing a power dissipation efficiency by controlling system and/or local impedance to an optimal value.

20. The method of claim 18, wherein said controlling impedance is controlling impedance between a minimum value and maximum value.

21. The method of claim 18, wherein said infusing step is performed at a preprogrammed flow rate profile to produce a time variable impedance profile.

22. The method of claim 18, wherein determining said impedance is performed with a frequency selected from the group consisting of the same frequency as an energy source connected to the plurality of electrodes, a different frequency from the energy source and a range of frequencies.

* * * * *